(12) United States Patent
Chilkoti et al.

(10) Patent No.: US 10,364,451 B2
(45) Date of Patent: Jul. 30, 2019

(54) POLYMER CONJUGATES HAVING REDUCED ANTIGENICITY AND METHODS OF USING THE SAME

(71) Applicant: Duke University, Durham, NC (US)

(72) Inventors: Ashutosh Chilkoti, Durham, NC (US); Yizhi Qi, Durham, NC (US); Michael S. Hershfield, Durham, NC (US); Nancy J. Ganson, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/387,536

(22) Filed: Dec. 21, 2016

(65) Prior Publication Data

US 2017/0239363 A1 Aug. 24, 2017

Related U.S. Application Data

(63) Continuation-in-part of application No. 14/894,731, filed as application No. PCT/US2014/040319 on May 30, 2014, now Pat. No. 9,592,303.

(60) Provisional application No. 62/407,403, filed on Oct. 12, 2016, provisional application No. 62/329,800, filed on Apr. 29, 2016, provisional application No. 62/310,534, filed on Mar. 18, 2016, provisional application No. 62/270,401, filed on Dec. 21, 2015, provisional application No. 61/828,873, filed on May 30, 2013.

(51) Int. Cl.
| | | |
|---|---|---|
| *C12P 21/00* | (2006.01) | |
| *C12N 9/96* | (2006.01) | |
| *A61K 47/60* | (2017.01) | |
| *A61K 47/58* | (2017.01) | |

(52) U.S. Cl.
CPC ............ *C12P 21/00* (2013.01); *A61K 47/58* (2017.08); *A61K 47/60* (2017.08); *C12N 9/96* (2013.01); *C08F 2438/00* (2013.01)

(58) Field of Classification Search
CPC ......... C12P 21/00; A61K 47/58; A61K 47/60; C12N 9/96; C08F 2438/00
See application file for complete search history.

(56) References Cited

U.S. PATENT DOCUMENTS

| | | | |
|---|---|---|---|
| 4,554,101 A | 11/1985 | Hopp | |
| 4,976,734 A | 12/1990 | Urry et al. | |
| 5,250,516 A | 10/1993 | Urry | |
| 5,336,256 A | 8/1994 | Urry | |
| 5,578,577 A | 11/1996 | Ching et al. | |
| 5,580,859 A | 12/1996 | Felgner et al. | |
| 5,676,646 A | 10/1997 | Hofmann et al. | |
| 5,679,647 A | 10/1997 | Carson et al. | |
| 5,702,359 A | 12/1997 | Hofmann et al. | |
| 5,703,055 A | 12/1997 | Felgner et al. | |
| 6,068,650 A | 5/2000 | Hofmann et al. | |
| 6,096,020 A | 8/2000 | Hofmann | |
| 6,120,493 A | 9/2000 | Hofmann | |
| 6,150,148 A | 11/2000 | Nanda et al. | |
| 6,181,964 B1 | 1/2001 | Hofmann et al. | |
| 6,192,270 B1 | 2/2001 | Hofmann et al. | |
| 6,207,749 B1 | 3/2001 | Mayes et al. | |
| 6,208,893 B1 | 3/2001 | Hofmann | |
| 6,216,034 B1 | 4/2001 | Hofmann et al. | |
| 6,233,482 B1 | 5/2001 | Hofmann et al. | |
| 6,241,701 B1 | 6/2001 | Hofmann | |
| 6,245,515 B1 | 6/2001 | Vogelstein et al. | |
| 6,296,831 B1 | 10/2001 | Weller et al. | |
| 6,302,874 B1 | 10/2001 | Zhang et al. | |
| 6,623,950 B1 | 9/2003 | Osten et al. | |
| 6,660,247 B1 | 12/2003 | Gutowska et al. | |
| 6,841,617 B2 | 1/2005 | Jeong et al. | |
| 6,852,834 B2 | 2/2005 | Chilkoti | |
| 6,869,588 B2 | 3/2005 | Weller et al. | |
| 7,033,571 B2 | 4/2006 | Gutowska et al. | |
| 7,087,244 B2 | 8/2006 | Jeong et al. | |
| 7,429,458 B2 | 9/2008 | Chilkoti | |
| 7,664,545 B2 | 2/2010 | Westersten et al. | |
| 7,674,882 B2 | 3/2010 | Kaplan et al. | |
| 8,129,330 B2 | 3/2012 | Martinez et al. | |
| 8,283,125 B2 | 10/2012 | Cebolla Ramirez et al. | |
| 8,470,967 B2 | 6/2013 | Chilkoti et al. | |
| 8,497,356 B2 | 7/2013 | Chilkoti et al. | |
| 8,912,310 B2 | 12/2014 | Chilkoti et al. | |
| 9,127,047 B2 | 9/2015 | Chilkoti | |
| 9,592,303 B2 | 3/2017 | Chilkoti et al. | |

(Continued)

FOREIGN PATENT DOCUMENTS

| | | |
|---|---|---|
| CA | 2327325 A1 | 11/1999 |
| CA | 2423488 A1 | 4/2002 |

(Continued)

OTHER PUBLICATIONS

U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017, 2018/0258157, Sep. 13, 2018.
U.S. Appl. No. 62/399,123, filed Sep. 23, 2016.
PCT/US2017/052887, Sep. 22, 2017, WO2018/057847, Mar. 29, 2018.

(Continued)

*Primary Examiner* — Robert S Jones
(74) *Attorney, Agent, or Firm* — Michael Best & Friedrich LLP

(57) ABSTRACT

Disclosed herein are compositions and methods for reducing the antigenicity of molecules. The antigenicity of a molecule may be reduced or eliminated by conjugating at least one branched polymer to the molecule to form a molecule-polymer conjugate. The branched polymer may include a backbone and a plurality of side chains, each side chain covalently attached to the backbone.

21 Claims, 39 Drawing Sheets

Specification includes a Sequence Listing.

(56) References Cited

U.S. PATENT DOCUMENTS

| | | | |
|---|---|---|---|
| 9,771,396 | B2 | 9/2017 | Chilkoti et al. |
| 2002/0052443 | A1 | 5/2002 | Greenwald et al. |
| 2002/0146794 | A1 | 10/2002 | Tomycz |
| 2003/0175290 | A1 | 9/2003 | Renner et al. |
| 2003/0225251 | A1 | 12/2003 | Sallberg et al. |
| 2003/0233675 | A1 | 12/2003 | Cao et al. |
| 2004/0053976 | A1 | 3/2004 | Martinez et al. |
| 2004/0101852 | A1 | 5/2004 | Bennett et al. |
| 2005/0255554 | A1 | 11/2005 | Chilkoti |
| 2005/0288229 | A1 | 12/2005 | Sindrey et al. |
| 2006/0025524 | A1 | 2/2006 | Schneider et al. |
| 2006/0034796 | A1 | 2/2006 | Ashwell et al. |
| 2007/0087114 | A1 | 4/2007 | Chilkoti et al. |
| 2007/0117173 | A1 | 5/2007 | Levison et al. |
| 2008/0181861 | A1 | 7/2008 | Jiang et al. |
| 2009/0098652 | A1 | 4/2009 | Stupp et al. |
| 2010/0015070 | A1 | 1/2010 | Bollschweiler et al. |
| 2010/0048473 | A1 | 2/2010 | Chaikof et al. |
| 2010/0241054 | A1 | 9/2010 | Dacey et al. |
| 2010/0311059 | A1 | 12/2010 | Didion et al. |
| 2010/0325765 | P1 | 12/2010 | Pait et al. |
| 2011/0119778 | A1 | 5/2011 | Liss |
| 2011/0207673 | A1 | 8/2011 | Chilkoti et al. |
| 2011/0294189 | A1* | 12/2011 | Chilkoti .......... C07K 1/02 435/188 |
| 2011/0305718 | A1 | 12/2011 | Mugica et al. |
| 2012/0208742 | A1 | 8/2012 | Primiano et al. |
| 2013/0079277 | A1 | 3/2013 | Chilkoti |
| 2013/0079280 | A1 | 3/2013 | Baca et al. |
| 2013/0096058 | A1 | 4/2013 | Baca et al. |
| 2013/0102993 | A1 | 4/2013 | Kim et al. |
| 2013/0157889 | A1 | 6/2013 | Chilkoti et al. |
| 2013/0165389 | A1 | 6/2013 | Schellenberger et al. |
| 2013/0172274 | A1 | 7/2013 | Chilkoti |
| 2013/0330335 | A1 | 12/2013 | Bremel et al. |
| 2014/0024600 | A1 | 1/2014 | Chilkoti et al. |
| 2014/0163201 | A1 | 6/2014 | Winter et al. |
| 2014/0294932 | A1 | 10/2014 | Kim et al. |
| 2015/0094270 | A1 | 4/2015 | Harris et al. |
| 2015/0112022 | A1 | 4/2015 | Chilkoti et al. |
| 2016/0120952 | A1 | 5/2016 | Chilkoti |
| 2016/0220727 | A1 | 8/2016 | Lu et al. |
| 2016/0271262 | A1 | 9/2016 | Lopez et al. |
| 2016/0303091 | A1 | 10/2016 | Wang |
| 2016/0355802 | A1 | 12/2016 | Isaacs et al. |

FOREIGN PATENT DOCUMENTS

| | | |
|---|---|---|
| WO | WO 2003/040165 A2 | 10/2002 |
| WO | WO 2006/004778 A2 | 1/2006 |
| WO | WO 2007/073486 A2 | 6/2007 |
| WO | WO 2007/108013 A2 | 9/2007 |
| WO | WO 2007/134245 A2 | 11/2007 |
| WO | WO 2009/067584 A1 | 5/2009 |
| WO | WO 2011/123813 A2 | 10/2011 |
| WO | WO 2013/065009 A1 | 5/2013 |
| WO | WO 2014/194244 A1 | 12/2014 |
| WO | WO 2015/130846 A2 | 9/2015 |
| WO | WO 2016/065273 A1 | 4/2016 |
| WO | WO 2016/154530 A1 | 9/2016 |
| WO | WO 2017/015132 A1 | 1/2017 |
| WO | WO 2017/024182 A1 | 2/2017 |
| WO | WO 2017/112825 A2 | 6/2017 |
| WO | WO 2017/112826 A2 | 6/2017 |

OTHER PUBLICATIONS

U.S. Appl. No. 13/942,037, filed Jul. 15, 2015, 2014/0024600, Jan. 23, 2014.
U.S. Appl. No. 16/058,924, filed Aug. 8, 2018.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,540, filed Dec. 21, 2016, 2017/0233714, Aug. 17, 2017.
U.S. Appl. No. 16/064,424, filed Jun. 20, 2018.
U.S. Appl. No. 16/064,425, filed Sep. 12, 2016.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Feb. 14, 2016.
PCT/US2017/051661, Sep. 14, 2017, WO2018/053201, Mar. 22, 2018.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 62/343,245, filed May 31, 2016.
U.S. Appl. No. 62/532,976, filed Jul. 14, 2017.
U.S. Appl. No. 62/532,980, filed Jul. 14, 2017.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2017.
Abbruzzese et al., "A phase I clinical, plasma, and cellular pharmacology study of gemcitabine," J. Clin. Oncol. 1991, 3, 491-498.
Aladini et al., "Chemical Synthesis and Characterization of Elastin-Like Polypeptides (ELPs) With Variable Guest Residues," J Pept Sci, 2016, 22(5):334-342.
Alconcel et al., "FDA-approved poly(ethylene glycol)-protein conjugate drugs," Polym. Chem. 2, 2011, 1442-1448.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, 2012, 13, 2645-2654.
Amiram et al., "A depot-forming glucagon-like peptide-1 fusion protein reduces blood glucose for five days with a single injection," J. Control. Release, 2013, 172, 144-151.
Amiram et al., "Injectable protease-operated depots of glucagon-like peptide-1 provide extended and tunable glucose control," Proc. Natl. Acad. Sci. 110, 2013, 2792-2797.
Antos et al., "Lipid Modification of Proteins through Sortase-Catalyzed Transpeptidation," J. Am. Chem. Soc. 2008, 130, 16338-16343.
Antos et al., "Site-Specific N- and C-Terminal Labeling of a Single Polypeptide Using Sortases of Different Specificity," J. Am. Chem. Soc. 2009, 131, 10800-10801.
Arias et al., "Superior preclinical efficacy of gemcitabine developed as chitosan nanoparticulate system," Biomacromolecules 2011, 12, 97-104.
Armstrong et al., "Antibody against poly(ethylene glycol) adversely affects PEG-asparaginase therapy in acute lymphoblastic leukemia patients," Cancer 110, 2007, 103-111.
Armstrong et al., "The Hydrodynamic Radii of Macromolecules and Their Effect on Red Blood Cell Aggregation," Biophys. J., 2004, 87, 4259-4270.
Arnida et al., "Geometry and surface characteristics of gold nanoparticles influence their biodistribution and uptake by macrophages," Eur J Pharm Biopharm, 2011, 77, 417-423.
Averick et al., "ATRP under biologically relevant conditions: grafting from a protein," ACS Macro. Lett. 1, 2012, 6-10.
Averick et al., "Protein-polymer hybrids: conducting ARGET ATRP from a genetically encoded cleavable ATRP initiator," Eur. Polym. J. 49, 2013, 2919-2924.

(56) References Cited

OTHER PUBLICATIONS

Awai et al., "Studies of the metabolism of I-131-labeled human transferrin," J. Lab. Clin. Med. 61, 1963, 363-396.
Axup et al., "Synthesis of site-specific antibody-drug conjugates using unnatural amino acids," Proc Natl Acad Sci USA, 2012, 109(40):16101-16106.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Banga et al., "Parenteral controlled delivery and parmacokinetics of therapeutic peptides and proteins," (CRC Press, Boca Raton, FL, 2005).
Bansal et al., "PEGylation improves pharmacokinetic profile, liver uptake and efficacy of Interferon gamma in liver fibrosis," J. Control. Release 2011, 154, 233-240.
Bedford et al., "WW domain-mediated interactions reveal a spliceosome-associated protein that binds a third class of proline-rich motif: The proline glycine and methionine-rich motif," PNAS, 1998, 95: 10602-10607.
Bellucci et al., "A noncanonical function of sortase enables site-specific conjugation of small molecules to lysine residues in proteins," Angew. Chem. Int. Ed. 54, 2015, 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, 2013, 52(13):3703-3708.
Bender et al., "Synthesis, Crystallization, and Biological Evaluation of an Orally Active Prodrug of Gemcitabine," J. Med. Chem. 2009, 52, 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, 2010, 142, 312-318.
Bhattacharyya et al., "A paclitaxel-loaded recombinant polypeptide nanoparticle outperforms Abraxane in multiple murine cancer models," Nat. Commun. 2015, 6, 7939.
Bidwell et al., "Development of elastin-like polypeptide for thermally targeted delivery of doxorubicin," Biochemical Pharmacology, 2007, 73(5):620-631.
Boekhorst et al., "Genome-wide detection and analysis of cell wall-bound proteins with LPxTG-like sorting motifs," J. Bacteriol. 187, 2005, 4928-4934.
Bond, "Exenatide (Byetta) as a novel treatment option for type 2 diabetes mellitus," Proc. (Bayl. Univ. Med. Cent.) 19, 2006, 281-284.
Bontempo et al., "Streptavidin as a macroinitiator for polymerization: in situ protein-polymer conjugate formation," J. Am. Chem. Soc., 2005, 6508-6509.
Boyer et al., "Well-Defined Protein-Polymer Conjugates via in Situ RAFT Polymerization," J. Am. Chem. Soc. 2007, 129, 7145-7154.
Broyer et al., "Emerging synthetic approaches for protein-polymer conjugations," Chem. Commun. 2011, 47, 2212.
Brusa et al., "Antitumor activity and pharmacokinetics of liposomes containing lipophilic gemcitabine prodrugs," Anticancer Res. 2007, 27, 195-199.
Cai et al., "Long-acting preparations of exenatide," Drug Des. Dev. Ther. 7, 2013, 963-970.
Caliceti et al., "Pharmacokinetic and biodistribution properties of poly(ethylene glycol)-protein conjugates," Adv. Drug Deliv. Rev, 2003, 55, 1261-1277.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Carrico et al., "Introducing genetically encoded aldehydes into proteins," Nat Chem Biol, 2007, 3(6):321-322.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers to Probe the Mechanism of Elastin Elasticity," J. Am. Chem. Soc., 2009, 132(13):4577-4579.
Chen et al., "Site-specific labeling of cell surface proteins with biophysical probes using biotin ligase," Nat Methods, 2005, 2(2):99-104.
Chilkoti et al., "Design of thermally responsive, recombinant polypeptide carriers for targeted drug delivery," Advance Drug Delivery Reviews, 2002, 54:1093-1111.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, 2006, 6, 662-668.
Chitkara et al., "Self-Assembling, Amphiphilic Polymer-Gemcitabine Conjugate Shows Enhanced Antitumor Efficacy Against Human Pancreatic Adenocarcinoma," Bioconjug. Chem. 2013, 24, 1161-1173.
Cho et al., "Effects of hofmeister anions on the phase transition temperature of elastin-like polypeptides," J. Phys. Chem. B., 2008, 112, 13765-13771.
Cho et al., "Therapeutic nanoparticles for drug delivery in cancer," Clin. Cancer Res., 2008, 14, 1310-1316.
Chow et al., "Peptide-based biopolymers in biomedicine and biotechnology," Mater. Sci. Eng. R Reports, 2008, 62, 125-155.
Chow et al., "Ultra-High Expression of a Thermally Responsive Recombinant Fusion Protein in *E. coli*," Biotechnology Progress, 2006, 22(3):638-646.
Christensen et al., "Fusion order controls expression level and activity of elastin-like polypeptide fusion proteins," Protein Science, 2009, 18:1377-1387.
Coin et al., "Solid-phase peptide synthesis: from standard procedures to the synthesis of difficult sequences," Nat. Protoc., 2007, 2, 3247.
Craik et al., "The future of peptide-based drugs," Chemical biology & drug design 81, 2013, 136-147.
Cui et al., "Amino acid sequence in constitutionally isomeric tetrapeptide amphiphiles dictates architecture of one-dimensional nanostructures," J. Am. Chem. Soc., 2014, 136, 12461-12468.
Cui et al., "Self-assembly of peptide amphiphiles: from molecules to nanostructures to biomaterials," Biopolymers, 2010, 94, 1-18.
Dalla Poza et al., "Targeting gemcitabine containing liposomes to CD44 expressing pancreatic adenocarcinoma cells causes an increase in the antitumoral activity," Biochim. Biophys. Acta, 2013, 1828, 1396-1404.
Dasgupta et al., "Isopeptide Ligation Catalyzed by Quintessential Sortase A: Mechanistic Cues From Cyclic and Branched Oligomers of Indolicidin," The Journal of Biological Chemistry, 2011, vol. 286, No. 27, pp. 23996-24006, Supplemental Information.
De et al., "Temperature-Regulated Activity of Responsive Polymer-Protein Conjugates Prepared by Grafting-from via RAFT Polymerization," J. Am. Chem. Soc. 2008, 130, 11288-11289.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. 2009, 5, 560-569.
Diehl et al., "A Good Practice Guide to the Administration of Substances and Removal of Blood Including Routes and Volumes," J Appl Toxicol, 2001, 21, 15-23.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.

(56) References Cited

OTHER PUBLICATIONS

Dreher et al., "Temperature triggered self-assembly of polypeptides into multivalent spherical micelles," J. Am. Chem. Soc. 2008, 130, 687-694.
Dreher, M. R. PhD. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., 2007, 341, 207-214.
Drucker et al., "The incretin system: glucagon-like peptide-1 receptor agonists and dipeptidyl peptidase-4 inhibitors in type 2 diabetes," Lancet 368, 2006, 1696-1705.
Drucker, "Glucagon-like peptides," Diabetes 47, 1998, 159-169.
Du et al., "Tailor-made dual pH-sensitive polymer-doxorubicin nanoparticles for efficient anticancer drug delivery," J. Am. Chem. Soc., 2011, 133, 17560-17563.
Duan et al., "Fibronectin type III domain based monobody with high activity," Biochemistry, 2007 46(44):12656-12664.
Dubey et al., "Development and evaluation of folate functionalized albumin nanoparticles for targeted delivery of gemcitabine," Int J Pharm., 2015, 492(1-2):80-91.
Duncan, R. "Polymer conjugates as anticancer nanomedicines," Nat. Rev. Cancer 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Eisenhaber et al., "Prediction of lipid posttranslational modifications and localization signals from protein sequences: Big-Π, NMT and PTS1," Nucleic Acids Res., 2003, 31, 3631-3634.
Etrych et al., "HpPMA Copolymer Conjugates of Paclitaxe; and Docetaxel with pH-Controlled Drug Release," Molecular Pharmaceutics, 2010, 7(4):1015-1026.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Feng et al., "Protein resistant surfaces: comparison of acrylate graft polymers bearing oligo-ethylene oxide and phosphorylcholine side chains," Biointerphases, 2006, 1 (1), 50.
Fluegel et al., "Chain stiffness of elastin-like polypeptides," Biomacromolecules 2010, 11, 3216-3218.
Friedman et al., "Directed Evolution to Low Nanomolar Affinity of a Tumor-Targeting Epidermal Growth Factor Receptor-Binding Affibody Molecule," J. Mol. Biol., 2008, 376, 1388-1402.
Furgeson et al., "Structural optimization of a "smart" doxorubicin-polypeptide conjugate for thermally targeted delivery to solid tumors," Journal of Controlled Release, 2006, 110:362-369.
Gaberc-Porekar et al., "Obstacles and pitfalls in the PEGylation of therapeutic proteins," Curr. Opin. Drug Discov. Devel. 11, 2008, 242-250.
Gabizon et al., "Prolonged circulation time and enhanced accumulation in malignant exudates of doxorubicin encapsulated in poly-ethylene-glycol coated liposomes," Cancer Res. 1994, 54, 987-992.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, 2006, R12-R22.
Ganson et al., "Pre-existing anti-PEG antibody linked to first-exposure allergic reactions to Pegnivacogin, a PEGylated RNA aptamer," J. Allergy Clin. Immunology, (2015).
Gao et al., "In situ growth of a PEG-like polymer from the C terminus of an intein fusion protein improves pharmacokinetics and tumor accumulation" PNAS Early Edition, 2010, vol. 107, 1-6.
Gao et al., "In situ growth of a PEG-like polymer from the C terminus of an intein fusion protein improves pharmacokinetics and tumor accumulation," Proc. Natl. Acad. Sci. 107, 2010, 16432-16437.
Gao et al., "In situ growth of a stoichiometric PEG-like conjugate at a protein's N-terminus with significantly improved pharmacokinetics," Proc. Natl. Acad. Sci., 2009,15231-15236.
Garanger et al., "Structural Evolution of a Stimulus-Responsive Diblock Polypeptide Micelle by Temperature Tunable Compaction of its Core," Macromolecules, 2015, 48, 6617-6627.
Garay et al., "Antibodies against polyethylene glycol in healthy subjects and inpatients treated with PEG-conjugated agents," Expert Opinion. Drug Deliv. 9, 2012, 1319-1323.
Gauthier et al., "Peptide/protein-polymer conjugates: synthetic strategies and design concepts," Chem. Commun., 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (2017).
Gibson et al., "Enzymatic assembly of DNA molecules up to several hundred kilobases," Nat Methods, 2009, 6, 343-345.
Gluck et al., "Single Vector System for Efficient N-myristoylation of Recombinant Proteins in *E. coli*," Plos One. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gordon et al., "Protein N-myristoylation," J. Biol. Chem., 1991, 266, 8647-8650.
Goutelle et al., "The Hill equation: a review of its capabilities in pharmacological modelling. Fundam," Clin. Pharmacol. 22, 2008, 633-648.
Green et al., "Novel dipeptidyl peptidase IC resistant analogues of glucagon-like peptide-1(7-36)amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., 2006, 1(6):2876-90.
Grover et al., "Protein-Polymer Conjugates: Synthetic Approaches by Controlled Radical Polymerizations & Interesting Applications", Curr Opin Chem Bioi., Dec. 2010; 14(6): 818-827.
Haider et al., "Genetically engineered polymers: Status and prospects for controlled release," J. Control. Release, 2004, 95, 1-26.
Hamidi et al., "Pharmacokinetic Consequences of Pegylation," Drug Deliv. 2006, 13, 399-409.
Hamley, "Self-assembly of amphiphilic peptides," Soft Matter, 2011, 7, 4122.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, 2015, 48, 4183-4195.
Hassouneh et al., "Elastin-Like Polypeptides as a Purification Tag for Recombinant Proteins," Curr Protoc Protein Sci., 2010, Chapter 6. Unit 6.11. 10.1002/0471140864.ps0611s61.
Hassouneh et al., "Fusions of elastin-like polypeptides to pharmaceutical proteins," Methods Enzymol., 2012, 502, 215-37.
Hassouneh et al., "Unexpected Multivalent Display of Proteins by Temperature Triggered Self-assembly of Elastin-like Polypeptide Block Copolymers," Biomacromolecules, 2012, vol. 13, Issue 4, pp. 1598-1605.
He et al., "Comparative genomics of elastin: Sequence analysis of a highly repetitive protein," Matrix Biology, 2007, 26:524-540.
He et al., "Improving protein resistance of α-Al2O3 membranes by modification with POEGMA brushes," Applied Surface Science, 2011, 258 (3), 1038-1044.
Heagerty et al., Biometrics, "Time-dependent ROC curves for censored survival data and a diagnostic marker," 2000, 56(2):337-44.
Heal et al., "N-Myristoyl transferase-mediated protein labelling in vivo," Org. Biomol. Cham., 2008, 6(13):2308-2315.

(56) References Cited

OTHER PUBLICATIONS

Heal et al., "Site-specific N-terminal labelling of proteins in vitro and in vivo using N-myristoyl transferase and bioorthogonal ligation chemistry," Chem. Commun., 2008, 3, 480-482.
Heredia et al., "In Situ Preparation of Protein-"Smart" Polymer Conjugates with Retention of Bioactivity," J. Am. Chem. Soc. 2005, 127, 16955-16960.
Hershfield et al., "Induced and pre-existing anti-polyethylene glycol antibody in a trial of every 3-week dosing of pegloticase for refractory gout, including in organ transplant recipients," Arthritis Res. Ther. 16, 2014, R63.
Ho et al., "Chemoenzymatic Labeling of Proteins for Imaging in Bacterial Cells," J. Am. Chem. Soc., 2016, 138(46):15098-15101.
Hober et al., "Protein A chromatography for antibody purification," Journal of Chromatography B 848, 2007, pp. 40-47.
Hochkoeppler, "Expanding the landscape of recombinant protein production in *Escherichia coli*," Biotechnol. Lett., 2013, 35, 1971-1981.
Holehouse et al., "CIDER: Classification of Intrinsically Disordered Ensemble Regions," Biophysical Journal, 2015, vol. 108, Issue 2, Supplement 1, p. 228a.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., 2015, 7, 1-8.
Ishida et al., "Accelerated blood clearance (ABC) phenomenon upon repeated injection of PEGylated liposomes," International Journal of Pharmaceutics, 2008, 354(1-2):56-62.
Jakubowski et al., "Activators regenerated by electron transfer for atom-transfer radical polymerization of (meth)acrylates and related block copolymers," Angew. Chem. Int. Ed., 2006, 4482-4486.
Janes et al., "Chitosan nanoparticles as delivery systems for doxorubicin," J. Control Release, 2001, 73, 255-267.
Jia et al., "Preparation, physicochemical characterization and cytotoxicity in vitro of gemcitabine-loaded PEG-PDLLA nanovesicles," World J. Gastroenterol. 2010, 16(8):1008-1013.
Jiang et al., "The internal structure of self-assembled peptide amphiphiles nanofibers," Soft Matter, 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, 2009, 70 (1), 53-9.
Junutula et al., "Site-specific conjugation of a cytotoxic drug to an antibody improves the therapeutic index," Nat Biotechnol, 2008, 26(8):925-932.
Kanoski et al., "The role of nausea in food intake and body weight suppression by peripheral GLP-1 receptor agonists, exendin-4 and liraglutide," Neuropharmacology 62, 2012, 1916-1927.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, 2012, 4(1):59-63.
Keller et al., "Empirical Statistical Model to Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Khandare et al., "Polymer-drug conjugates: Progress in polymeric drugs," Prog. Polym. Sci., 2005, vol. 31, pp. 359-397.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem. 2012, 23, 2214-2220.

Kim et al., "Ultrasensitive Carbon nanotube-based biosensors using antibody-binding fragments," Analytical Biochemistry, 2008, 381, 193-198.
Knop et al., "Poly(ethylene glycol) in Drug Delivery: Pros and Cons as Well as Potential Alternatives," Angewandte Chemie International Edition, 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-Invisible Solubility Enhancement Tag Using a Sortase-Mediated Protein Ligation Method," J Biomol NMR. Mar. 2009, vol. 43, No. 3; pp. 145-150.
Kontos et al., "Drug development: longer-lived proteins," Chemical Society Reviews, 2012, 41(7):2686-2695.
Kothare et al., "Pharmacokinetics, pharmacodynamics, tolerability, and safety of exenatide in Japanese patients with type 2 diabetes mellitus," J. Clin. Pharmacol. 48, 2008, 1389-1399.
Kramer et al., "Quantitative Side-Chain Modifications of Methionine-Containing Elastin-Like Polypeptides as a Versatile Tool to Tune Their Properties," ACS Macro Lett., 2015, 4(11):1283-1286.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., 2015, 26(10):2153-2160.
Kulkarni et al., "Selective functionalization of the protein N terminus with N-myristoyl transferase for bioconjugation in cell lysate," ChemBioChem, 2013, 14, 1958-1962.
Kumar et al., "N-Terminal Region of the Catalytic Domain of Human N-Myristoyltransferase 1 Acts as an Inhibitory Module," PLoS One, 2015, 10(5):e0127661.
Kyte et al., "A Simple Method for Displaying the Hydropathic Character of a Protein," J. Mol. Biol., 1982, 157:105-132.
Langer et al., "Designing materials for biology and medicine," Nature, 2004, 428, 487-92.
Le Droumaguet et al., "Recent advances in the design of bioconjugates from controlled/living radical polymerization," Polym. Chem. 2010, 1, 563-598.
Le Meins et al., "Hybrid polymer/lipid vesicles: State of the art and future perspectives," Mater. Today, 2013, 16, 397-402.
Leader et al., "Protein therapeutics: a summary and pharmacological clasification," Nat. Rev. Drug Discov. 7, 2008, 21-39.
Lee et al., "Atomistic molecular dynamics simulations of peptide amphiphile self-assembly into cylindrical nanofibers," J. Am. Chem. Soc., 2011, 133, 3677-3683.
Lee et al., "Theranostic nanoparticles with controlled release of gemcitabine for targeted therapy and MRI of pancreatic cancer," ACS Nano 2013, 7(3):2078-2089.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., 2011, 77(22):8114-28.
Leung et al., "Bio-Click Chemistry: Enzymatic Functionalization of PEGylated Capsules for Targeting Applications**," Angew. Chem. Int. Ed. 2012, 51, 7132-7136.
LeVine et al., "Thioflavine T interaction with synthetic Alzheimer's disease beta-amyloid peptides: detection of amyloid aggregation in solution," Protein Sci., 1993, 2, 404-10.
Li et al., "Molecular description of the lcst behavior of an elastin-like polypeptide," Biomacromolecules, 2014, 15, 3522-3530.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., 2015, 36(1):90-95.
Liao et al., "Removal of N-terminal methionine from recombinant proteins by engineered *E. coli* methionine aminopeptidase," Prot. Sci. 13, 2004, 1802-1810.

(56) References Cited

OTHER PUBLICATIONS

Liechty et al., "Polymers for Drug Delivery Systems," Annual review of chemical and biomolecular engineering, 2010, 1:149-173.
Lim et al., "Improved Non-Chromatographic Purification of a Recombinant Protein by Cationic Elastin-like Polypeptides" Biomacromolecules, 2007, 8(5): 1417-1424.
Lim et al., "In situ cross-linking of elastin-like polypeptide block copolymers for tissue repair," Biomacromolecules, 2008, 9, 222-230.
Lim et al., "In vivo post-translational modifications of recombinant mussel adhesive protein in insect cells," Biotechnol. Prog., 2011, 27, 1390-1396.
Linder et al., "Lipid Modifications of G Protein Subunits," J. Biol. Chem., 1991, 266(7):4654-4659.
Ling et al., "Protein thioester synthesis enabled by sortase," J. Am Chem Soc, 2012, 134(26):10749-10752.
Liu et al., "Hydrophobic modifications of cationic polymers for gene delivery," Prog. In Polym. Sci., 2010, 35, 1144-1162.
Liu et al., "In Situ Formation of Protein-Polymer Conjugates through Reversible Addition Fragmentation Chain Transfer Polymerization**," Angew. Chem. Int. Ed. 2007, 46, 3099-3103.
Liu et al., "Injectable intratumoral depot of thermally responsive polypeptide-radionuclide conjugates delays tumor progression in a mouse model," J. Control Release, 2010, 144(1):2-9.
Livingstone, "Theoretical property predictions. Curr Top Med Chem Field Full Journal Title: Current topics in medicinal chemistry," Curr. Top. Med. Chem. 2003, 3, 1171-1192.
Lovshin et al., "Incretin-based therapies for type 2 diabetes mellitus," Nat. Rev. Endocrinol. 5, 2009, 262-269.
Luginbuhl et al., "One-week glucose control via zero-order release kinetics from an injectable depot of glucagon-like peptide-1 fused to a thermosensitive biopolymer," Nat. Biomed. Eng., 2017, 1, 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., 2017, 56: 13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lund et al., "Phase II study of gemcitabine (2',2'-difluorodeoxycytidine) in previously treated ovarian cancer patients," J. Natl. Cancer. Inst. 1994, 86(20):1530-1533.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir : the ACS journal of surfaces and colloids, 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, 2006, 16 (5), 640-648.
MacEwan et al., "Digital switching of local arginine density in a genetically encoded self-assembled polypeptide nanoparticle controls cellular uptake," Nano Lett., 2012, 12, 3322-3328.
MacEwan et al., "Elastin-like polypeptides: Biomedical applications of tunable biopolymers," Biopolymers, 2010, 94, 60-77.
MacEwan et al., "Non-chromatographic Purification of Recombinant Elastin-like Polypeptides and their Fusions with Peptides and Proteins from *Escherichia coli*," 2014, 88, p. e51583.
MacEwan et al., "Phase Behavior and Self-Assembly of Perfectly Sequence-Defined and Monodisperse Multiblock Copolypeptides," Biomacromolecules, 2017, 18(2):599-609.
Mack et al., "Antiobesity action of peripheral exenatide (exendin-4) in rodents: effects on food intake, body weight, metabolic status and side-effect measures," Int. J. Obes. 30, 2006, 1332-1340.
MacKay et al., "Self-assembling chimeric polypeptide-doxorubicin conjugate nanoparticles the abolish tumors after single injection," Nat Mater, 2009, 8(12):993-999.

Maeda et al., "Tumor vascular permeability and the EPR effect in macromolecular therapeutics: a review," J. Control. Release, 2000, 65(1-2)271-284.
Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, 2010, 671-678.
Malik et al., "Recent advances in protein and peptide drug delivery systems," Curr. Drug Deliv. 2, 2007, 141-151.
Mann et al., "Proteomic analysis of post-translational modifications," Nat. Biotechnol., 2003, 21, 255-61.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, 2006, 70(1):192-221.
Marr et al., "Effect of Temperature on the Composition of Fatty Acids in *Escherichia coli*," J Bacteriol., 1962, 84(6):1260-7.
Maskarinec et al., "Protein engineering approaches to biomaterials design," Curr. Opin. Biotechnol., 2005, 16, 422-426.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, 2015, 208:52-8.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matyjaszewski et al., "Atom transfer radical polymerization," Chem. Rev. 101, 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McDaniel et al., "A unified model for de novo design of elastin-like polypeptides with tunable inverse transition temperatures," Biomacromolecules, 2013, 14(8):2866-2872.
McDaniel et al., "Drug delivery to solid tumors by elastin-like polypeptides," Adc. Drug Deliver. Rev., 2010, 62(15):1456-1467.
McDaniel et al., "Noncanonical Self-Assembly of Highly Asymmetric Genetically Encoded Polypeptide Amphiphiles into Cylindrical Micelles," Nano Lett., 2014, 14(11):6590-6598.
McDaniel et al., "Self-assembly of thermally responsive nanoparticles of a genetically encoded peptide polymer by drug conjugation," Chem. Int. Ed. 2013, 52, 1683-1687.
McDaniel, J.R. et al., "Recursive Directional Ligation by Plasmid Reconstruction Allows Rapid and Seamless Cloning of Oligomeric Genes," Biomacromolecules, 2010, 11(4):944-952.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
Mejuch et al., "Synthesis of lipidated proteins," Bioconjug. Chem. 27, 2016, 1771-1783.

(56) References Cited

OTHER PUBLICATIONS

Mero et al., "Transglutaminase-mediated PEGylation of proteins: direct identification of the sites protein medification by mass spectrometry using a novel monodisperse PEG," Bioconjug Chem, 2009, 20(2):384-389.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Mosbach et al., "Formation of proinsulin by immobilized Bacillus subtilis," Nature, 1983, 302, 543-545.
Muiznies et al., "Modulated growth, stability and interactions of liquid-like coacervate assemblies of elastin," Matrix Biology 36, 2014, pp. 39-50.
Muralidharan et al., "Protein Ligation: an Enabling Technology for the Biophysical Analysis of Proteins," Nature Methods, 2006, vol. 3, No. 6, pp. 429-438.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials 2014, 35(24):6482-6497.
Nairn et al., "A Synthetic Resilin Is Largely Unstructured," Biophysical Journal, 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Neidigh et al., "Exendin-4 and glucagon-like-peptide-q: NMR structural comparisons in the solution and micelle-associated states," Biochemistry 40, 2001, 13188-13200.
Newcomb et al., "Advances in cryogenic transmission electron microscopy for the characterization of dynamic self-assembling nanostructures," Current Opinion in Colloid and Interface Science, 2012, 17, 350-359.
Nicolas et al., "Fluorescently tagged polymer bioconjugates from protein derived macroinitiators," Chem. Commun. 2006, 45, 4697-4699.
Nielsen, "Incretin mimetics and DPP-IV inhibitors for the treatment of type 2 diabetes," Drug Discov. Today 10, 2005, 703-710.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, 2008, 9, 2755-2763.
O'Day et al., "Therapeutic Protein-polymer Conjugates: Advancing beyond PEGylation," J. Am. Chem. Soc., 2014, vol. 136, pp. 14323-14332.
Ortony et al., "Internal dynamics of a supramolecular nanofibre," Nat. Mater., 2014, 13, 1-5.
Pace et al., "How to measure and predict the molar absorption coefficient of a protein" Protein Science 1995, 4: 2411-2423.
Palva et al., "Secretion of interferon by Bacillus subtilis," Gene, 1983, 22, 229-235.
Paolino et al., "Folate-targeted supramolecular vesicular aggregates as a new frontier for effective anticancer treatment in in vivo model," Eur. J. Pharm. Biopharm. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release 2010, 144(2):144-150.
Papa et al., "PEGylated Liposomal Gemcitabine: Insights Into a Potential Breast Cancer Therapeutic," Cell Oncol. (Dordr) 2013, 36(6):449-457.
Paramonov et al., "Self-assembly of peptide-amphiphile nanofibers: The roles of hydrogen bonding and amphiphilic packing," J. Am. Chem. Soc., 2006, 128, 7291-7298.
Park et al., "Formulation optimization and in vivo proof-of-concept study of thermosensitive liposomes balanced by phospholipid, elastin-like polypeptide, and cholesterol," PLoS One, 2014, 9: e103116, 13 pages.
Parkes et al. "Discovery and development of exenatide: the first antidiabetic agent to leverage the multiple benefits of the incretin hormone, GLP-1," Expert Opinion. Drug Deliv. 8, 2012, 219-244.
Parveen et al., "Nanomedicine," Clinical Pharmacokinetics, 2006, 45(10):965-988.
Peeler et al., "Genetically encoded initiator for polymer growth from proteins," J. Am. Chem. Soc. 132, 2010, 13575-13577.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., 2017, 28(5):1403-1412.
Pinkas et al., "Tunable, post-translational hydroxylation of collagen domains in *Escherichia coli*," ACS Chem. Biol., 2011, 6, 320-324.
Popp et al., "Site-specific labeling via sortase-mediated transpeptidation," Curr. Protoc. Protein Sci. 56, 2009, 15.13.1-15.13.9.
Popp et al., "Sortase-Catalyzed Transformations That Improve the Properties of Cytokines," PNAS, 2011, vol. 108, No. 8, pp. 3169-3174.
Pulaski et al., "Mouse 4T1 breast tumor model," Curr. Protoc. Immunol., 2001, Chapter 20, Unit 20.2.
Qi et al., Dataset for a brush-polymer conjugate of exendin-4 reduces blood glucose for up to five days and eliminates poly(ethylene glycol) antigenicity. Figshare, 2016, <http://dx.doi.org/10.6084/m9.figshare.3976761> 28 pages.
Qi et al., "Growing polymers from peptides and proteins: a biomedical perspective," Polym. Chem. 5, 2014, 266-276.
Qi et al., "Protein-polymer conjugation—moving beyond PEGylation," Curr. Opin. Chem. Biol. 28, 2015, 181-193.
Qi et al., "Sortase-catalyzed initiator attachment enables high yield growth of a stealth polymer from the C terminus of a protein," Macromol. Rapid Commun. 34, 2013, 1256-1260.
Qiu et al., "Polymer Architecture and Drug Delivery," Pharmaceutical Research, 2006, 23(1):1-30.
Quiroz et al., "Sequence heuristics to encode phase behaviour in intrinsically disordered protein polymers," Nat. Mater., 2015, 14, 1164-1171.
Radivojac et al., "Intrinsic Disorder and Functional Proteomics," Biophysical Journal, 2007, vol. 92, Issue 5, pp. 1439-1456.
Rapaka et al., "Coacervation of Sequential Polypeptide Models of Tropoelastin," Int J Peptide Protein Res, 1978, 11: 97-108.
Rauscher et al. "Proline and Glycine Control Protein Self-Organization into Elastomeric or Amyloid Fibrils," Structure, 2006, 14:1667-1676.
Richards et al., "Engineered fibronectin type III domain with a RGDWE sequence binds with enhanced affinity and specificity to human αvβ3 integrin," J Mol Biol, 2003, 326(5):1475-1488.
Riddles et al., "Ellman's reagent: 5,5'-dithiobis(2-nitrobenzoic acid)—a reexamination," Anal Biochem. 1979, 94(1):75-81.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., 2015, 589, 2477-2486.

(56) References Cited

OTHER PUBLICATIONS

Robinet et al. "Elastin-derived peptides enhance angiogenesis by promoting endothelial cell migration and tubulogenesis through upregulation of MT1-MMP," J. Cell Science, 2005, 118:343-356.
Römer et al., "The elaborate structure of spider silk: structure and function of a natural high performance fiber," Prion 2, 2008, 154-161.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Saifer et al., "Selectivity of binding of PEGs and PEG-like oligomers to anti-PEG antibodies induced by methoxyPEG-proteins," Molecular Immunology 57, 2014, 236-246.
Sandler et al., "Gemcitabine: Single-Agent and Combination Therapy in Non-Small Cell Lung Cancer," Oncologist 1999, 4(3)241-251.
Schellenberger et al., "A recombinant polypeptide extends the in vivo half-life of peptides and proteins in a tunable manner," Nat. Biotechnol. 27, 2009, 1186-1188.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., 2007, 93, 2429-2435.
Shen et al., "Conjugation site modulates the in vivo stability and thearpeutic activity of antibody-drug conjugates," Nat Biotechnol, 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, 2009, 10:1955-1961.
Sherman et al., "Next-Generation PEGylation Enables Reduced Immunoreactivity of PEG-Protein Conjugates," Drug and Development & Delivery, 2012, vol. 12, No. 5, 36-42.
Sherman et al., "Role of the Methoxy Group in Immune Responses to mPEG-Protein Conjugates," Bioconjugate Chemistry, 2012, 23, 485-499.
Shi et al., "Cell adhesion on a POEGMA-modified topographical surface," Langmuir: the ACS journal of surfaces and colloids, 2012, 28 (49), 17011-8.
Shimoboji et al., "Temperature-Induced Switching of Enzyme Activity with Smart Polymer-Enzyme Conjugates," Bioconjugate Chem. 2003, 14, 517-525.
Siegwart et al., "ATRP in the Design of Functional Materials for Biomedical Applications," Prog Polymer Science, 2012, vol. 37, No. 1, pp. 18-37.
Silva et al., "Selective differentiation of neural progenitor cells by high-epitope density nanofibers," Science, 2004, 303, 1352-5.
Simakova et al., "Aqueous ARGET ATRP," Macromolecules 45, 2012, 6371-6379.
Sorkin et al., "Signal transduction and endocytosis: close encounters of many kinds," Nat Rev Mol Cell Biol, 2002, 3(8):600-614.
Stefl et al., "RNA sequence-and shape-dependent recognition by proteins in the ribonucleoprotein particle" EMBO reports (2005) 6(1):33-38.
Sumerlin, "Proteins as Initiators of Controlled Radical Polymerization: Grafting-from via ATRP and RAFT," ACS Macro Lett. 2012, 1, 141-145.
Surwit et al., Diet-induced type II diabetes in C57BL/6J mice, Diabetes 37, 1988, 1163-1167.
Swee et al., "Sortase-mediated modification of αDEC205 affords optimization of antigen presentation and immunization against a set of viral epitopes," Proc Natl Acad Sci USA, 2013, 110(4):1428-1433.

Swers et al., Multivalent Scaffold Proteins as Superagonists of TRAIL Receptor 2-Induced Apoptosis, Mol Cancer Ther, 2013, 12, 1235-1244.
Tang et al., "Combinatorial codon scrambling enables scalable gene synthesis and amplification of repetitive proteins," Nature Mater., 2016, 15, 419-424.
Tantakitti et al., "Energy landscapes and functions of supramolecular systems," Nat. Mater., 2016, 15, 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, 2012, 3 (10), 2743-2751.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tong et al., "Protein Modification with Amphiphilic Block Copoly(2-oxazoline)s as a New Plataform for Enhanced Cellular Delivery," Mol. Pharm., 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptidase that cleaves surface proteins of Staphylococcus aureus and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Expression and purification of recombinant proteins from Escherichia coli: Comparison of an elastin-like polypeptide fusion with an oligohistidine fusion" Protein Science, 2004, 13: 3274-3284.
Triola et al., "Chemical biology of lipidated proteins," ACS Chemical Biology, 2012, 7, 87-99.
Troyanskaya et al., "Nonparametric methods for identifying differentially expressed genes in microarray data," Bioinformatics, 2002, 18(11):1454-61.
Tsarevsky et al., "Deactivation efficiency and degree of control over polymerization in ATRP in protic solvents," Macromolecules 37, 2004, 9768-9778.
Tsume et al., "The development of orally administrable gemcitabine prodrugs with D-enantiomer amino acids: Enhanced membrane permeability and enzymatic stability," Eur. J. Pharm. Biopharm. 2014, 86(3):514-523.
Turunen et al., "Paclitaxel Succinate Analogs: Anionic Introduction as a Strategy to Impart Blood Brain Barrier Permeability," Bioorg Med Chem Lett, 2008, 18(22):5971-5974.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B.,1997, 101, 11007-11028.
Urry et al., "Temperature of polypeptide inverse temperature transition depends on mean residue hydrophobicity," J. Am. Chem. Soc., 1991, 113(11):4346-4348.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.

(56) References Cited

OTHER PUBLICATIONS

Viegas et al., "Polyoxazoline: Chemistry, properties and applications," Bioconjugate Chem., 2011, vol. 22, pp. 976-986.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Vrignaud et al., "Strategies for the nanoencapsulation of hydrophilic molecules in polymer-based nanoparticles," Biomaterials 2011, 32(33):8593-8604.
Walczak, "Death Receptor—Ligand Systems in Cancer, Cell Death, and Inflammation," Cold Spring Harb. Perspect. Biol., 2013, 5, a008698.
Walsh et al., "Post-translational modifications in the context of therapeutic proteins," Nat. Biotechnol., 2006, 24, 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "Enhanced Tumor Delivery of Gemcitabine via PEG-DSPE/TPGS Mixed Micelles," Mol. Pharm. 2014, 11, 1140-1150.
Wendt et al., "DNA-mediated Folding and Assembly of MyoD-E47 Heterodimers," Journal of Biol. Chem., 1998, 273(10):5735-5743.
Werle et al., "Strategies to improve plasma half life time of peptide and protein drugs," Amino Acids 30, 2006, 351-367.
Wienkers et al., "Predicting in vivo drug interactions from in vitro drug discovery data," Nat. Rev. Drug. Discov. 2005, 4(10):825-833.
Williamson et al., "Efficient N-terminal labeling of proteins by use of sortase," Angew Chem Int ed Engl, 2012, 51(37):9377-9380.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wu et al., "Site-specific chemical modification of recombinant proteins produced in mammalian cells by using the genetically encoded aldehyde tag," Proc Natl Acad Sci USA, 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Xavier et al., "HPLC Method for the Dosage of Paclitaxel in Copaiba Oil: Development, Validation, Application to the Determination of the Solubility and Partition Coefficients," Chromatographia, 2016, 79, 405-412.
Xu et al., "A quality by design (QbD) case study on liposomes containing hydrophilic API: II. Screening of critical variables, and establishment of design space at laboratory scale," Int. J. Pharm. 2012, 423(2):543-553.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Self-assembly behavior of peptide amphiphiles (PAs) with different length of hydrophobic alkyl tails," Colloids Surfaces B Biointerfaces, 2010, 81, 329-335.
Yang et al., "Poly(carboxybetaine) nanomaterials enable long circulation and prevent polymer-specific antibody production," Nano Today, 2014, 9(1):10-16.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release 117, 2007, 371-379.
Zhang et al., "A self-assembly pathway to aligned monodomain gels," Nat. Mater., 2010, 9, 594-601.
Zhang et al., "Nanoparticles in medicine: therapeutic applications and developments," Clin. Pharmacol. Ther. 2008, 83(5):761-769.
Zhang et al., "Shape Effects of Nanoparticles Conjugated with Cell-Penetrating Peptides (HIV Tat PTD) on CHO Cell Uptake," Bioconjugate Chem, 2008, 19(9):1880-1887.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zong et al., "Crystal structures of *Staphylococcus aureus* sortase A and its substrate complex," J. Biol. Chem. 279, 2004, 31383-31389.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,540 dated Sep. 27, 2018 (12 pages).
AACR, "AACR Cancer Progress Report 2016," Clin Cancer Res, 2016, 22, 143 pages.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, 2009, 90, 67-74.
Adamska et al., "Pancreatic ductal adenocarcinoma: Current and evolving therapies," J Mol Sci, 2017, 18, 1338-1380.
Adiseshaiah et al., "Nanomedicine strategies to overcome the pathophysiological barriers of pancreatic cancer," Nat Rev Clin Oncol, 2016, 13, 750-765.

(56) References Cited

OTHER PUBLICATIONS

Albanese et al., "The effect of nanoparticle size, shape, and surface chemistry on biological systems," Annu. Rev. Biomed. Eng., 2012, 14, 1-16.
Andersen et al., "Extending Half-life by Indirect Targeting of the Neonatal Fc Receptor (FcRn) Using a Minimal Albumin Binding Domain," Journal of Biological Chemistry, 2011, 286(7): p. 5234-5241.
Asai et al., "Protein polymer hydrogels by in situ, rapid and reversible self-gelation," Biomaterials, 2012, 33, 5451-5458.
Atun et al., "Expanding global access to radiotherapy," Lancet Oncol, 2015, 16, 1153-1186.
Awasthi et al., "Comparative benefits of Nab-paclitaxel over gemcitabine or polysorbate-based docetaxel in experimental pancreatic cancer," Carcinogenesis, 2013, 34, 2361-2369.
Awasthi et al., "Evaluation of combination treatment benefits of nab-paclitaxel in experimental pancreatic cancer," Journal of Clinical Oncology, 2012, 30, 170.
Azhdarinia et al., "Regional radiochemotherapy using in situ hydrogel," Pharm Res., 2005, 22, 776-783.
Bache et al., "Investigating the accuracy of microstereotactic-body-radiotherapy utilizing anatomically accurate 3D printed rodent-morphic dosimeters," Medical Physics, 2015, 42, 846-855.
Bailey et al., "Genomic analyses identify molecular subtypes of pancreatic cancer," Nature, 2016, 531, 47-52.
Bamford et al., "The COSMIC (Catalogue of Somatic Mutations in Cancer) database and website," British Journal of Cancer, 2004, 91, 355-358.
Barbuti et al., "Paclitaxel through the ages of anticancer therapy: Exploring its role in chemoresistance and radiation therapy," Cancers, 2015, 7, 2360-2371.
Barnett et al., "Normal tissue reactions to radiotherapy: towards tailoring treatment dose by genotype," Nat Rev Cancer, 2009, 9, 134-142.
Barton et al., "Estimating the demand for radiotherapy form the evidence: A review of changes from 2003 to 2012," Radiother Oncol, 2014, 112, 140-144.
Baskar et al., "Cancer and Radiation Therapy: Current Advances and Future Directions," Int. J. Med. Sci., 2012, 9, 193-199.
Begg et al., "Strategies to improve radiotherapy with targeted drugs," Nat Rev Cancer, 2011, 11, 239-253.
Bernacki et al., "Length-dependent aggregation of uninterrupted polyalanine peptides," Biochemistry, 2011, 50, 9200-9211.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et at, "Microtubule stabilising agents and ionising radiation: Multiple exploitable mechanisms for combined treatment," Eur J Cancer, 2013, 49, 245-253.
Bocci et al., "The pharmacological bases of the antiangiogenic activity of paclitaxel," Angiogenesis, 2013, 16, 481-492.
Bochicchio et al., "Investigating by CD the molecular mechanism of elasticity of elastomeric proteins," Chirality, 2008, 20, 985-994.
Boldt, "Use of albumin: an update," Br J. Anaesth., 2010, 104 (3), 276-284.
Branco et al., "Self-assembling materials for therapeutic delivery," Acta Biomaterialia, 2009, 5(3): p. 817-831.
Burchard, "Light Scattering Techniques," Physical techniques for the study of food biopolymers, 1994, 151-213.
Burnouf, "Modern plasma fractionation," Transfus. Med. Rev., 2007, 21 (2), 101-117.

Cabral et al., "Accumulation of sub-100 nm polymeric micelles in poorly permeable tumours depends on size," Nature Nanotechnology, 2011, 6, 815-823.
Callahan et al., "Triple stimulus-responsive polypeptide nanoparticles that enhance intratumoral spatial distribution," Nano Letters, 2012, 12, 2165-2170.
Camilloni et al., "Determination of secondary structure populations in disordered states of proteins using nuclear magnetic resonance chemical shifts," Biochemistry, 2012, 51, 2224-2231.
Cao et al., "Monitoring the effects of anti-angiogenesis on the radiation sensitivity of pancreatic cancer xenografts using dynamic contrast-enhanced computed tomography," Int J Radiation Oncol Biol Phys, 2014, 88, 412-418.
Cardenes et al., "Locally advanced pancreatic cancer: Current therapeutic approach," The Oncologist, 2006, 11, 612-623.
Cataldo et al., "Radiation-induced crosslinking of collagen gelatin into a stable hydrogel," Journal of Radioanalytical and Nuclear Chemistry, 2008, 275, 125-131.
Ceska et al., "A new and rapid method for the clinical determination of $\alpha$-amylase activities in human serum and urine. Optimal conditions," Clinica Chimica Acta, 1969, 26, 437-444.
Chakrabartty et al., "Stability of $\alpha$-Helices," Adv Protein Chem, 1995, 46, 141-176.
Chang et al., "Tumor-stroma interaction in orthotopic primary pancreatic cancer xenografts during hedgehog pathway inhibition," Int. J. Cancer, 2013, 133, 225-235.
Chaudhury et al., "The major histocompatibility complex-related Fc receptor for IgG (FcRn) binds albumin and prolongs its lifespan," J Exp Med, 2003, 197(3): p. 315-22.
Chen et al., "Anisotropic hydrogels fabricated with directional freezing and radiation-induced polymerization and crosslinking method," Materials Letters, 2012, 89, 104-107.
Chen et al., "Rheology of Soft Materials," Annual Review of Condensed Matter Physics, 2010, 1, 301-322.
Chen et al., "The use of self-adjuvanting nanofiber vaccines to elicit high-affinity B cell responses to peptide antigens without inflammation," Biomaterials 34, 2013, 8776-8785.
Cho et al., "Hydrogen bonding of $\beta$-turn structure is stabilized in D(2)O," J Am Chem Soc, 2009, 131, 15188-15193.
Choi et al., "Renal Clearance of Nanoparticles," Nature biotechnology, 2007, 25(10): p. 1165-1170.
Choy et al., "Investigation of taxol as a potential radiation sensitizer," Cancer, 1993, 71, 3774-3778.
Christensen et al., "Predicting Transition Temperatures of Elastin-Like Polypeptide Fusion Proteins," Biomacromolecules, 2013, 14(5): p. 1514-1519.
Cid-Arregui et al., "Perspectives in the treatment of pancreatic adenocarcinoma," World Journal of Gastroenterology, 2015, 21, 9297-9316.
Ciezki et al., "Brachytherapy or surgery? A composite view," Oncology, 2009, 23, 960-964.
Cima, "AVMA Guidelines for the Euthanasia of Animal: 2013 Edition," Journal of the American Veterinary Medical Association, 2013, 242, 102 pages.
Cirulis et al., "Viscoelastic properties and gelation of an elastin-like polypeptide," Journal of Rheology, 2009, 53, 1215-1228.
Clarke et al., "Tropoelastin massively associates during coacervation to form quantized protein spheres," Biochemistry, 2006, 45, 9989-9996.
Clavé et al., "Amylase, lipase, pancreatic isoamylase, and phospholipase A in diagnosis of acute pancreatitis," Clinical Chemistry, 1995, 41, 1129-1134.
Colomb et al., "Radiation-Convertible Polymers from Norbornenyl Derivatives. Crosslinking with Ionizing Radiation," Journal of Applied Polymer Science, 1970, 14, 1659-1670.
Conrad et al., "ELPylated anti-human TNF therapeutic single-domain antibodies for prevention of lethal septic shock," Plant Biotechnology Journal, 2011, 9, 22-31.
Darzynkiewicz et al., "DNA content measurement for DNA ploidy and cell cycle analysis," Current Protocols in Cytometry, 2001, 7.5.1-7.5.24.

(56) References Cited

OTHER PUBLICATIONS

De Simone et al., "Accurate random coil chemical shifts from an analysis of loop regions in native states of proteins," J Am Chem Soc, 2009, 131, 16332-16333.

Deer et al., "Phenotype and genotype of pancreatic cancer cell lines," Pancreas, 2010, 39, 425-435.

Dejana et al., "The role of adherens junctions and VE-cadherin in the control of vascular permeability," J Cell Sci, 2008, 121, 2115-2122.

Delaglio et al., "NMRPipe: A multidimensional spectral processing system based on UNIX pipes," Journal of Biomolecular NMR 6, 1995, 277-293.

DeLisser et al., "Vascular endothelial platelet endothelial cell adhesion molecule 1(PECAM-1) regulates advanced metastatic progression," PNAS, 2010, 107, 18616-18621.

Dennis et al., "Albumin binding as a general strategy for improving the pharmacokinetics of proteins," J Biol Chem, 2002, 277(38): p. 35035-43.

Deshayes et al., "Radium 223 dichloride for prostate cancer treatment," Drug Des Devel Ther, 2017, 11, 2643-2651.

Diana et al., "Prognostic role and correlation of CA9, CD31, CD68 and CD20 with the desmoplastic stroma in pancreatic ductal adenocarcinoma," Oncotarget, 2016, 7, 72819-72832.

Ding et al., "Mechanism for the alpha-helix to beta-hairpin transition," Proteins, 2003, 53, 220-228.

Dreher et al., "Thermal cycling enhances the accumulation of a temperature-sensitive biopolymer in solid tumors," Cancer Res, 2007, 67, 4418-4424.

Du et al., "Endoscope-assisted brachytherapy for pancreatic cancer: From tumor killing to pain relief and drainage," Journal of interventional gastroenterology, 2011, 1, 23-27.

Ducreux et al., "Radiation plus docetaxel and cisplatin in locally advanced pancreatic carcinoma: A non-comparative randomized phase II trial," Digestive and Liver Disease, 2014, 46, 950-955.

Duke University, "Gemcitabine/Nab-Paclitaxel With HIGRT in Resectable Pancreatic Cancer," Clinical Trial NCT02318095 <https://clinicaltrials.gov/ct2/show/NCT02318095> Accessed Jan. 11, 2017.

Duncan, "The dawning era of polymer therapeutics," Nature Reviews Drug Discovery, 2003, 2, 347-360.

Eisenhauer et al., "New response evaluation criteria in solid tumours: Revised RECIST guideline (version 1.1)," Eur J Cancer, 2017, 45, 228-247.

Ellis, "Macromolecular crowding: obvious but underappreciated," Trends Biochem. Sci., 2001, 26 (10), 597-604.

Engin et al., "Thermoradiotherapy in the management of superficial malignant tumors," Clinical Cancer Research, 1995, 1, 139-145.

Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.

Falk et al., "Hyperthermia in oncology," Int J Hyperthermia, 2001, 17, 1-18.

Farmer et al., "Conformational behavior of chemically reactive alanine-rich repetitive protein polymers," Biomacromolecules, 2005, 6, 1531-1539.

Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, 2015, 16, 3389-3398.

Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, 2018, 130:A19112.

Frilling et al., "Recommendations for management of patients with neuroendocrine liver metastases," The lancet oncology, 2014, 15, e8-21.

Fu et al., Recent Patents on Anti-Cancer Drug Discovery, 2009. 4(3): p. 262-272.

Fujiwara et al., "Modulating effect of the PI3-kinase inhibitor LY294002 on cisplatin in human pancreatic cancer cells," Journal of Experimental & Clinical Cancer Research, 2008, 27, 76.

Furumoto et al., "Effect of coupling of albumin onto surface of PEG liposome on its In vivo disposition," International Journal of Pharmaceutics, 2007, 329(1-2): p. 110-116.

Ghoorchian et al., "Molecular architecture influences the thermally induced aggregation behavior of elastin-like polypeptides," Biomacromolecules, 2011, 12, 4022-4029.

Gianni et al., "Nonlinear pharmacokinetics and metabolism of paclitaxel and its pharmacokinetic/pharmacodynamic relationships in humans," J. Clin. Oncol., 1995, 13 (1), 180-190.

Giberti et al., "Radical retropubic prostatectomy versus brachytherapy for low-risk prostatic cancer: a prospective study," World J Urol, 2009, 27, 607-612.

Glassman et al., "Toughening of Thermoresponsive Arrested Networks of Elastin-Like Polypeptides to Engineer Cytocompatible Tissue Scaffolds," Biomacromolecules, 2016, 17, 415-426.

Gosline et al., "Elastic proteins: biological roles and mechanical properties," Philos Trans R Soc Lond B Biol Sci, 2002, 357, 121-132.

Gottlieb et al., "NMR chemical shifts of common laboratory solvents as trace impurities," J. Org. Chem., 1997, 62, 7512-7515.

Greco et al., "The search for synergy: a critical review from a response surface perspective," Pharmacological Reviews, 1995, 24, 331-385.

Green et al., "Abraxane®, a novel Cremophor®-free, albumin-bound particle form of paclitaxel for the treatment of advanced non-small-cell lung cancer," Annals of Oncology, 2006, 17, 1263-1268.

Grimm et al., "Advances in Brachytherapy," Reviews in Urology, 2004, 6, S37-S48.

Güngör et al., "Pancreatic cancer," British Journal of Pharmacology, 2014, 171, 849-858.

Guo et al., "Nanoparticles escaping RES and endosome: challenges for siRNA delivery for cancer therapy," J. Nanomaterials, 2011, 2011: 1-12.

Gustafsson, "Nonlinear structured-illumination microscopy: widefield fluorescence imaging with theoretically unlimited resolution," Proc Natl Acad Sci U S A, 2005, 102, 13081-13086.

Gustafsson, "Surpassing the lateral resolution limit by a factor of two using structured illumination microscopy," Short Communication. Journal of Microscopy, 2000, 198, 82-87.

Guzman et al., "Leiodermatolide, a novel marine natural product, has potent cytotoxic and antimitotic activity against cancer cells, appears to affect microtubule dynamics, and exhibits antitumor activity," Int. J. Cancer, 2016, 139, 2116-2126.

Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.

Hamada et al., "Novel therapeutic strategies targeting tumor-stromal interactions in pancreatic cancer," Frontiers in Physiology, 2013, vol. 4, Article 331, 7 pages.

Han et al., "Survival of patients with advanced pancreatic cancer after iodine[125] seeds implantation brachytherapy: A meta-analysis," Medicine, 2017, 96, e5719.

Harmon et al., "A Model for Hysteresis Observed in Phase Transitions of Thermally Responsive Instrinsically Disordered Protein Polymers," Biophysical Journal, 2017, 112(3):207a.

Hathout et al., "Analysis of seed loss and pulmonary seed migration in patients treated with virtual needle guidance and robotic seed delivery," American journal of clinical oncology, 2011, 34, 449-453.

Herrero-Vanrell et al., "Self-assembled particles of an elastin-like polymer as vehicles for controlled drug release," J Control Release, 2005, 102, 113-122.

Hidalgo, "Pancreatic Cancer," N Engl J Med, 2010, 362, 1605-1617.

Hingorani et al., "Phase Ib Study of PEGylated Recombinant Human Hyaluronidase and Gemcitabine in Patients with Advanced Pancreatic Cancer," Clinical Cancer Research, 2016, 22, 2848-2854.

(56) References Cited

OTHER PUBLICATIONS

Ho et al., "Internal radiation therapy for patients with primary or metastatic hepatic cancer: a review," Cancer, 1998, 83, 1894-1907.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, 2007, 119, 25-33.
Hruby et al., "Thermoresponsive polymeric radionuclide delivery system—an injectable brachytherapy," Eur J Pharm Sci., 2011, 42, 484-488.
Hrycushko et al., "Direct intratumoral infusion of liposome encapsulated rhenium radionuclides for cancer therapy: effects of non-uniform intratumoral dose distribution," Med Phys, 2011, 38, 1339-1347.
Hu et al., "Design of tumor-homing and pH-responsive polypeptide-doxorubicin nanoparticles with enhanced anticancer efficacy and reduced side effects," Chemical Communications, 2015, 51, 11405-11408.
Huang et al., "Photodynamic Therapy Synergizes with Irinotecan to Overcome Compensatory Mechanisms and Improve Treatment Outcomes in Pancreatic Cancer," Cancer Research, 2016, 76, 1066-1077.
Huotari et al., "Endosome maturation," EMBO J, 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ito et al., "In vivo antitumor effect of the mTOR inhibitor CCI-779 and gemcitabine in xenograft models of human pancreatic cancer," International Journal of Cancer, 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, 2012, 13, 206-215.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Jonsson et al., "Engineering of a femtomolar affinity binding protein to human serum albumin," Protein Engineering Design and Selection, 2008, 21(8): 515-527.
Kaighn et al., "Establishment and characterization of a human prostatic carcinoma cell line (PC-3)," Investigative urology, 1979, 17, 16-23.

Kaitin et al., "Pharmaceutical innovation in the 21st century: new drug approvals in the first decade, 2000-2009," Clin Pharmacol Ther, 2011, 89, 183-188.
Kamisawa et al., "Pancreatic cancer," Lancet, 2016, 388, 73-85.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karamanolis et al., "Increased expression of VEGF and CD31 in postradiation rectal tissue: implications for radiation proctitis," Mediators Inflamm, 2013, 515048.
Karperien, A. FracLac for Image J, version 2.5 <http://rsb.info.nih.gov/ij/plugins/fraclac/FLHelp/Introduction.htm> 1999-2012.
Katakura, "Nuclear Data Sheets for A=125," Nuclear Data Sheets, 2011, 112, 495-705.
Kato et al., "Acidic extracellular microenvironment and cancer," Cancer Cell Int, 2013, 13, 89, 8 pages.
Keten et al., "Nanoconfinement controls stiffness, strength and mechanical toughness of β-sheet crystals in silk," Nat Mater, 2010, 9, 359-367.
Khanna et al., "The dog as a cancer model," Nat. Biotechnol., 2006, 24, 1065-1066.
Khazov et al., "Nuclear Data Sheets for A=131," Nuclear Data Sheets, 2006, 107, 2715-2930.
Kim et al., "Recombinant elastin-mimetic biomaterials: Emerging applications in medicine," Adv Drug Deliv Rev, 2010, 62, 1468-1478.
Kobayashi et al., "Summary of recombinant human serum albumin development," Biologicals, 2006, 34(1): 55-59.
Koehler et al., "Albumin affinity tags increase peptide half-life In vivo," Bioorganic & Medicinal Chemistry Letters, 2002, 12(20): 2883-2886.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, 2008, 1778, 631-645.
Krempien et al., "Neoadjuvant chemoradiation in patients with pancreatic adenocarcinoma," HPB (Oxford), 2006, 8, 22-28.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Labelle et al., "Vascular endothelial cadherin promotes breast cancer progression via transforming growth factor β signaling," Cancer Res, 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Lee et al., "Immunohistochemical analysis of claudin expression in pancreatic cystic tumors," Oncology Reports, 2011, 25(4): 971-978.
Lee et al., "In vivo bioluminescent imaging of irradiated orthotopic pancreatic cancer xenografts in nonobese diabeti-sever combined immunodeficient mice: a novel method for targeting and assaying efficacy of ionizing radiation," Transl. Oncol., 2010, 3, 153-159.
Lee et al., "Mechanical properties of cross-linked syntheti elastomeric polypentapeptides," Macromolecules, 2001, 34, 5968-5974.
Lee et al., "Phase transition and elasticity of protein-based hydrogels," J. Biomater. Sci. Polymer Edn, 2001, 12, 229-242.
Levy et al., "Novel Exenatide Analogs with Peptidic Albumin Binding Domains: Potent Anti-Diabetic Agents with Extended Duration of Action," PLoS ONE, 2014, 9(2): e87704, 9 pages.
Li et al., "Elastin is an essential determinant of arterial morphogenesis," Nature, 1998, 393, 276-280.
Li et al., "Nanoparticles Evading the Reticuloendothelial System: Role of the Supported Bilayer," Biochim. Biophys. Acta, 2009, 1788 (10), 2259-2266.

(56) References Cited

OTHER PUBLICATIONS

Li et al., "Pancreatic cancer," Lancet, 2004, 363, 1049-1057.
Lillie et al., "The viscoelastic basis for the tensile strength of elastin," Int J Biol Macromol, 2002, 30, 119-127.
Lin et al., "Utility of immunohistochemistry in the pancreatobiliary tract," Arch Pathol Lab Med, 2015, 139, 24-38.
Litiere et al., "RECIST—learning from the past to build the future," Nat Rev Clin Oncol, 2017, 14, 187-192.
Liu et al., "Brachytherapy using injectable seeds that are self-assembled from genetically encoded polypeptides in situ," Cancer Res, 2012, 72, 5956-5965.
Liu et al., "Tracking the in vivo fate of recombinant polypeptides by isotopic labeling," Journal of Controlled Release, 2006, 114, 184-192.
Liu et al., "Tumor accumulation, degradation and pharmacokinetics of elastin-like polypeptides in nude mice," Journal of Controlled Release, 2006, 116, 170-178.
Ludden, "Nonlinear pharmacokinetics: clinical Implications," Clin. Pharmacokinet., 1991, 20 (6), 429-446.
Luo et al., "Noncovalent Modulation of the Inverse Temperature Transition and Self-Assembly of Elastin-b-Collagen-like Peptide Bioconjugates," J Am Chem Soc, 2015, 137, 15362-15365.
MacEwan et al., "Applications of elastin-like polypeptides in drug delivery," Journal of Controlled Release, 2014, 190: p. 314-330.
MacEwan et al., "Controlled apoptosis by a thermally toggled nanoscale amplifier of cellular uptake," Nano Letters, 2014, 14, 2058-2064.
Maitra et al., "Pancreatic Cancer," Annu Rev Pathol Mech Dis, 2008, 3, 157-188.
Manzoor et al., "Overcoming limitations in nanoparticle drug delivery: triggered, intravascular release to improve drug penetration into tumors," Cancer Res, 2012, 72, 5566-5575.
Mao et al., "DNA repair by nonhomologous end joining and homologous recombination during cell cycle in human cells," Cell cycle, 2008, 7, 2902-2906.
Mariam et al., "Albumin corona on nanoparticles—a strategic approach in drug delivery," Drug Deliv., 2016, 23 (8), 2668-2676.
Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, 2009, 9, 1-8.
Matsumura, "Cancer stromal targeting (CAST) therapy," Advanced Drug Delivery Reviews, 2012, 64, 710-719.
McConkey et al., "Molecular Characterization of Pancreatic Cancer Cell Lines," Pancreatic Cancer, 2010, 457-469.
McDaniel et al., "Actively targeting solid tumours with thermoresponsive drug delivery systems that respond to mild hyperthermia," Int J Hyperthermia, 2013, 29, 501-510.
McDaniel et al., "Doxorubicin-conjugated chimeric polypeptide nanoparticles that respond to mild hyperthermia," Control. Release, 2012, 159 (3), 362-367.
McDaniel et al., "Rational design of "heat seeking" drug loaded polypeptide nanoparticles that thermally target solid tumors," Nano Letters, 2014, 14, 2890-2895.
Merrick et al., "Seed fixity in the prostate/periprostatic region following brachytherapy," International journal of radiation oncology, biology, physics, 2000, 46, 215-220.
Methods and Welfare Considerations in Behavioral Research with Animal. (2002).
Meyer et al., "Drug targeting using thermally responsive polymers and local hyperthermia," Journal of Controlled Release, 2001, 74, 213-224.
Miao et al., "Sequence and domain arrangements influence mechanical properties of elastin-like polymeric elastomers," Biopolymers, 2013, 99, 392-407.
Miao et al., "Structural determinants of cross-linking and hydrophobic domains for self-assembly of elastin-like polypeptides," Biochemistry, 2005, 44, 14367-14375.

Michl et al., "Current concepts and novel targets in advanced pancreatic cancer," Gut, 2013, 62, 317-326.
Micsonai et al., "Accurate secondary structure prediction and fold recognition for circular dichroism spectroscopy," Proc Natl Acad Sci U S A, 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Miyata et al., "Polymeric micelles for nano-scale drug delivery," Reaction & Functional Polymers, 2011, 71, 227-234.
Mjelle et al., "Cell cycle regulation of human DNA repair and chromatin remodeling genes," DNA Repair, 2015, 30, 53-67.
Morgan et al., "The combination of epidermal growth factor receptor inhibitors with gemcitabine and radiation in pancreatic cancer," Clin Cancer Res, 2008, 14, 5142-5149.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Murphy et al., "A dosimetric model of duodenal toxicity after stereotactic body radiotherapy for pancreatic cancer," Int J Radiation Oncology Biol Phys, 2010, 78, 1420-1426.
Na et al., "Thermoresponsive pore structure of biopolymer microspheres for a smart drug carrier," Langmuir, 2010, 26, 11165-11169.
Nettles et al., "Applications of elastin-like polypeptides in tissue engineering," Adv Drug Deliv Rev, 2010, 62, 1479-1485.
Nettles et al., "In situ crosslinking elastin-like polypeptide gels for application to articular cartilage repair in a goat osteochondral defect model," Tissue Eng Part A, 2008, 14, 1133-1140.
Newton et al., "Commissioning a small-field biological irradiator using point, 2D, and 3D dosimetry techniques," Medical Physics, 2011, 38, 6754-6762.
Nichols et al., "Claudin 4 protein expression in primary and metastatic pancreatic cancer," Am J Clin Pathol, 2004, 121, 226-230.
Nie, "Understanding and overcoming major barriers in cancer nanomedicine," Nanomedicine (Lond) 2010, 5 (4), 523-528.
Nilvebrant et al., "The albumin-binding domain as a scaffold for protein engineering," Computational and Structural Biotechnology Journal, 2013, 6: e201303009, 8 pages.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Pagani et al., "International guidelines for management of metastatic breast cancer: can metastatic breast cancer be cured?," Journal of the National Cancer Institute, 2010, 102, 456-463.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, 2016, 96, S204-S205.
Paoloni et al., "Translation of new cancer treatments from pet dogs to humans," Nat. Rev. Cancer 2008, 8 (2), 147-156.
Patil et al., "Cellular delivery of doxorubicin via pH-controlled hydrazone linkage using multifunctional nano vehicle based on poly(beta-I-malic acid)," Int J Mol Sci, 2012, 13, 11681-11693.
Phan et al., "Temperature-responsive self-assembly of charged and uncharged hydroxyethylcellulose-graft-poly(N-isopropylacrylamide) copolymer in aqueous solution," Colloid Polym. Sci., 2011, 289 (9), 993-1003.

(56) References Cited

OTHER PUBLICATIONS

Pliarchopoulou et al., "Pancreatic cancer: Current and future treatment strategies," Cancer Treatment Reviews, 2009, 35, 431-436.
Pometun et al., "Quantitative observation of backbone disorder in native elastin," J Biol Chem, 2004, 279, 7982-7987.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, 2012, 21, 418-429.
Provenzano et al., "Hyaluronan, fluid pressure, and stromal resistance in pancreas cancer," Br J Cancer, 2013, 108, 1-8.
Qiu et al., "Development of Orthotopic Pancreatic Tumor Mouse Models," Methods Mol Biol, 2013, 980: 215-223.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Rabotyagova et al., "Protein-based block copolymers," Biomacromolecules, 2011, 12, 269-289.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, 2016, 76.
Rankine et al., "Investigating end-to-end accuracy of image guided radiation treatment delivery using a micro-irradiator," Physics in Medicine and Biology, 2013, 58, 7791-7801.
Rao et al., "Synthetic nanoparticles camouflaged with biometric erythrocyte membranes for reduced reticuloendothelial system uptake," Nanotechnology, 2016, 27 (8), 85106, 9 pages.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, 2016, 3, 107-110.
Regier et al., American Heart Association 2014 Scientific Sessions, 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, 2008, 2(2): p. 141-150.
Ribeiro et al., "Influence of the amino-acid sequence on the inverse temperature transition of elastin-like polypeptides," Biophysical Journal, 2009, 97, 312-320.
Richards et al., "Man's best friend: what can pet dogs teach us about non-Hodgkin lymphoma?" Inmunol Rev., 2016, 263 (1), 173-191.
Rincon et al., "Biocompatibility of elastin-like polymer poly(VPAVG) microparticles: in vitro and in vivo studies," Journal of Biomedical Materials Research, 2005, 78A, 343-351.

Rios-Doria et al., "Doxil synergizes with cancer immunotherapies to enhance antitumor responses in syngeneic mouse models," Neoplasia, 2015, 17, 661-670.
Roopenian et al., "FcRn: the neonatal Fc receptor comes of age," Nat. Rev. Immunol., 2007, vol. 7, No. 9, 715-725.
Rosenberg et al., "Present and future innovations in radiation oncology," Surg Oncol Clin N Am, 2013, 22, 599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Russo et al., "The role of neoadjuvant therapy in pancreatic cancer: a review," Future Oncol, 2016, 12, 669-685.
Ryerson et al., "Annual report to the nation on the status of cancer, 1975-2012, featuring the Increasing incidence of liver cancer," Cancer, 2016, 122, 1312-1337.
Saba et al., "A Comparative Oncology Study of Iniparib Defines Its Pharmacokinetic Profile and Biological Activity in a Naturally-Occurring Canine Cancer Model," PLoS One, 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, 2009, 131, 9304-9310.
Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, 2016, 228, 58-66.
Schellenberg et al., "Gemcitabine chemotherapy and single-fraction stereotactic body radiotherapy for locally advanced pancreatic cancer," Int J Radiation Oncol Biol Phys, 2008, 72, 678-686.
Schellenberg et al., "Single-fraction stereotactic body radiation therapy and sequential gemcitabine for the treatment of locally advanced pancreatic cancer," Int J Radiation Oncology Biol Phys, 2011, 81, 181-188.
Schlaff et al., "Bringing the heavy: carbon ion therapy in the radiobiological clinical context," Radiation Oncology, 2014, 9, 1-18.
Schneider et al., "NIH Image to ImageJ: 25 years of image analysis," Nature Methods, 2012, 9, 671-675.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, 2007, 23 (5), 2714-2721.
Shao et al., "Super-resolution 3D microscopy of live whole cells using structured illumination," Nat Methods, 2011, 8, 1044-1046.
Siegel et al., "Absorbed fractions for electrons and beta particles in spheres of various sizes," J Nucl Med, 1994, 35, 152-156.
Silberstein et al., "The SNM Practice Guideline for Therapy of Thyroid Disease with $^{131}$I, 3.0," J Nucl Med, 2012, 53, 1-19.
Simnick et al., "In vivo tumor targeting by a NGR-decorated micelle of a recombinant diblock copolypeptide," J Control Release, 2011, 155, 144-151.
Simnick et al., "Morphing low-affinity ligands into high-avidity nanoparticles by thermally triggered self-assembly of a genetically encoded polymer," ACS Nano, 2010, 4, 2217-2227.
Sisson et al., "Radiation safety in the treatment of patients with thyroid diseases by radioiodine 131I: practice recommendations of the American Thyroid Association," Thyroid, 2011, 21, 335-346.
Sonawane et al., "Hydrazo linkages in pH responsive drug delivery systems," European Journal Pharmaceutical Sciences, 2017, 99, 45-65.
Sousa et al., "Production of a polar fish antimicrobial peptide in *Escherichia coli* using an ELP-intein tag," J Biotechnol, 2016, 234:83-89.
Sriraman et al., "Barriers to drug delivery in solid tumors," Tissue Barriers, 2014, 2, 2-10.

(56) References Cited

OTHER PUBLICATIONS

Stock et al., "Penile erectile function after permanent radioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, 2007, 20(11): p. 569-576.
Strohmaier et al., "Comparison of $^{60}$Co and $^{192}$Ir sources in HDR brachytherapy," J Contemp Brachyther, 2011, 3, 199-208.
Stutz et al., "Seed loss through the urinary tract after prostate brachytherapy: examining the role of cystoscopy and urine straining post implant," Medical physics, 2003, 30, 2695-2698.
Sugyo et at, "Evaluation of efficacy of radioimmunotherapy with 90Y-labeled fully human anti-transferring receptor monoclonal antibody in pancreatic cancer mouse models," PLoS One, 2015, 10, 1-17.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, 2015, 16, 438-449.
Sun et al., "EUS-guided interstitial brachytherapy of the pancreas: a feasibility study," Gastrointestinal Endoscopy, 2005, 62, 775-779.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Sussman et al., "Porous implants modulate healing and induce shifts in local macrophage polarization in the foreign body reaction," Ann Biomed Eng, 2014, 42, 1508-1516.
Takalkar et al., "Radium-223 dichloride bone-targeted alpha particle therapy for hormone-refractory breast cancer metastatic to bone," Exp Hematol Oncol, 2014, 8, 23.
Tallarida, "Quantitative methods for assessing drug synergism," Genes & Cancer, 2011, 2, 1003-1008.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, 2006, 45, 9518-9530.
Tan et al., "Characterization of a new primary human pancreatic tumor line," Cancer investigation, 1986, 4, 15-23.
Tang et al., "Identification of PECAM-1 in solid tumor cells and its potential involvement in tumor cell adhesion to endothelium," J. Biol. Chem., 1993, 268, 22883-22894.
Teicher, "In vivo/ex vivo and in situ assays used in cancer research: a brief review," Toxicol. Pathol., 2009, 37 (1), 114-122.
Therasse et al., "New guidelines to evaluate the response to treatment in solid tumors," J Natl Cancer Inst, 2000, 92, 205-216.
Tompa et al., "Fuzzy complexes: polymorphism and structural disorder in protein-protein interactions," Trends Biochem Sci, 2008, 33, 2-8.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trakul et al., "Stereotactic body radiotherapy in the treatment of pancreatic cancer," Semin Radiat Oncol, 2014, 24, 140-147.
Trieu et al., "P0157 Preclinical evaluation of NBN-paclitaxel in pancreatic cancer xenograft models," Eur J Cancer, 2014, 50, e53.
Tu et al., "Stages in tropoelastin coalescence during synthetic elastin hydrogel formation," Micron, 2010, 41, 268-272.

Tward et al., "Survival of men with clinically localized prostate cancer treated with prostatectomy, brachytherapy, or no definitive treatment: impact of age at diagnosis," Cancer, 2006, 107, 2392-2400, doi:10.1002/cncr.22261.
Uchida et al., "Potential of adenovirus-mediated REIC/Dkk-3 gene therapy for use in the treatment of pancreatic cancer," Journal of Gastroenterology and Hepatology, 2014, 29, 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Temperature dependence of length of elastin and its polypentapeptide," Biochem Biophys Res Commun, 1986, 141, 749-755.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, 2018, 15, 366-381.
Van der Lee et al., "Classification of intrinsically disordered regions and proteins," Chem Rev, 2014, 114, 6589-6631.
Van Roey et al., "Short linear motifs: ubiquitous and functionally diverse protein interaction modules directing cell regulation," Chem Rev, 2014, 114, 6733-6778.
Van Roy, "Beyond E-cadherin: roles of other cadherin superfamily members in cancer," Nat Rev Cancer, 2014, 14, 121-134.
Vicini et al., "An interinstitutional and interspecialty comparison of treatment outcome data for patients with prostate carcinoma based on predefined prognostic categories and minimum follow-up," Cancer, 2002, 95, 2126-2135.
Volkova et al, "Anthracycline Cardiotoxicity: Prevalence, Pathogenesis and Treatment," Curr. Cardiol. Rev., 2011, vol. 7, No. 4, pp. 214-220.
Vrhovski et al., "Biochemistry of tropoelastin," Eur J Biochem, 1998, 258, 1-18.
Wang et al., "Extending Half Life of H-Ferritin Nanoparticle by Fusing Albumin Binding Domain for Doxorubicin Encapsulation," Biomacromolecules, 2018, 12, 19(3):773-781.
Wang et al., "Quantitative Mapping of the Spatial Distribution of Nanoparticles in Endo-Lysosomes by Local pH," Nano Lett., 2017, 17(2): 1226-1232.
Wang et al., "Size and dynamics of caveolae studied using nanoparticles in living endothelial cells," ACS nano, 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, 2015, 112(10): 2978-2983.
Williams et al., "Targeted radionuclide therapy," Medical Physics, 2008, 35, 3062-3068.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wust et al., "Hyperthermia in combined treatment of cancer," The Lancet Oncology, 2002, 3, 487-497.

(56) References Cited

OTHER PUBLICATIONS

Xia et al., "Tunable self-assembly of genetically engineered silk—elastin-like protein polymers," Biomacromolecules, 2011, 12, 3844-3850.

Xu et al., "Genetically engineered block copolymers: influence of the length and structure of the coiled-coil blocks on hydrogel self-assembly," Pharm Res, 2008, 25, 674-682.

Xu et al., "Role of pancreatic stellate cells in pancreatic cancer metastasis," Am J of Pathology, 2010, 177, 2585-2596.

Yates et al., "Contemporary management of patients with high-risk non-muscle-invasive bladder cancer who fail intravesical BCG therapy," World journal of urology, 2011, 29, 415-422.

Yeo et al., "Coacervation of tropoelastin," Adv Colloid Interface Sci, 2011, 167, 94-103.

Yokoe et al., "Albumin-conjugated PEG liposome enhances tumor distribution of liposomal doxorubicin in rats," International Journal of Pharmaceutics, 2008, 353(1-2): 28-34.

Yousefpour et al., "Co-opting biology to deliver drugs," Biotechnol Bioeng, 2014, 111(9): p. 1699-1716.

Yousefpour et al., "Genetically Encoding Albumin Binding into Chemotherapeutic-loaded Polypeptide Nanoparticles Enhances Their Antitumor Efficacy," Nano Lett. 2018, 18(12): 7784-7793.

Yu et al., "Effectiveness and security of CT-guided percutaneous implantation of (125)I seeds in pancreatic carcinoma," The British journal of radiology, 2014, 87, 20130642, 7 pages.

Zhang et al., "Novel agents for pancreatic ductal adenocarcinoma: emerging therapeutics and future directions," Jounral of Hematology & Oncology, 2018, 11:14, 17 pages.

Zhao et al., "A new Bliss Independence model to analyze drug combination data," J Biomol Screen, 2014, 19, 817-821.

Zini et al., "Contemporary management of adrenocortical carcinoma," European urology, 2011, 60, 1055-1065.

International Search Report and Written Opinion for Application No. PCT/US2018/040409 dated Nov. 5, 2018 (16 pages).

United States Patent Office Action for U.S. Appl. No. 15/561,799 dated Dec. 27, 2018 (8 pages).

United States Patent Office Notice of Allowance for U.S. Appl. No. 15/561,799 dated Apr. 2, 2019 (6 pages).

United States Patent Office Notice of Allowance for U.S. Appl. No. 15/387,540 dated Apr. 17, 2019 (9 pages).

\* cited by examiner 1) cloning
2) expression
3) purification by ITC exendin-srt-His$_6$-ELP

FIG. 1A

His$_6$-sortase A
AEBMP exendin-C-Br

FIG. 1B ically involves reacting the chain-ends of the polymer with reactive side-groups on lysine and cysteine residues, which are often promiscuously distributed on the biomolecule, thus yielding chemically heterogeneous products that can significantly compromise the bioactivity of the drug and greatly complicate regulatory approval.

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is any amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic

<400> SEQUENCE: 2

Leu Pro Glu Thr Gly
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is any amino acid independent of X located
      at position 4
<220> FEATURE:
<221> NAME/KEY: misc_feature
<222> LOCATION: (4)..(4)
<223> OTHER INFORMATION: Xaa is any amino acid independent of X located
      at position 3

<400> SEQUENCE: 3

Leu Pro Xaa Xaa Gly
1               5

<210> SEQ ID NO 4
<211> LENGTH: 3
```

```
<212> TYPE: PRT
<213> ORGANISM: Artificial sequence
<220> FEATURE:
<223> OTHER INFORMATION: Synthetic

<400> SEQUENCE: 4

Gly Gly Cys
1

<210> SEQ ID NO 5
<211> LENGTH: 24
<212> TYPE: PRT
<213> ORGANISM: Artificial sequence
<220> FEATURE:
<223> OTHER INFORMATION: Synthetic

<400> SEQUENCE: 5

Gly Gly Cys Gly Gly Cys Gly Gly Cys Gly Gly Cys Gly Gly Cys Gly
1               5                  10                  15

Gly Cys Gly Gly Cys Gly Gly Cys
            20

<210> SEQ ID NO 6
<211> LENGTH: 15
<212> TYPE: PRT
<213> ORGANISM: Artificial sequence
<220> FEATURE:
<223> OTHER INFORMATION: Synthetic

<400> SEQUENCE: 6

Gly Gly Gly Gly Ser Gly Gly Gly Gly Ser Gly Gly Gly Gly Ser
1               5                  10                  15

<210> SEQ ID NO 7
<211> LENGTH: 80
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is a valine or cysteine present in a ratio
      of 1:1
<220> FEATURE:
<221> NAME/KEY: misc_feature
<222> LOCATION: (9)..(9)
<223> OTHER INFORMATION: Xaa is a valine or cysteine present in a ratio
      of 1:1
<220> FEATURE:
<221> NAME/KEY: misc_feature
<222> LOCATION: (14)..(14)
<223> OTHER INFORMATION: Xaa is a valine or cysteine present in a ratio
      of 1:1
<220> FEATURE:
<221> NAME/KEY: misc_feature
<222> LOCATION: (19)..(19)
<223> OTHER INFORMATION: Xaa is a valine or cysteine present in a ratio
      of 1:1
<220> FEATURE:
<221> NAME/KEY: misc_feature
<222> LOCATION: (24)..(24)
<223> OTHER INFORMATION: Xaa is a valine or cysteine present in a ratio
      of 1:1
<220> FEATURE:
<221> NAME/KEY: misc_feature
<222> LOCATION: (29)..(29)
<223> OTHER INFORMATION: Xaa is a valine or cysteine present in a ratio
      of 1:1
<220> FEATURE:
<221> NAME/KEY: misc_feature
<222> LOCATION: (34)..(34)
```

```
<223> OTHER INFORMATION: Xaa is a valine or cysteine present in a ratio
      of 1:1
<220> FEATURE:
<221> NAME/KEY: misc_feature
<222> LOCATION: (39)..(39)
<223> OTHER INFORMATION: Xaa is a valine or cysteine present in a ratio
      of 1:1
<220> FEATURE:
<221> NAME/KEY: misc_feature
<222> LOCATION: (44)..(44)
<223> OTHER INFORMATION: Xaa is a valine or cysteine present in a ratio
      of 1:1
<220> FEATURE:
<221> NAME/KEY: misc_feature
<222> LOCATION: (49)..(49)
<223> OTHER INFORMATION: Xaa is a valine or cysteine present in a ratio
      of 1:1
<220> FEATURE:
<221> NAME/KEY: misc_feature
<222> LOCATION: (54)..(54)
<223> OTHER INFORMATION: Xaa is a valine or cysteine present in a ratio
      of 1:1
<220> FEATURE:
<221> NAME/KEY: misc_feature
<222> LOCATION: (59)..(59)
<223> OTHER INFORMATION: Xaa is a valine or cysteine present in a ratio
      of 1:1
<220> FEATURE:
<221> NAME/KEY: misc_feature
<222> LOCATION: (64)..(64)
<223> OTHER INFORMATION: Xaa is a valine or cysteine present in a ratio
      of 1:1
<220> FEATURE:
<221> NAME/KEY: misc_feature
<222> LOCATION: (69)..(69)
<223> OTHER INFORMATION: Xaa is a valine or cysteine present in a ratio
      of 1:1
<220> FEATURE:
<221> NAME/KEY: misc_feature
<222> LOCATION: (74)..(74)
<223> OTHER INFORMATION: Xaa is a valine or cysteine present in a ratio
      of 1:1
<220> FEATURE:
<221> NAME/KEY: misc_feature
<222> LOCATION: (79)..(79)
<223> OTHER INFORMATION: Xaa is a valine or cysteine present in a ratio
      of 1:1

<400> SEQUENCE: 7

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

<210> SEQ ID NO 8
<211> LENGTH: 16
<212> TYPE: PRT
<213> ORGANISM: Artificial sequence
<220> FEATURE:
<223> OTHER INFORMATION: Synthetic

<400> SEQUENCE: 8

Asn Gly Gly Pro Ser Ser Gly Ala Pro Pro Pro Ser Leu Pro Glu Thr
1               5                   10                  15
```

POLYMER CONJUGATES HAVING REDUCED ANTIGENICITY AND METHODS OF USING THE SAME

CROSS-REFERENCE TO RELATED APPLICATIONS

This application is a continuation-in-part of U.S. patent application Ser. No. 14/894,731 filed Nov. 30, 2015, which is a national stage filing under 35 U.S.C. 371 of International Patent Application No. PCT/US2014/040319, filed May 30, 2014, which claims the benefit of priority to U.S. Provisional Patent Application No. 61/828,873, filed May 30, 2013, each of which is incorporated herein by reference in its entirety. This application also claims priority to U.S. Provisional Patent Application No. 62/270,401, filed Dec. 21, 2015; U.S. Provisional Patent Application No. 62/310,534, filed Mar. 18, 2016; U.S. Provisional Patent Application No. 62/329,800, filed Apr. 29, 2016; and U.S. Provisional Patent Application No. 62/407,403, filed Oct. 12, 2016, each of which is incorporated herein by reference in its entirety.

STATEMENT REGARDING FEDERALLY SPONSORED RESEARCH

This invention was made with government support under grants R01-DK092665, R01-GM061232, 5T32-GM008487, R01-GM061232, and R01-AI46611 awarded by the National Institutes of Health. The government has certain rights in the invention.

FIELD

This disclosure relates to molecule-polymer conjugates having reduced or eliminated antigenicity.

INTRODUCTION

With more than a hundred peptides and proteins approved by the FDA to treat various diseases and many more in clinical and pre-clinical development, therapeutic peptides and proteins are an important class of drugs today. However, the clinical use of peptides and proteins is often challenged by their short plasma half-life, which can necessitate frequent injections and cause an undesirable peak-to-valley fluctuation of the drug concentration in vivo as well as reduce patient compliance and increase treatment cost. Other limitations of peptide and protein therapeutics may include poor stability, low solubility and immunogenicity. To address these limitations, various delivery strategies have been developed for sustained delivery of peptide and protein therapeutics, ranging from particulate systems, depots, to chemical conjugation with long circulating polymers such as poly(ethylene glycol) (PEG), or recombinant fusions with long circulating proteins such as albumin or the Fc domain of antibodies.

PEGylation, or the covalent conjugation of therapeutics with the "stealth" polymer PEG, is one of the most widely used approaches to increase the circulation half-life and stability and to reduce the immunogenicity of biomolecule therapeutics such as polypeptides and polynucleotides. However, after nearly four decades of research and over two decades of clinical use, the drawbacks of PEGylation have begun to emerge. Conventional methods for the synthesis of PEGylated conjugates have significant limitations: (1) conjugation involves the reaction between protein-repulsive PEG chains and biomacromolecules, so that even with a large excess of polymer, steric hindrance still results in a low yield of conjugate, typically in the 10-20% range; (2) the presence of a large excess of unreacted polymer makes product purification non-trivial; and (3) conjugation typically involves reacting the chain-ends of the polymer with reactive side-groups on lysine and cysteine residues, which are often promiscuously distributed on the biomolecule, thus yielding chemically heterogeneous products that can significantly compromise the bioactivity of the drug and greatly complicate regulatory approval.

Furthermore, the immunogenicity of PEG has recently attracted much attention. Anti-PEG antibodies have been induced in patients treated with some PEGylated enzymes, and in clinical trials of PEG-uricase and PEG-asparaginase, these anti-PEG antibodies have markedly accelerated blood clearance, abrogated clinical efficacy, and increased the risk and severity of infusion reactions. Circulating anti-PEG antibodies have also been found in individuals naïve to PEGylated materials, possibly induced by chronic exposure to free PEGs present in commonly used consumer products. High levels of such pre-existing anti-PEG antibodies have recently been linked to serious first-exposure allergic reactions to a PEGylated RNA aptamer, which led to early termination of a clinical trial.

There is a need for modifying biomolecule therapeutics to increase their circulation half-life and stability and to reduce their antigenicity or ability to bind pre-existing antibodies.

SUMMARY

In an aspect, the disclosure relates to methods of reducing the antigenicity of a molecule. The methods may include conjugating at least one branched polymer to a molecule to form a molecule-polymer conjugate, wherein the molecule comprises a polypeptide, a polynucleotide, a small molecule, or a combination thereof, wherein the branched polymer comprises a backbone and a plurality of side chains, each side chain is covalently attached to the backbone, wherein the backbone comprises at least one of an acrylate, methacrylate, acrylamide, methacrylamide, carbonate, phosphoester, oxazoline, or a combination thereof, and wherein the molecule-polymer conjugate has reduced or eliminated antigenicity compared to a control. In some embodiments, the molecule is conjugated to the backbone of the branched polymer. In some embodiments, the molecule is conjugated to the backbone of the branched polymer via a linker. In some embodiments, each side chain has a first terminal end and a second terminal end, wherein the first terminal end is covalently attached to the backbone, and wherein the second terminal end independently comprises an alkyl, ester, amine, amide, or carboxyl group. In some embodiments, each side chain has a first terminal end and a second terminal end, wherein the first terminal end is covalently attached to the backbone, and wherein the second terminal end does not include a hydroxyl group. In some embodiments, each side chain is a linear polymer. In some embodiments, at least one side chain comprises 1 monomer. In some embodiments, each side chain comprises at least 2 monomers repeated in tandem. In some embodiments, each side chain comprises less than 25 monomers repeated in tandem. In some embodiments, each side chain comprises 3 to 9 monomers repeated in tandem. In some embodiments, each side chain comprises 3 monomers repeated in tandem. In some embodiments, the monomer of each side chain is independently selected from betaine, phosphorylcholine, phosphorylethanolamine, sarcosine, ethylene glycol, or a combination thereof. In some embodiments, the betaine comprises carboxybetaine, sulfobetaine, or a combination thereof. In some embodiments, the monomer of at least one side chain comprises ethylene glycol. In some embodiments, the monomer of each side chain comprises ethylene glycol. In some embodiments, more than one branched polymer is conjugated to the molecule, each branched polymer conjugated to a different site of the molecule. In some embodiments, the molecule comprises a polypeptide, and wherein one branched polymer is conjugated to the polypeptide at a site selected from the C-terminus, the N-terminus, and an internal amino acid of the polypeptide. In some embodiments, the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

In some embodiments, the molecule comprises a polypeptide comprising a sortase A recognition site, and wherein the branched polymer and the polypeptide are incubated with sortase A under conditions to conjugate the branched polymer to the sortase recognition site of the polypeptide. In some embodiments, the molecule comprises a polypeptide comprising a sortase A recognition site, and wherein the conjugating comprises: a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate. In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the method further includes separating the molecule-polymer conjugate formed in step (b) from the unreacted macroinitiator. In some embodiments, the branched polymer is synthesized and subsequently grafted to the molecule to form the molecule-polymer conjugate. In some embodiments, the conjugating comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate. In some embodiments, the branched polymer is synthesized using free-radical polymerization. In some embodiments, the branched polymer is synthesized using at least one method selected from ionic ring-opening polymerization (ionic ROP), ring opening metathesis polymerization, ionic polymerization, condensation polymerization, and coordination polymerization.

In a further aspect, the disclosure relates to methods of making a molecule-polymer conjugate having reduced or eliminated antigenicity compared to a control, from a molecule comprising a polypeptide having a sortase A recognition site. The methods may include a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate, wherein the branched polymer comprises a backbone and a plurality of side chains, each side chain covalently attached to the backbone. In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the method further includes separating the molecule-polymer conjugate formed in step (b) from the unreacted macroinitiator, wherein the yield of molecule-polymer conjugate is at least about 50% of the total conjugates and macroinitiators which are separated. In some embodiments, the molecule-polymer conjugate is separated by chromatography. In some embodiments, the chromatography comprises size-exclusion chromatography, ion exchange chromatography, affinity chromatography, or hydrophobic interaction chromatography, or a combination thereof. In some embodiments, the chromatography comprises size-exclusion chromatography. In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization. In some embodiments, the molecule comprises a polypeptide, a polynucleotide, a small molecule, or a combination thereof.

Another aspect of the disclosure provides a molecule-polymer conjugate having reduced or eliminated antigenicity compared to a control. The molecule-polymer conjugates may include a branched polymer comprising a backbone and a plurality of side chains, each side chain covalently attached to the backbone; and a molecule conjugated to the backbone of the branched polymer, wherein the molecule comprises a polypeptide, a polynucleotide, a small molecule, or a combination thereof, wherein each side chain is a linear polymer, wherein the backbone comprises at least one of an acrylate, methacrylate, acrylamide, methacrylamide, carbonate, phosphoester, oxazoline, or a combination thereof. In some embodiments, the molecule is conjugated to the backbone of the branched polymer via a linker. In some embodiments, each side chain has a first terminal end and a second terminal end, wherein the first terminal end is covalently attached to the backbone, and wherein the second terminal end independently comprises an alkyl, ester, amine, amide, or carboxyl group. In some embodiments, each side chain has a first terminal end and a second terminal end, wherein the first terminal end is covalently attached to the backbone, and wherein the second terminal end does not include a hydroxyl group. In some embodiments, at least one side chain comprises 1 monomer. In some embodiments, each side chain comprises at least 2 monomers repeated in tandem. In some embodiments, each side chain comprises less than 25 monomers repeated in tandem. In some embodiments, each side chain comprises 3 to 9 monomers repeated in tandem. In some embodiments, each side chain comprises 3 monomers repeated in tandem. In some embodiments, the monomer of each side chain is independently selected from betaine, phosphorylcholine, phosphorylethanolamine, sarcosine, ethylene glycol, or a combination thereof. In some embodiments, the betaine comprises carboxybetaine, sulfobetaine, or a combination thereof. In some embodiments, the monomer of at least one side chain comprises ethylene glycol. In some embodiments, the monomer of each side chain comprises ethylene glycol. In some embodiments, more than one branched polymer is conjugated to the molecule, each branched polymer conjugated to a different site of the molecule. In some embodiments, the molecule comprises a polypeptide, and wherein one branched polymer is conjugated to the polypeptide at a site selected from the C-terminus, the N-terminus, and an internal amino acid of the polypeptide. In some embodiments, the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof. In some embodiments, the branched polymer comprises poly[oligo(ethylene glycol) methyl ether methacrylate] (POEGMA), and wherein the POEGMA comprises: a backbone comprising poly(methyl methacrylate); and a plurality of side chains covalently attached to the backbone, each side chain comprising at least 1 monomer of ethylene glycol (EG) repeated in tandem. In some embodiments, at least one side chain comprises 1 monomer of ethylene glycol (EG). In some embodiments, each side chain comprises at least 2 monomers of ethylene glycol (EG) repeated in tandem. In some embodiments, each side chain comprises at least 10 monomers of ethylene glycol (EG) repeated in tandem. In some embodiments, each side chain comprises less than 25 monomers of ethylene glycol (EG) repeated in tandem. In some embodiments, each side chain comprises 3 monomers of ethylene glycol (EG) repeated in tandem. In some embodiments, each side chain comprises 3 to 9 monomers of ethylene glycol (EG) repeated in tandem. In some embodiments, the molecule-POEGMA conjugate is not reactive with pre-existing anti-PEG antibodies in a subject.

In some embodiments, the molecule comprises one or more peptides or protein therapeutic agents selected from a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone, GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GHRH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1 R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor VIIa, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof. In some embodiments, the molecule comprises a polypeptide, and wherein the polypeptide comprises a His-tag, a stimulus-responsive polypeptide, or a combination thereof. In some embodiments, the stimulus-responsive polypeptide is selected from an elastin-like polypeptide, a polypeptide comprising a repeated motif, and a resilin-like polypeptide. In some embodiments, the molecule-polymer conjugate has: an in vivo half-life that is at least 25% greater compared with the in vivo half-life of the molecule itself; or an in vivo biodistribution to a tissue, organ, or disease site that is at least 25% greater than the in vivo biodistribution of the molecule itself; or a reduced binding to anti-PEG antibodies compared to a control; or a reduced immune response compared to a control; or a combination thereof. In some embodiments, the molecule-polymer conjugates have an in vivo half-life that is at least 80% greater than the in vivo half-life of the molecule itself. In some embodiments, the control comprises the molecule conjugated to a polymer that is not branched. In some embodiments, the control comprises the molecule by itself. In some embodiments, the control comprises the molecule conjugated to a linear polymer. In some embodiments, the control comprises the molecule conjugated to unbranched PEG. In some embodiments, the molecule comprises a polypeptide, and wherein at least about 20% of the polypeptides have a conjugated branched polymer solely at the C-terminus. In some embodiments, at least about 75% of the polypeptides have a conjugated branched polymer solely at the C-terminus. In some embodiments, at least about 90% of the polypeptides have a conjugated branched polymer solely at the C-terminus. In some embodiments, the yield of molecule-polymer conjugate is at least about 75%. In some embodiments, the yield of molecule-polymer conjugate is at least about 85%.

The disclosure provides for other aspects and embodiments that will be apparent in light of the following detailed description and accompanying figures.

BRIEF DESCRIPTION OF THE DRAWINGS

FIGS. 1A-1C are a synthetic scheme of exendin-C-POEGMA. FIG. 1A, recombinant expression of the sortase A substrate, exendin-srt-His$_6$-ELP, and purification by ITC. FIG. 1B, sortase-catalyzed site-specific attachment of the ATRP initiator AEBMP to the C-terminus of exendin to generate exendin-C—Br. FIG. 1C, In situ ATRP of OEGMA from exendin-C—Br yielding exendin-C-POEGMA. ITC: inverse transition cycling, ELP: elastin-like polypeptide, srt: sortase A recognition sequence "LPETG" (SEQ ID NO: 2), AEBMP: N-(2-(2-(2-(2-aminoacetamido)acet-amido)acet-amido) ethyl)-2-bromo-2-methylpropanamide. Images from the RCSB PDB (www.rcsb.org) of: PDB ID 1T2P (sortase A); PDB ID 1JRJ (exendin-4).

FIG. 2A, coomassie-stained SDS-PAGE analysis of initiator attachment on exendin by sortase A. Lane 1: MW marker, lane 2: sortase reaction mixture after 18 h of reaction, lane 3: purified exendin-C—Br macroinitiator. FIG. 2B, SEC traces of ATRP reaction mixtures of grafting EG9 POEGMA from exendin-C—Br carried out for 0.5 h, 1 h, 1.25 h, 2 h and 3 h, detected by UV-vis absorbance at 280 nm. FIG. 2C, cyclic adenosine monophosphate (cAMP) response of native exendin and EG9 exendin-C-POEGMA conjugates with $M_n$s of 25.4 kDa, 54.6 kDa, 66.2 kDa, 97.2 kDa and 155.0 kDa in baby hamster kidney (BHK) cells expressing the GLP-1R. Results are plotted as mean±standard error of the mean (SEM), n=3. Half-maximal effective concentration ($EC_{50}$) values are summarized in TABLE 1.

FIG. 3F, area under the curve (AUC) of blood glucose profiles (0 h to 144 h, with respect to 0% baseline) as a function of conjugate $M_n$. AUCs were compared using one-way ANOVA followed by post hoc Tukey's multiple comparison test. In all panels, results are plotted as mean ±SEM,n=6, *P<0.05, P<0.01, *P<0.001 and ****P<0.0001.

FIG. 5A, direct ELISA probing 54.6 kDa EG9 exendin-C-POEGMA conjugate, native exendin, adenosine deaminase (ADA), bovine serum albumin (BSA), Krystexxa® (PEG-uricase) and Adagen® (PEG-ADA) with diluent (1% BSA in PBS), an anti-PEG negative patient plasma sample, or one of two anti-PEG positive plasma samples. FIG. 5B, competitive ELISA, where various amounts of exendin, 54.6 kDa EG9 exendin-C-POEMGA, ADA and Adagen® were allowed to compete with Krystexxa® for binding with anti-PEG antibodies in a positive plasma sample. FIGS. 5C and 5D, direct and competitive assays described in panels a and b performed with a 55.6 kDa EG3 exendin-C-POEGMA conjugate. In all assays, the same unmodified peptide/protein content or similar PEG/OEG content in the case of polymer-modified samples per well were compared. See Methods section for details. Results are plotted as mean±SEM, n=3 in panels a and b, n=5 in panels c and d. Data were analyzed by two-way ANOVA, followed by post hoc Dunnett's multiple comparison test (P<0.01, and **P <0.0001).

FIG. 6C, Exendin and FIG. 6D, exendin-C-POEGMA conjugates (54.6 kDa EG9, 55.6 kDa EG3 and 71.6 kDa EG3) were fluorescently labeled with Alexa Fluor® 488 and injected into mice (n=3) s.c. at 75 nmol/kg (45 nmol/kg fluorophore). Blood samples were collected via tail vein at various time points for fluorescence quantification. Data were analyzed using a non-compartmental fit (solid lines) to derive the pharmacokinetic parameters shown in TABLE 2. Results in all panels are plotted as mean±SEM.

FIG. 7B, $His_6$-sortase A purification by immobilized metal affinity chromatography (IMAC). Lane 1: marker, lane 2: E. coli lysate, lanes 3 and 4: first and second elution washes with imidazole (yield: ~400 mg/L of culture). $His_6$: hexahistidine.

FIG. 9A, SEC traces of ATRP reaction mixtures of grafting EG9 POEGMA from the exendin-C—Br macroinitiator carried out for various times with RI detection. Due to its small size and low concentration, the signal from the residual exendin-C—Br was too low to be observed by RI detection. FIG. 9B, coomassie-stained SDS-PAGE analysis of EG9 exendin-C-POEGMA conjugates purified by a single round of preparative SEC. Lane 1: marker, from left to right in lanes 2-6: purified 155.0 kDa, 97.2 kDa, 66.2 kDa, 54.6 kDa and 25.4 kDa EG9 conjugates.

FIG. 10C, overlaid weight profiles for all treatment and control groups. Weights are reported as % change from 0 h time point. Results in all panels are plotted as mean±SEM.

FIG. 11A, normalized and FIG. 11B, un-normalized blood glucose profiles of fed mice (n=6) that received a single s.c. injection of unmodified exendin administered at 25 nmol/kg, compared to PBS control at equivalent volume injected at t=0 h. Blood glucose levels in panel a were normalized to the average glucose levels measured 24 h prior to and immediately before injection. Results are plotted as mean±SEM.

FIG. 12C, overlaid weight profiles for all treatment and control groups. Weights are reported as % change from 0 h time point. Weights were not measured for the exendin group at t=144 h. Results in all panels are plotted as mean±SEM.

FIG. 16A, isotopic distribution of C-terminal peptide [NGGPSSGAPPPSLPET-"AEBMP", SEQ ID NO: 8]$^{2+}$ detected by LC/MS-MS after trypsin digestion of exendin-C—Br. FIG. 16B, theoretical isotopic distribution of C-terminal peptide of exendin-C—Br after trysin digestion generated by Molecular Mass Calculator software (Pacific Northwest National Laboratory).

FIG. 17C, coomassie-stained SDS-PAGE analysis of EG3 exendin-C-POEGMA conjugates purified by a single round of preparative SEC. Lane 1: marker, from left to right in lanes 2-4: purified 26.3, 55.6 and 71.6 kDa EG3 conjugates.

DETAILED DESCRIPTION

Figure 1C:
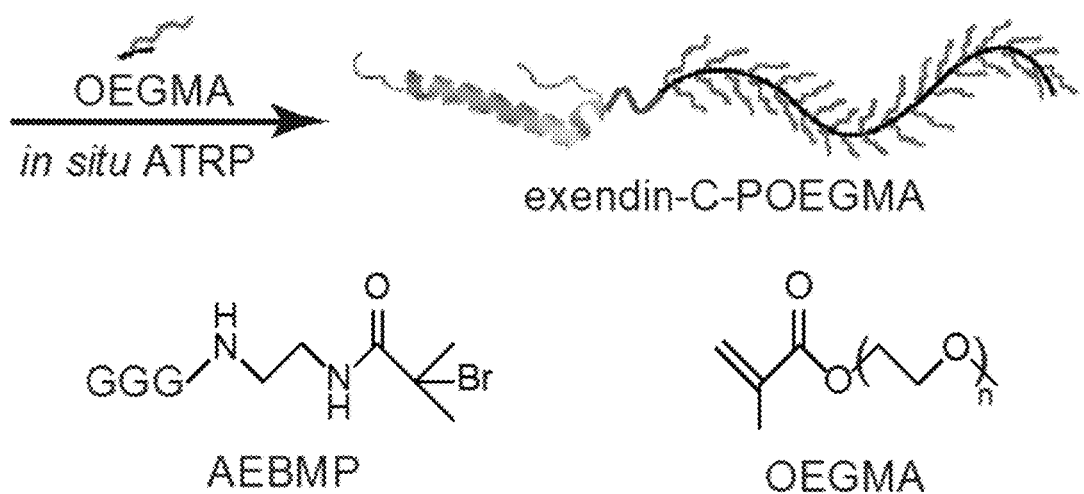

Described herein are methods of reducing or eliminating the antigenicity of a molecule by conjugating a branched polymer thereto to form a molecule-polymer conjugate. The branched polymer may be conjugated to the molecule by a variety of ways. As detailed herein, sortase-catalyzed polymer conjugation may be used to generate a molecule-polymer conjugate. This strategy exploits the C-terminal native peptide ligation mechanism of the enzyme sortase A. Breaking up and appending PEG as short oligomeric side-chains of optimized length on the conjugated POEGMA not only retains the long circulation of the POEGMA conjugates, but also eliminates their reactivity toward patient-derived PEG antibodies. These results demonstrate that the architecture of PEG appended to a molecule plays a role in modulating its antigenicity. The compositions and methods detailed here may be used to deliver molecules with reduced or eliminated antigenicity, and thereby address the growing prevalence of pre-existing anti-PEG antibodies in the general population that is increasingly undermining the safety and efficacy of PEGylated therapeutics.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Antigen" refers to a molecule capable of being bound by an antibody or a T cell receptor. The term "antigen", as used herein, also encompasses T-cell epitopes. An antigen is additionally capable of being recognized by the immune system and/or being capable of inducing a humoral immune response and/or cellular immune response leading to the activation of B-lymphocytes and/or T-lymphocytes. In some embodiments, the antigen contains or is linked to a Th cell epitope. An antigen can have one or more epitopes (B-epitopes and T-epitopes). Antigens may include polypeptides, polynucleotides, carbohydrates, lipids, small molecules, and combinations thereof. Antigens may also be mixtures of several individual antigens. "Antigenicity" refers to the ability of an antigen to specifically bind to a T cell receptor or antibody and includes the reactivity of an antigen toward pre-existing antibodies in a subject. "Immunogenicity" refers to the ability of any antigen to induce an immune response and includes the intrinsic ability of an antigen to generate antibodies in a subject. As used herein, the terms "antigenicity" and "immunogenicity" are different and not interchangeable.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a molecule, or sample comprising a molecule, without having a branched polymer conjugated thereto. A control may be a molecule, or sample comprising a molecule, with a polymer, that is different from a branched polymer as detailed herein, conjugated thereto. A control may be a subject, or a sample therefrom, whose disease state is known. The subject, or sample therefrom, may be healthy, diseased, diseased prior to treatment, diseased during treatment, or diseased after treatment, or a combination thereof. The control may include, for example, the molecule alone or by itself, the molecule conjugated to a different polymer, the molecule conjugated to a non-branched polymer or to a polymer that is not branched, the molecule conjugated to PEG, the molecule conjugated to unbranched PEG, the molecule directly conjugated to a linear polymer, or the molecule conjugated to a side chain directly (without a branched polymer).

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

"Opsonization" refers to the molecular mechanism whereby molecules, microbes, or apoptotic cells are chemically modified to have stronger interactions with cell surface receptors on phagocytes and natural killer (NK) cells. An antigen on the molecules, microbes, or apoptotic cell is coated in opsonins. The opsonins enhance binding to immune cells such as macrophages and neutrophils. Opsonization also mediates phagocytosis via signal cascades from cell surface receptors.

"Polymer" or "synthetic polymer" refers to a polymer which is produced from at least one monomer by a chemical process. A synthetic polymer is not produced directly by a living organism. Synthetic polymers include a homopolymer, heteropolymer, block polymer, co-polymer, ter-polymer, etc., and blends, combinations and mixtures thereof. Examples of synthetic polymers include, but are not limited to, functionalized polymers, such as a polymer comprising 5-vinyltetrazole monomer units and having a molecular weight distribution less than 2.0. A synthetic polymer may be or contain one or more of a star block copolymer, a linear polymer, a branched polymer, a hyperbranched polymer, a dendritic polymer, a comb polymer, a graft polymer, a brush polymer, a bottle-brush copolymer and a crosslinked structure, such as a block copolymer comprising a block of 5-vinyltetrazole monomer units. Synthetic polymers include, without limitation, polyesters, poly(meth)acrylamides, poly(meth)acrylates, polyethers, polystyrenes, polynorbornenes and monomers that have unsaturated bonds. For example, amphiphilic comb polymers are described in U.S. Patent Application Publication No. 2007/0087114 and in U.S. Pat. No. 6,207,749 to Mayes et al., the disclosure of each of which is herein incorporated by reference in its entirety. The amphiphilic comb-type polymers may be present in the form of copolymers, containing a backbone formed of a hydrophobic, water-insoluble polymer and side chains formed of short, hydrophilic non-cell binding polymers. Examples of other synthetic polymers include, but are not limited to, polyalkylenes such as polyethylene and polypropylene and polyethyleneglycol (PEG); polychloroprene; polyvinyl ethers; such as poly(vinyl acetate); polyvinyl halides such as poly(vinyl chloride); polysiloxanes; polystyrenes; polyurethanes; polyacrylates; such as poly(methyl (meth)acrylate), poly(ethyl (meth)acrylate), poly(n-butyl(meth)acrylate), poly(isobutyl (meth) acrylate), poly(tert-butyl (meth)acrylate), poly(hexyl(meth) acrylate), poly(isodecyl (meth)acrylate), poly(lauryl (meth) acrylate), poly(phenyl (meth)acrylate), poly(methyl acrylate), poly(isopropyl acrylate), poly(isobutyl acrylate), and poly(octadecyl acrylate); polyacrylamides such as poly (acrylamide), poly(methacrylamide), poly(ethyl acrylamide), poly(ethyl methacrylamide), poly(N-isopropyl acrylamide), poly(n, iso, and tert-butyl acrylamide); and copolymers and mixtures thereof. These synthetic polymers may include useful derivatives, including synthetic polymers having substitutions, additions of chemical groups, for example, alkyl groups, alkylene groups, hydroxylations, oxidations, and other modifications routinely made by those skilled in the art. The synthetic polymers may include zwitterionic polymers such as, for example, polyphosphorycholine, polycarboxybetaine, and polysulfobetaine. The synthetic polymers may have side chains of betaine, carboxybetaine, sulfobetaine, oligoethylene glycol (OEG), sarcosine or polyethyleneglycol (PEG).

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids.

"Pharmacokinetics" as used herein refers the circulation of a drug or molecule in the body and its bioavailability, distribution, and excretion.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all "Sample" or "test sample" as used herein can mean any sample in which the presence and/or level of a target is to be detected or determined or any sample comprising a molecule or conjugate as described herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sortase" refers to a polypeptide that recognizes a sortase recognition site in a protein and cleaves a peptide bond therein, forming a stable intermediate that joins the catalytic thiol of sortase to the carboxyl group of an amino acid within the recognition site via a thioester bond. This intermediate undergoes nucleophilic attack by the a-amino group of an oligoglycine branch in the peptidoglycan, generating a native peptide bond that anchors the substrate protein to the cell wall. Sortase A (SrtA) may recognize a sortase A recognition site, such as an amino acid sequence consisting of LPXZG (SEQ ID NO: 3, where X and Z are independently any amino acid) and cleave the peptide bond between the Z amino acid and the glycine of LPXZG and form a thioester bond between the catalytic thiol in SrtA and the carboxyl group of the Z amino acid. The thioester bond between the catalytic thiol in SrtA and the carboxyl group of the Z amino acid forms an intermediate, and the intermediate undergoes nucleophilic attack by the ε-amino group of the lysine of first polypeptide to form an isopeptide bond between the ε-amino group of the lysine and the Z amino acid of LPXZG. In some embodiments, SrtA forms an isopeptide bond between the ε-amino group of any solvent-accessible, nucleophilic lysine of the first polypeptide and the Z amino acid of LPXZG. In some embodiments, the sortase A recognition site includes LPXTG (SEQ ID NO: 1, where X is any amino acid). The SrtA may be any SrtA, such as *Staphylococcus aureus* SrtA. SrtA may be from a Gram positive bacterium, such as, for example, bacteria in a genus selected from *Staphylococcus, Streptococcus, Enterococcus, Bacillus, Corynebacterium, Nocardia, Clostridium, Actinobacteria*, and *Listeria*. In some embodiments, SrtA is from *S. aureus*. The SrtA may be wild-type SrtA or a variant thereof. Sortase is further detailed in International Patent Application No. PCT/US2015/017601,filed Feb. 25, 2015, published as WO 2015/130846, and International Patent Application No. PCT/US2014/040319, filed May 30, 2014, published as WO 2014/194244, which are incorporated herein by reference.

"Stealth" or "stealth polymer" refers to a molecule-polymer conjugate, or to the polymer thereof, that can remain undetected by immune cells in the bloodstream for a prolonged period of time. Stealth molecule-polymer conjugates are at least partially resistant to enzymatic degradation of the conjugate, or to the polypeptide thereof, such as by proteases, and opsonization, which is a common method used by immune system to recognize foreign particles. Accordingly, stealth molecule-polymer conjugates may have one or more of reduced antigenicity, reduced immunogenicity, increased stability, increased half-life, and increased bioavailability relative to other polymers, conjugates, non-stealth polymers, and/or non-stealth conjugates. The ability to delay, reduce, or prevent opsonization, recognition by the immune system, or clearance of a conjugate (or the polypeptide or molecules thereof) from the body may be referred to herein as a stealth property.

"Subject" as used herein can mean a mammal that wants or is in need of the herein described conjugates. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Target" as used herein can refer to an entity that a molecule binds. A target may include, for example, a small molecule, a protein, a polypeptide, a polynucleotide, a carbohydrate, or a combination thereof.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

The term "acyl" or "carbonyl" refers to the group —C(O)R wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents. For example, when R is alkyl, such a group may be referred to as an alkylcarbonyl group.

The term "alkoxy" refers to the group —O—R wherein R is alkyl, alkenyl, alkynyl, cycloalkyl or heterocyclyl, any of which may be optionally substituted, e.g., with one or more substituents.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl. An aromatic amine is an aryl group substituted with one or more amino groups. An aromatic alcohol is an aryl group substituted with one or more hydroxyl groups. Both aromatic amines and aromatic alcohols may be further substituted with other substitutents.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "carboxyl" refers to the group —C(=O)OR, wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl any of which may be optionally substituted, e.g., with one or more substituents.

The term "carboxylate" refers to the group —C(=O)O$^{(-)}$.

The term "carbonylamino" or "amido" refers to the group —C(O)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl, and heterocyclylalkyl, or R' and R" together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

The term "amide" refers to the group —C(O)NR wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents.

The term "amine" refers to the group —NH$_2$.

The term "cycloalkyl" as used herein refers to nonaromatic, saturated or partially unsaturated cyclic, bicyclic, tricyclic or polycyclic hydrocarbon groups having 3 to 12 carbons (e.g., 3, 4, 5, 6, or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "ester" refers to the group —C(O)OR wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents.

The term "halo" or "halogen" as used herein refers to any radical of fluorine, chlorine, bromine or iodine.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical. The term "haloalkoxy" refers to an —O-haloalkyl radical.

Where chemical groups are specified by their conventional chemical formulae, written from left to right, they optionally encompass substituents resulting from writing the structure from right to left, e.g., —CH$_2$O— optionally also recites —OCH$_2$—.

2. Conjugate

Provided herein is a molecule-polymer conjugate. The molecule-polymer conjugate includes a branched polymer and a molecule covalently attached thereto. The molecule-polymer may include more than one branched polymer conjugated to the molecule. In some embodiments, more than one branched polymer is conjugated to the molecule, each branched polymer conjugated to a different site of the molecule.

a. Branched Polymer

The branched polymer includes a backbone and a plurality of side chains. Each side chain is covalently attached to the backbone. The branched polymer may include any branched, non-linear structure with a backbone and side chains. For example, the branched polymer includes structures such as a brush polymer, a comb polymer, a star polymer, a dendrimer, or a hyperbranched polymer. Brush polymers may have four-way branch points where the backbone and side chain connect. Comb polymers may have three-way branch points where the backbone and side chain connect. The backbone may be a single point for star polymers, hyperbranched polymers, and dendrimers. Star polymers may have a single point (backbone) to which multiple side chains are connected. Hyperbranched polymers and dendrimers are both repetitively branched polymers, wherein the side chains originate from a single point. Dendrimers may be symmetrical with the same side chains at each branch, whereas hyperbranched polymers may have side chains of random and/or irregular lengths and sizes one or more branches. In some embodiments, the branched polymer comprises poly[oligo(ethylene glycol) methyl ether methacrylate] (POEGMA).

i) Backbone

The backbone comprises any suitable polymer. In some embodiments, the backbone comprises a linear polymer. In some embodiments, the backbone comprises at least one of an acrylate, methacrylate, acrylamide, methacrylamide, carbonate, phosphoester, oxazoline, or a combination thereof. In some embodiments, the backbone comprises poly(methyl methacrylate). The molecule may be conjugated to the backbone of the branched polymer.

ii) Side Chains

The side chains are polymers, each side chain covalently attached to the backbone. In some embodiments, the side chain is a linear polymer. In some embodiments, the side chain is a linear oligomer. In some embodiments, an oligomer is a polymer comprising 25 monomers or less. In some embodiments, each side chain is a linear polymer. In some embodiments, each side chain is an oligomer. In some embodiments, a side chain is a block copolymer comprising two or more oligomers in tandem, wherein the monomers of each oligomer are the same. Each side chain includes at least 1 monomer. The monomers of a single side chain may be the same. The monomers of a single side chain may be different from each other. The monomer of each side chain may be independently selected from at least one of a betaine, phosphorylcholine, phosphorylethanolamine, sarcosine, ethylene glycol, or a combination thereof. The betaine may be any betaine in the art. For example, the betaine may comprise carboxybetaine, sulfobetaine, or a combination thereof.

Each side chain may include about 1 to 20 monomers, about 2 to 20 monomers, about 3 to 20 monomers, about 3 to 9 monomers, about 4 to 20 monomers, about 5 to 20 monomers, about 8 to 20 monomers, about 3 to 10 monomers, about 3 to 9 monomers, or about 3 to 5 monomers repeated in tandem. Each side chain may include at least 3 monomers, at least 4 monomers, at least 5 monomers, at least 6 monomers, at least 7 monomers, at least 8 monomers, at least 9 monomers, or at least 10 monomers repeated in tandem. Each side chain may include less than 25 monomers, less than 20 monomers, less than 15 monomers, less than 10 monomers, less than 9 monomers, less than 8 monomers, less than 7 monomers, less than 6 monomers, less than 5 monomers, less than 4 monomers, or less than 3 monomers repeated in tandem. In some embodiments, each side chain comprises at least 2 monomers repeated in tandem. In some embodiments, each side chain comprises less than 25 monomers repeated in tandem. In some embodiments, each side chain comprises at least 3 monomers repeated in tandem. In some embodiments, each side chain comprises 3 monomers repeated in tandem.

In some embodiments, the monomer of at least one side chain comprises ethylene glycol. In some embodiments, the monomer of each side chain comprises ethylene glycol. In some embodiments, each side chain includes at least 2 monomers of ethylene glycol (EG) repeated in tandem. In some embodiments, each side chain comprises at least 10 monomers of ethylene glycol (EG) repeated in tandem. In some embodiments, each side chain comprises less than 25 monomers of ethylene glycol (EG) repeated in tandem. In some embodiments, each side chain comprises 3 monomers of ethylene glycol (EG) repeated in tandem. In some embodiments, each side chain comprises 3 to 9 monomers of ethylene glycol (EG) repeated in tandem. Adjacent side chains may be the same. Adjacent side chains may be different from each other.

Each side chain has a first terminal end and a second terminal end. The first terminal end is covalently attached to the backbone. The second terminal end is free. In some embodiments, the second terminal end independently comprises an alkyl, ester, amine, amide, or carboxyl group. In some embodiments, the second terminal end of each side chain does not include a hydroxyl group.

In some embodiments, the terminal end of each side chain individually comprises an ester, amine, amide, alkyl, or carboxyl. In some embodiments, the terminal end of each side chain does not include a hydroxyl group. The terminal end may be modified. The terminal end may be natural or unmodified. The terminal end of each side chain may be the same or different from the terminal end of an adjacent side chain. In some embodiments, the terminal end of each side chain is the same as the terminal end of an adjacent side chain. In some embodiments, the terminal end of each side chain is different from the terminal end of an adjacent side chain.

b. Molecule

The molecule may include any suitable molecule whose antigenicity is to be reduced or eliminated. The molecule may be selected from a nucleotide, polynucleotide, protein, peptide, polypeptide, carbohydrate, lipid, small molecule, or a combination thereof. In some embodiments, the molecule comprises a polypeptide, a polynucleotide, a small molecule, or a combination thereof. In some embodiments, the molecule comprises one or more peptides or protein therapeutic agents. In some embodiments, the molecule comprises a polypeptide. In some embodiments, the molecule comprises a small molecule. In some embodiments, the molecule comprises a protein. In some embodiments, the molecule comprises a drug. In some embodiments, the molecule comprises a therapeutic. In some embodiments, the molecule comprises a cancer therapeutic. In some embodiments, the molecule comprises an antibody. In some embodiments, the molecule comprises exendin.

The molecule may include, for example, a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone, GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GHRH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1 R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor VIIa, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof.

The molecule may include a sortase A recognition site, a His-tag, stimulus-responsive polypeptide, or a combination thereof. Stimulus-responsive polypeptides may include environmentally responsive polypeptides. The stimulus-responsive polypeptide may include, for example, an elastin-like polypeptide, a polypeptide comprising a repeated motif (as disclosed in, for example, US 2015/0112022, filed Dec. 16, 2014, and incorporated herein by reference), or a resilin-like polypeptide, or a combination thereof. In some embodiments, the molecule comprises a polypeptide comprising a sortase A recognition site. In some embodiments, the sortase A recognition site comprises LPXTG (SEQ ID NO: 1), wherein X is any amino acid.

The branched polymer may be conjugated to any site anywhere on the molecule. For example, when the molecule comprises a polypeptide, the branched polymer may be conjugated to the polypeptide at the C-terminus, the N-terminus, or an internal amino acid, or a combination thereof. In some embodiments, the molecule comprises a polypeptide with the branched polymer conjugated to the C-terminus of the polypeptide. One branched polymer may be conjugated to the molecule. More than one branched polymer may be conjugated to the molecule, each branched polymer conjugated to a different site of the molecule. In some embodiments, the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof. At least about 50%, at least about 55%, at least about 60%, at least about 65%, at least about 70%, at least about 75%, at least about 80%, at least about 85%, at least about 90%, or at least about 95% of the polypeptides have a conjugated polymer initiated solely from the C-terminus. In some embodiments, at least about 50% of the polypeptides have a conjugated polymer initiated solely from the C-terminus. In some embodiments, at least about 75% of the polypeptides have a conjugated polymer initiated solely from the C-terminus. In some embodiments, at least about 90% of the polypeptides have a conjugated polymer initiated solely from the C-terminus.

c. Conjugate Properties

The conjugates may have an altered pharmacological property compared to a control. The property may include, for example, reduced antigenicity, eliminated antigenicity, reduced opsonization of the molecule, reduced binding to anti-PEG antibodies, a reduced immune response, lack of reactivity with pre-existing anti-PEG antibodies in a subject, an in vivo half-life that is at least 25% greater, or an in vivo biodistribution to a tissue, organ, or disease site that is at least 25% greater, compared to a control.

In some embodiments, the conjugates have an in vivo half-life that is at least 25% greater compared with the in vivo half-life of the molecule alone or other molecule-polymer conjugates; or an in vivo biodistribution to a tissue, organ, or disease site that is at least 25% greater than the in vivo biodistribution of the molecule alone or other molecule-polymer conjugates. In some embodiments, the antigenicity of the conjugate is reduced compared to the molecule alone or to the molecule conjugated to the linear polymer. In some embodiments, the conjugates have reduced antigenicity compared to other molecule-polymer conjugates. In some embodiments, the conjugates have reduced binding to anti-PEG antibodies compared to other molecule-polymer conjugates or molecules. In some embodiments, the conjugates induce a reduced immune response compared to other molecule-polymer conjugates or molecules. In some embodiments, the conjugate is not reactive with pre-existing anti-PEG antibodies in a subject. In some embodiments, the conjugates have an in vivo half-life that is at least 25% greater compared with the in vivo half-life of the molecule. In some embodiments, the conjugates have an in vivo biodistribution to a tissue, organ, or disease site that is at least 25% greater than the in vivo biodistribution of the molecule. In some embodiments, the conjugates have an in vivo half-life that is at least 80% greater than the in vivo half-life of the molecule. In some embodiments, the branched polymer comprises POEGMA, and the molecule-polymer conjugate is not reactive with pre-existing anti-PEG antibodies in a subject.

The methods detailed herein may enable control over site and stoichiometry of conjugation of the branched polymer to the molecule. The methods detailed herein may enable a high degree of molecular weight tunability and low dispersity of the branched polymer conjugated to the molecule, which may translate to a more predictable therapeutic performance relative to other polymer conjugates of therapeutic biomolecules. The molecule-polymer conjugates detailed herein may be more homogenous than conventional PEGylated molecules, in terms of the conjugation site, the molecular weight of the branched polymer, or a combination thereof.

The molecule-polymer conjugates detailed herein may facilitate less frequent administration, prevent an undesirable peak-to-valley fluctuation of the drug concentration in vivo, increase patient compliance, and reduced treatment cost, or a combination thereof.

3. Synthesis of the Conjugate

Methods of making the conjugate may include, for example, those detailed in International Patent Application No. PCT/US2014/040319, filed May 30, 2014, published as WO 2014/194244, which is incorporated herein by reference.

In some embodiments, the molecule is conjugated to the backbone of the branched polymer via a linker. The molecule may be conjugated to the backbone of the branched polymer via more than one linker. The molecule may be conjugated to the backbone of the branched polymer via at least 1, at least 2, at least 3, at least 4, at least 5, at least 6, at least 7, at least 8, at least 9, or at least 10 linkers. The molecule may be conjugated to the backbone of the branched polymer via less than 20, less than 15, less than 10, or less than 5 linkers. The molecule may be conjugated to the backbone of the branched polymer via between 1 and 20, between 5 and 15, or between 1 and 5 linkers. The linker may be a polypeptide of any amino acid sequence and length. The linker may act as a spacer peptide. In some embodiments, the linker comprises charged amino acids. In some embodiments, the linker comprises uncharged amino acids. In some embodiments, the linker is flexible. In some embodiments, the linker comprises one or more cysteines. In some embodiments, the linker comprises an amino acid sequence selected from SEQ ID NO: 4 (GGC), SEQ ID NO: 5 ((GGC)$_8$), SEQ ID NO: 6 ((G$_4$S)$_3$), and SEQ ID NO: 7 ((VPGXG)$_{16}$ wherein X is valine or cysteine present in a ratio of 1:1). The linker may serve as an attachment site for the molecule to the branched polymer. The molecule may attach to the linker by any suitable means known in the art. The molecule may attach to the linker through a thiol reactive linking group. In some embodiments, the molecule is attached to one or more branched polymers via the linker. In some embodiments, the molecule is attached to the branched polymer through a thiol reactive group in the linker.

The conjugate may be made by joining or conjugating a branched polymer to a polypeptide with a sortase. In some embodiments, the molecule comprises a polypeptide that includes a sortase A recognition site, and the branched polymer and the polypeptide are incubated with Sortase A under conditions to conjugate the branched polymer to the sortase A recognition site of the polypeptide. In some embodiments, the conjugating includes contacting the molecule with a sortase A and an initiator agent under conditions that permit attachment of the initiator agent to the sortase A recognition site to form a macroinitiator, and incubating the macroinitiator with a monomer under conditions that permit free-radical polymerization and formation of a branched polymer to occur from the initiator agent to form the molecule-polymer conjugate. In some embodiments, the macroinitiator and monomer are incubated with a catalyst. The monomer may include at least one of an acrylate, methacrylate, acrylamide, and methacrylamide.

In some embodiments, the branched polymer is synthesized and subsequently grafted to the molecule to form the molecule-polymer conjugate. In some embodiments, the branched polymer is synthesized using free-radical polymerization. In some embodiments, the branched polymer is synthesized using at least one method selected from ionic ring-opening polymerization (ionic ROP), ring opening metathesis polymerization, ionic polymerization, condensation polymerization, and coordination polymerization.

In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

The yield of molecule-polymer conjugates may be at least about 50%, at least about 55%, at least about 60%, at least about 65%, at least about 70%, at least about 75%, at least about 80%, at least about 85%, at least about 90%, or at least about 95%. In some embodiments, the yield of molecule-polymer conjugates is at least about 75%. In some embodiments, the yield of molecule-polymer conjugates is at least about 85%.

In some embodiments wherein the molecule comprises a polypeptide, at least about 20% of the polypeptides have a conjugated branched polymer solely at the C-terminus. At least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the polypeptides have a conjugated branched polymer solely at the C-terminus.

In some embodiments, the molecule-polymer conjugates are separated by chromatography, such as size-exclusion chromatography, ion exchange chromatography, affinity chromatography, or hydrophobic interaction chromatography, or a combination thereof. In some embodiments, the chromatography comprises size-exclusion chromatography.

4. Administration

A composition may comprise the conjugate. The conjugates as detailed above can be formulated into a composition in accordance with standard techniques well known to those skilled in the pharmaceutical art. The composition may be prepared for administration to a subject. Such compositions comprising a conjugate can be administered in dosages and by techniques well known to those skilled in the medical arts taking into consideration such factors as the age, sex, weight, and condition of the particular subject, and the route of administration.

The conjugate can be administered prophylactically or therapeutically. In prophylactic administration, the conjugate can be administered in an amount sufficient to induce a response. In therapeutic applications, the conjugates are administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The conjugate can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The conjugate can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The conjugates can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the conjugate is administered intravenously, intraarterially, or intraperitoneally to the subject.

The conjugate can be a liquid preparation such as a suspension, syrup, or elixir. The conjugate can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The conjugate may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat.

Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the conjugate is administered in a controlled release formulation. The conjugate may be released into the circulation or a tumor, for example. In some embodiments, the conjugate may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

5. Methods a. Methods of Reducing the Antigenicity of a Molecule

Provided herein are methods of reducing the antigenicity of a molecule. The methods may include conjugating at least one branched polymer to a molecule to form a molecule-polymer conjugate, as detailed herein.

In some embodiments, the molecule comprises a polypeptide comprising a sortase A recognition site, and the branched polymer and the polypeptide are incubated with sortase A under conditions to conjugate the branched polymer to the sortase A recognition site of the polypeptide. In some embodiments, the molecule comprises a polypeptide comprising a sortase A recognition site, and the conjugating includes (a) contacting the molecule with a sortase A and an initiator agent under conditions that permit attachment of the initiator agent to the sortase A recognition site to form a macroinitiator; and (b) incubating the macroinitiator with a monomer under conditions that permit free-radical polymerization and formation of a branched polymer to occur from the initiator agent to form the molecule-polymer conjugate. In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the method further includes separating the molecule-polymer conjugate formed in step (b) from the unreacted macroinitiator.

The methods may further include separating the molecule-polymer conjugate formed in step (b) from the unreacted macroinitiator. In some embodiments, the yield of molecule-polymer conjugate is at least about 50% of the total conjugates and macroinitiators which are separated. In some embodiments, the molecule-polymer conjugate is separated by chromatography. In some embodiments, chromatography comprises size-exclusion chromatography, ion exchange chromatography, affinity chromatography, or hydrophobic interaction chromatography, or a combination thereof. In some embodiments, the chromatography comprises size-exclusion chromatography.

In some embodiments, the branched polymer is synthesized and subsequently grafted to the molecule to form the molecule-polymer conjugate. In some embodiments, the branched polymer is synthesized using free-radical polymerization. In some embodiments, the branched polymer is synthesized using at least one method selected from ionic ring-opening polymerization (ionic ROP), ring opening metathesis polymerization, ionic polymerization, condensation polymerization, and coordination polymerization.

In some embodiments, conjugating at least one branched polymer to a molecule to form a molecule-polymer conjugate comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate. In some embodiments, the macroinitiator and monomer are incubated with a catalyst. In some embodiments, the monomer comprises at least one of an acrylate, methacrylate, acrylamide, and methacrylamide. In some embodiments, the method further includes separating the molecule-polymer conjugate from the unreacted macroinitiator.

In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

b. Methods of Making Molecule-Polymer Conjugates

Provided herein are methods of making molecule-polymer conjugates having reduced or eliminated antigenicity compared to a control. The molecule may include a polypeptide having a sortase A recognition site. The method may include (a) contacting the molecule with a sortase A and an initiator agent under conditions that permit attachment of the initiator agent to the sortase A recognition site to form a macroinitiator; and (b) incubating the macroinitiator with a monomer under conditions that permit free-radical polymerization to occur from the initiator agent to form the molecule-polymer conjugate.

In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization. In some embodiments, the free-radical polymerization comprises at least one of ionic ring-opening polymerization (ionic ROP), ring opening metathesis polymerization, ionic polymerization, condensation polymerization, and coordination polymerization.

In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

The methods may further include separating the molecule-polymer conjugate formed in step (b) from the unreacted macroinitiator. In some embodiments, the yield of molecule-polymer conjugate is at least about 50% of the total conjugates and macroinitiators which are separated. In some embodiments, the molecule-polymer conjugate is separated by chromatography. In some embodiments, chromatography comprises size-exclusion chromatography, ion exchange chromatography, affinity chromatography, or hydrophobic interaction chromatography, or a combination thereof. In some embodiments, the chromatography comprises size-exclusion chromatography.

6. Examples

EXAMPLE 1

Materials and Methods

Experimental Design. All in vitro and in vivo experiments include suitable controls; where applicable, PBS served as a negative control and unmodified exendin served as a positive control. The sample sizes for in vivo studies were chosen based on similar studies conducted previously (Amiram, M., et al. *Proc. Natl. Acad. Sci.* 2013, 110, 2792-2797, Schellenberger, V., et al. *Nat. Biotechnol.* 2009, 27, 1186-1188). See Animal studies section below for details on the animal model used. Mice were randomly grouped before initiation of each experiment. The investigator was not blinded to group allocation. For the in vivo fed glucose measurement studies, mouse blood glucose levels were measured until all experimental groups no longer showed statistical significance in glucose reduction compared to the PBS control group. All collected data points were included in data analysis.

Cloning, expression and purification. All molecular biology reagents were purchased from New England Biolabs unless otherwise specified. The gene encoding exendin in a pMA-T vector was codon optimized and synthesized by Life Technologies. The first methionine residue encoding the translational start codon in proteins recombinantly expressed in *E. coli* needs to be cleaved post-translationally for proper function and stability of the protein. However, the first amino acid of exendin is a histidine, and our past experience and reports in the literature both suggest that having histidine as the residue immediately following methionine prevents proper methionine cleavage. Thus, a di-alanine leader was incorporated at the N-terminus of the peptide to facilitate methionine cleavage. Once in vivo, the di-alanine leader can be cleaved by dipeptidyl peptidase 4 (DPP4), an exopeptidase that cleaves N-terminal dipeptides containing proline or alanine as the second residue, to reveal the N-terminus of exendin for GLP-1R binding. The exendin gene was amplified by polymerase chain reaction (PCR), using forward and reverse primers containing NdeI overhangs and with the sequence for the sortase A recognition motif "LPETG" (named "srt" for brevity) followed by a $His_6$-tag incorporated in the reverse primer. The amplified "exendin-srt-$His_6$" fragment was inserted into a modified pET-24a+ vector at an NdeI restriction site immediately upstream of an ELP with the sequence $(VPGVG)_{60}$, to yield "exendin-srt-$His_6$-ELP".

Expression and purification of the quaternary fusion protein followed previously described procedures with minor changes (Qi, Y., et al. *Macromol. Rapid Commun.* 2013, 34, 1256-1260). Briefly, cells were cultured in Terrific Broth (TB, Mo Bio Laboratories, Inc.) supplemented with 45 µg/mL of kanamycin at 25° C. Once the optical density at 600 nm ($OD_{600}$) of the culture reached 0.6, temperature was lowered to 16° C. and isopropyl β-D-1-thiogalactopyranoside (IPTG, AMRESCO) was added to a final concentration of 0.1 mM to induce protein expression. Cells were harvested 15 h post induction by centrifugation at 700×g for 10 min and were lysed by sonication on a Misonex Ultrasonic Liquid Processer (Qsonica, LLC.) at amplitude 85 for 3 min with 10 sec on and 40 sec off cycles. Nucleic acids were removed from the crude extract by addition of 1 vol % polyethyleneimine (PEI, Acros) followed by centrifugation at 4° C. and 21,000×g for 10 min. The ELP tag enables purification of the fusion protein by ITC, a nonchromatographic method that we have previously developed for the purification of ELP fusion proteins that takes advantage of the inverse phase transition behavior imparted by the ELP (Meyer, D. E. & Chilkoti, A. *Nat. Biotechnol.* 2009, 14, 1112-1115). After triggering the inverse phase transition of the fusion by addition of 0.1 M ammonium sulfate, the aggregated proteins were collected by centrifugation at ~30° C. and 21,000×g for 10 min. The pellet was then resolubilized in cold PBS and the resulting solution was centrifuged at 4° C. and 21,000×g for 10 min to remove any remaining insoluble material. The last two steps were typically repeated one more time to obtain homogeneous protein, as verified by SDS-PAGE. In the final step, the protein was resolubilized in sortase buffer (50 mM Tris, 150 mM NaCl, 10 mM $CaCl_2$, pH adjusted to 7.5) in preparation for sortase-catalyzed initiator attachment.

The gene for sortase A with a 59 N-terminal amino acid truncation (previously shown to not affect its transpeptidase activity) and an N-terminal His6-tag in a pET15b vector was available from a previous study. Expression and purification of $His_6$-sortase A were carried out as previously described (Qi, Y., et al. *Macromol. Rapid Commun.* 2013, 34, 1256-1260).

Sortase-catalyzed initiator attachment and macroinitiator purification. The exendin-C—Br macroinitiator was synthesized and purified following procedures described previously with minor changes (Qi, Y., et al. *Macromol. Rapid Commun.* 2013, 34, 1256-1260). Briefly, a reaction mixture consisting of exendin-srt-$His_6$-ELP, $His_6$-sortase A, and AEBMP at a 2:1:60 ratio in sortase buffer was incubated at 20° C. for 18 h. After reaction, a reverse His-tag purification was used to isolate the exendin-C—Br macroinitiator, by exploiting the fact that it is the only species in the mixture without a $His_6$-tag. Purification was performed on an AKTA Purifier (GE Healthcare) equipped with a photodiode detector set at 280 nm and a HisTrap HP column. Elution through the column with PBS yielded pure exendin-C—Br in the eluent while leaving all other unwanted species bound to the resin. The collected exendin-C—Br was dialyzed overnight in PBS (pH 7.4) to remove residual free initiator.

Macroinitiator characterization. MALDI-MS was performed on a Voyager-DE Pro mass spectrometer (Life Technologies). Samples at ~25 µM in PBS were diluted 1:10 with 10 mg/mL sinapinic acid in 90:10 water/acetonitrile with 0.1 vol % trifluoroacetic acid (TFA) as the ionization matrix. The instrument was operated in linear mode with positive ions generated using a $N_2$ laser. Ubiquitin was used as a molecular weight standard to calibrate the instrument.

For LC/MS-MS analysis to confirm site-specificity of initiator attachment, 100 µL of ~8 uM exendin-C—Br in PBS was solvent exchanged into 50 mM ammonium bicarbonate (pH 8.0) on a ZebaSpin desalting column (Thermo Fisher Scientific) followed by trypsin (sequencing grade, Promega) digestion at 37° C. for 18 h directly in the column. The digestion mixture was collected by centrifugation, dried by vacuum centrifugation and was then resuspended in 20 µL 2% acetonitrile and 0.1% formic acid in water. 1 µL of the sample was separated on a NanoAquity ultra performance liquid chromatography (UPLC, Waters) system equipped with a BEH130 C18 reversed phase column (Waters) using a mobile phase consisting of (A) 0.1% formic acid in water and (B) 0.1% formic acid in acetonitrile. A linear gradient of 5% B to 40% B was performed over 60 min at 400 nL/min and the separated peptides were ionized by electrospray ionization (ESI) followed by MS analysis on a Synapt G2 HDMS QToF mass spectrometer (Waters). The top four most abundant ions were selected for MS/MS. Mass spectra were processed with Mascot Distiller (Matrix Science) and were then submitted to Mascot searches (Matrix Science) against a SwissProt_Ecoli database appended with the custom exendin-C—Br sequence. Search results were imported into Scaffold (v4.0, Proteome Software) and scoring thresholds were set to yield a minimum of 99% protein confidence for protein identification. Extracted ion chromatograms were performed in MassLynx (v4.1). Experimental isotope distributions of the brominated C-terminal tryptic peptide was compared to a theoretical isotope distribution modeled in Molecular Weight Calculator (v. 6.49, Pacific Northwest National Laboratory, ncrr.pnl.gov/software).

In situ ARGET-ATRP. All chemical reagents were purchased from Sigma Aldrich and used as received, unless otherwise specified. EG9 OEGMA monomer ($M_n$~500 Da or ~9 side-chain EG repeats on average, Sigma Aldrich, #447943) and EG3 OEGMA monomer (triethylene glycol methyl ether methacrylate, 232 Da, Sigma Aldrich, #729841) were passed through a column of basic alumina to remove the inhibitors.

In a typical reaction, 216 µmol of OEGMA and 21.6 µL of a stock solution of 200 mM $CuBr_2$ and 1.6 M tris(2-pyridylmethyl)amine (TPMA) pre-complexed in MilliQ water with 5% dimethylformamide (DMF) were mixed with 1 mL of 500 µM exendin-C—Br in PBS in a Schlenk flask. A 3.2 mM solution of ascorbic acid in MilliQ water was prepared in a separate flask. The two solutions were degassed by bubbling with argon for 30 min, after which Activator-Regenerated Regenerated Electron Transfer (ARGET) ATRP was initiated and maintained by continuously injecting the ascorbic acid solution into the reaction medium using a syringe pump at a rate of 1.6 nmol/min. Polymerization was allowed to proceed for a specified time at 20° C. under argon and was quenched by bubbling with air. Reactions of the EG3 OEGMA were done with 443 µmol of the monomer in 20 v/v % methanol in PBS while all other conditions remained the same. At the end of the reaction, the reaction mixture was dialyzed against PBS overnight to remove residual small molecule reagents in preparation for downstream characterization and purification.

Characterization of OEGMA monomers. Monomers diluted 1:20,000 in methanol were separated on an Agilent 1100 LC system equipped with a Zorbax Eclipse Plus C18 column (Agilent) using a mobile phase consisting of (A) 0.3% formic acid in water and (B) 0.3% formic acid in acetonitrile. A linear gradient of 50% B to 95% B was performed over 10 min at 50° C. Separated samples were ionized by ESI followed by MS analysis on an Agilent MSD ion trap mass spectrometer.

Physical characterization of exendin-C-POEGMA conjugates. Analytical SEC was performed on a Shimadzu high performance liquid chromatography (HPLC) system equipped with a UV-vis detector (SPD-10A VP) operating at 280 nm. 50 µL of samples at ~2 mg/mL were separated on a Protein KW-803 column (Shodex) using 0.1M Tris-HCl (pH 7.4) as mobile phase at 25° C. with a flow rate of 0.5 mL/min. Conjugation efficiency of in situ ATRP from exendin was calculated by quantifying AUC of peaks detected at 280 nm. Sum of the AUC's of the two peaks corresponding to the unreacted macroinitiator and the conjugate in each chromatogram was regarded as 100% and % fraction of the conjugate peak was calculated as the conjugation efficiency of that particular polymerization reaction.

The fluid line of the analytical HPLC system was connected downstream in series to a DAWN HELEOS II MALS detector followed by an Optilab T-rEX refractometer (both from Wyatt Technology) for conducting SEC-MALS analysis. The system was calibrated with toluene and normalized with 2.0 mg/mL bovine serum albumin (BSA, Pierce). Samples were passed through 0.1 µm filters before injection. do/dc values of the conjugates were determined on an Anton Paar Abbemat 500 refractometer (Anton Paar). Data were analyzed in ASTRA (v. 6.0, Wyatt Technology) to compute $M_w$, $M_n$ and Đ of the conjugates.

Conjugates were purified by a single round of preparative SEC on an AKTA Purifier equipped with a photodiode detector set at 280 nm and a HiLoad 26/600 Superdex 200 PG column using PBS as mobile phase at 4° C. and a flow rate of 2.0 mL/min.

DLS was performed on a DynaPro Plate Reader (Wyatt Technology). Samples were prepared at 25 µM and filtered with 0.1 µm filters before analysis. The instrument was operating at a laser wavelength of 831.95 nm, a scattering angle of 90° and at 25° C. Data were analyzed in Dynals mode using Dynamics 6.12.0.3.

General biochemical analysis. Concentrations of fusion proteins were measured on a ND-1000 Nanodrop spectrophotometer (Thermo Scientific) by UV-vis absorption spectroscopy. Concentration of exendin and conjugates for in vitro assays and in vivo studies was assessed using a Bicinchoninic Acid (BCA, Pierce) assay following manufacturer's instructions. SDS-PAGE analysis of sortase A was performed using precast 4-20% Tris-HCl gels (Bio-Rad). SDS-PAGE analyses of all exendin derivatives were performed using precast Tris/Tricine gels (Bio-Rad). Quantification of sortase reaction conversion was done by gel densitometry analysis using a built-in function in Image Lab (v. 4.0.1, Bio-Rad).

In vitro cAMP ELISA. Activity of native exendin and conjugates was assessed in vitro by quantifying intracellular cAMP release as a result of GLP-1R activation in BHK cells stably transfected with rat GLP-1R (a generous gift of Drucker group, University of Toronto, Toronto, Canada) (Drucker, D. J. & Nauck, M. A. Lancet 2006, 368, 1696-1705). Cells were allowed to reach 70-80% confluence in 24-well plates. Prior to the assay, ~20 µg of peptide or equivalent of conjugates were treated with 0.5 µg DPP4 (ProSpect) overnight to remove the di-alanine leader. On the day of the assay, cells were incubated with 3-isobutyl-1-methylxanthineto (IBMX, EMD Millipore) for 1 h to prevent cAMP degradation, followed by incubation with varying concentrations (0.001-1000 nM in log-scale increments) of exendin (Genscript) or conjugates for 10 min to trigger GLP-1R activation. 0.1 M HCl was then added to disrupt the cells and release intracellular cAMP. cAMP concentration was measured by a competitive cAMP ELISA according to the manufacturer's protocol (Enzo Life Sciences). Each sample was assayed in triplicate and data were analyzed in Igor Pro (v. 6.2, Wavemetrics) using a Hill equation fit to determine the EC50 of each construct (Goutelle, S. et al. Fundam. Clin. Pharmacol. 2008, 22, 633-648).

Animal studies. In vivo experiments were performed with 6-week-old male C57BL/6J mice (stock no. 000664) purchased from Jackson Laboratories. Upon arrival, mice were initiated on a 60 kCal % fat diet (#D12492, Research Diets Inc.) to induce a diabetic phenotype. Previous studies have established high fat-fed C57BL/6J mice as an adequate model for type 2 diabetes, as after one week on a high-fat diet, mice exhibit elevated blood glucose, progressively increasing insulin level, and severely compromised insulin response and glucose tolerance (Winzell, M. S. & Ahren, B. *Diabetes* 2004, 53, S215-S219; Surwit, R. S., et al. *Diabetes* 1988, 37, 1163-1167). Mice were housed under controlled light on a 12 h light/12 h dark cycle with free access to food and water. All mice were allowed to acclimate to the high-fat diet and the facility for 10 d before initiation of experiments. Mice used for fed glucose measurement study of EG3 conjugates were maintained on the high-fat diet for 3 weeks and used at the age of 8 weeks. All animal care and experimental procedures were approved by the Duke Institutional Animal Care and Use Committee.

In vivo fed glucose measurements. The effect of native exendin and the conjugates on fed blood glucose levels was measured following a single s.c. injection of each sample. Before blood glucose measurement, the tail was wiped with a sterilizing alcohol solution and wiped dry. A tiny incision was made on the mouse tail vein using a disposable lancet, and the first 1 µL drop of blood was wiped off. The second 1-2 µL blood drop was used for glucose measurement using a hand-held glucometer (AlphaTrack, Abbott). Blood glucose levels were measured 1 d before the experiment. On the day of injection, weights and blood glucose were measured, and a sample solution or PBS control of equivalent volume was injected s.c. Immediately following injection, mice were placed back in the cage with free access to food and water, and blood glucose was measured at 1, 4, 6 (exendin only), 8, 24, 48, 72, 96, 120 and 144 h post-injection. Weights were monitored daily. In the EG9 dose-dependent study, a 66.2 kDa EG9 exendin-C-POEGMA conjugate was injected into mice (n=3) at 25, 50, and 85 nmol/kg mouse body weight. In the EG9 MW-dependent study, EG9 conjugates of 25.4, 54.6, 97.2 and 155.0 kDa $M_n$s were injected into mice (n=6) at 25 nmol/kg. In the EG3 fed glucose study, 55.6kDa and 71.6 kDa EG3 exendin-C-POEGMA conjugates were injected into mice (n=5) at 25 nmol/kg. Blood glucose levels were normalized by the average glucose levels measured 24 h and immediately before injection to reflect the percent change in blood glucose and to correct for transient variations in glucose.

Figure 4A:
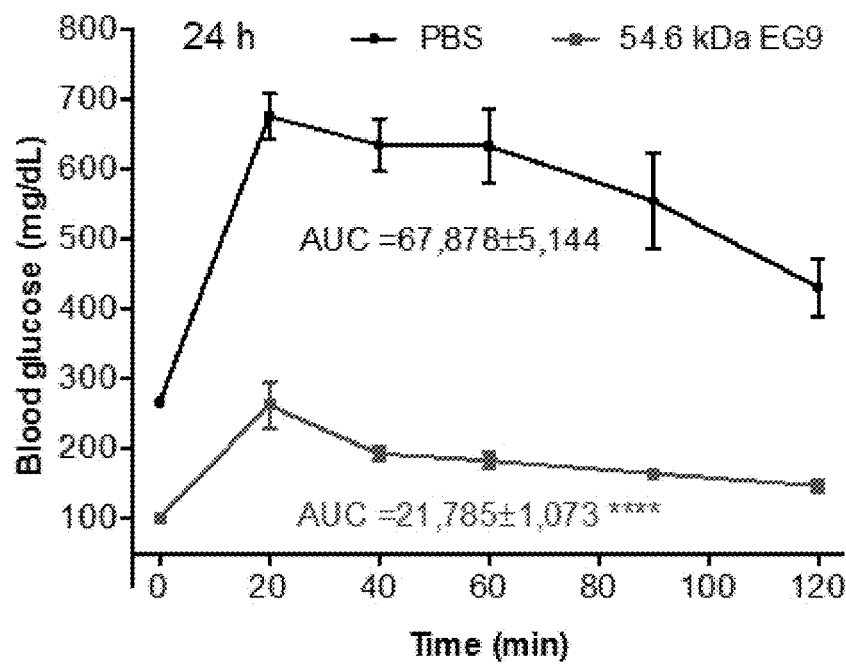
FIGS. 4A-4D are an intraperitoneal glucose tolerance test (IPGTT) of an EG9 exendin-POEGMA in mice. Mouse blood glucose levels measured in an IPGTT performed at 24 h and 72 h after a single s.c. injection of FIGS. 4A and 4B, the 54.6 kDa EG9 exendin-POEGMA conjugate or FIGS. 4C and 4D, unmodified exendin at 25 nmol/kg, compared to PBS of equivalent volume. Mice were fasted for 6 h prior to glucose challenge by an intraperotoneal (i.p.) injection of 1.5 g/kg of glucose. Results are plotted as mean±SEM, n=5 in panels FIGS. 4A and 4B, n=3 in panels c and d. AUCs of treatment and PBS were compared using an unpaired parametric two-tailed t test (P<0.01, and **P<0.0001). Exendin was not significant at either time point.
Figure 4B:
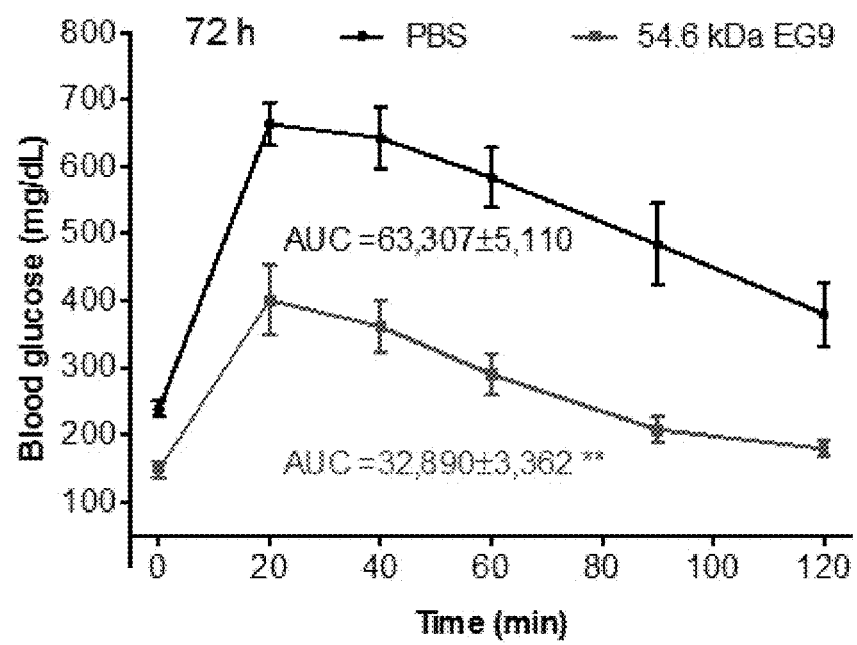

In vivo IPGTT. Mice were randomly divided into groups (n=5 in FIG. 4A and FIG. 4B, n=3 in FIG. 4C and FIG. 4D). On day one, every two groups of mice received a s.c. injection of either 54.6 kDa EG9 exendin-C-POEGMA conjugate, exendin as positive control, or PBS at equivalent volume as negative control. Exendin and the conjugate were injected at 25 nmol/kg. 18 h after injection, one group of mice in each category were fasted by removal of food for 6 h. At the end of the fast period (24 h following injection), mice were given 1.5 g/kg glucose (10 w/v % sterile glucose solution, Sigma) via i.p. injection. Blood glucose levels were monitored by nicking the tail vein and measuring the glucose level in the blood using a glucometer at 0, 20, 40, 60, 90, and 120 min after glucose administration. 66 h after injection, the remaining groups of mice were subjected to the same protocol and an IPGTT was similarly performed 72 h following injection.

In vivo pharmacokinetics. Exendin, 54.6 kDa EG9, 55.6 kDa EG3 and 71.6 kDa EG3 exendin-C-POEGMA conjugates were fluorescently labeled with Alexa Fluor® 488 NHS ester (Thermo Fisher Scientific) via their solvent accessible primary amines on lysine residues and the N-terminus, according to manufacturer's protocol. Unreacted free fluorophore was removed using a ZebaSpin desalting column (Thermo Fisher Scientific). Mice were randomly divided into four groups (n=3). Animals were weighed before injection. Each group of mice received a single s.c. injection of one of the labeled samples at 75 nmol/kg (45 nmol/kg fluorophore). 10 µL of blood samples were collected from the tail vein into 100 µL of a heparin solution (1 kU/ml in PBS, Sigma Aldrich) at 40 s, 40 min, 2.5 h, 4.5 h, 8 h, 24 h, 48 h, 72 h, 96 h and 120 h after injection. Blood samples were centrifuged at 4° C. and 20,000×g for 10 min to extract the plasma for fluorescence reading at excitation 485 nm and emission 535 nm on a Victor multilabel plate reader (Perkin Elmer). Plasma concentrations of constructs as a function of time were fitted using a non-compartmental analysis (PK Solutions 2.0, Summit Research Services) that characterizes the absorption and elimination phases of the profiles to derive the pharmacokinetic parameters.

In vitro anti-PEG ELISA. In the direct ELISA, columns of a 96-well microtiter plate (CoStar) were coated with Krystexxa® (Crealta Pharmaceuticals), ADA (Sigma-Tau Pharmaceuticals), Adagen® (Sigma-Tau Pharmaceuticals), exendin (Genscript), a 54.6 kDa EG9 exendin-C-POEGMA conjugate, a 55.6 kDa EG3 exendin-C-POEGMA conjugate or BSA (Sigma Aldrich). The antigen solutions for plate coating were prepared in PBS to yield ~2 µg of unmodified peptide/protein or ~5 µg of PEG/OEG in the case of polymer-modified antigens per well upon adding 50 µL to each well. The PEG/OEG contents of the polymer-modified antigens were calculated as follows: Krystexxa® consists of the tetrameric uricase enzyme (125 kDa total) with 10-11 lysine side-chain amino groups on each of its four subunits reacted with 10 kDa PEG p-nitrophenyl carbonate ester, giving a PEG content of ~76%. Adagen® consists of ADA (40.8 kDa) with 11-17 of its side-chain amino groups on solvent-accessible lysines functionalized with 5 kDa monomethoxy succinyl PEG according to the manufacturer's specifications (Sigma-Tau Pharmaceuticals). For our calculation, we assumed 14 PEG chains per Adagen® conjugate on average, giving ~60% PEG content. In the case of the exendin-C-POEGMA conjugates, subtracting the poly(methyl methacrylate) backbone (~17% for EG9 POEGMA and ~37% for EG3 POEGMA) gives an OEG content of ~75% for the 54.6 kDa EG9 conjugate and ~58% for the 55.6 kDa EG3 conjugate. After overnight incubation of the coated plate at 4° C., it was washed with PBS and all wells were blocked with 1% BSA in PBS. One patient plasma sample previously tested negative for PEG antibody and two that were tested positive were diluted 1:400 v/v in 1% BSA in PBS. The two positive patient plasma samples were from two different individuals that developed anti-PEG antibodies during a Phase II clinical trial of Krystexxa®. Following another round of PBS washing, 100 µL of each diluted plasma sample and 1% BSA in PBS were added to replicate wells of each antigen. The plate was then incubated at room temperature for 2 h. Wells were again washed with PBS and 100 µL of alkaline phosphatase-conjugated goat anti-human IgG (Sigma) diluted 1:5250 with 1% BSA in PBS was added to each well. After 1 h incubation at room temperature, wells were washed with PBS followed by Tris-buffered saline. Bound alkaline phosphatase was detected by incubating with p-nitrophenyl phosphate (Sigma) in accordance with the directions of the supplier. The phosphatase reaction was stopped by adding 50 µL/well of 10% NaOH, and the absorbance at 405 nm was measured on a plate reader (Tecan Infinite M200 Pro, Tecan Austria).

In the competitive ELISA, a microtiter plate was coated with 50 µL of 100 µg/mL Krystexxa® per well by overnight incubation at 4° C. Various amounts of ADA, Adagen®, exendin, a 54.6 kDa EG9 exendin-C-POEGMA conjugate, and a 55.6 kDa EG3 exendin-C-POEGMA conjugate were diluted with PBS to yield 0, 0.5, 2, 5, 10 and 20 μg of competing antigen per well upon adding 50 μL to each well. Dilutions of Adagen® and the exendin-C-POEGMA conjugates were prepared such that at each competing antigen concentration, similar PEG/OEG contents were compared as shown in TABLE 5. The diluted competing antigens were mixed with equal volume of a patient plasma sample that tested positive for PEG antibody (diluted 1:200 v/v in 1% BSA in PBS) and incubated at 4° C. overnight. The following morning, after washing with PBS, all wells were blocked with 1% BSA in PBS. Wells were washed with PBS after blocking, and 100 μL of each concentration of the competing antigen-plasma mixtures was added in replicate wells. After incubation at room temperature for 2 h, alkaline phosphatase-conjugated IgG was added for colorimetric readout at 405 nm as described above.

TABLE 5

Variable amounts of Adagen ® and exendin-C-POEGMA conjugates and their corresponding PEG/OEG contents loaded as competing antigens per well in the competitive ELISA. PEG content of Adagen ® was approximated by assuming 14 PEG chains per Adagen ® conjugate, while OEG content of the exendin-C-POEGMA conjugates was directly calculated by subtracting the poly(methyl methacrylate) backbone.

| Nominal (μg/well) | Adagen ® | | 54.6 kDa EG9 exendin-C-POEGMA | | 55.6 kDa EG3 exendin-C-POEGMA | |
|---|---|---|---|---|---|---|
| | Conjugate (μg/well) | PEG (μg/well) | Conjugate (μg/well) | OEG (μg/well) | Conjugate (μg/well) | OEG (μg/well) |
| 0.5 | 0.6 | 0.4 | 0.5 | 0.4 | 0.7 | 0.4 |
| 2 | 2.6 | 1.6 | 2.0 | 1.5 | 2.8 | 1.6 |
| 5 | 6.4 | 3.8 | 5.0 | 3.8 | 6.9 | 4 |
| 10 | 12.8 | 7.7 | 10.0 | 7.5 | 13.8 | 8 |
| 20 | 25.6 | 15.4 | 20.0 | 15.0 | 27.6 | 16 |

Figure 5A:
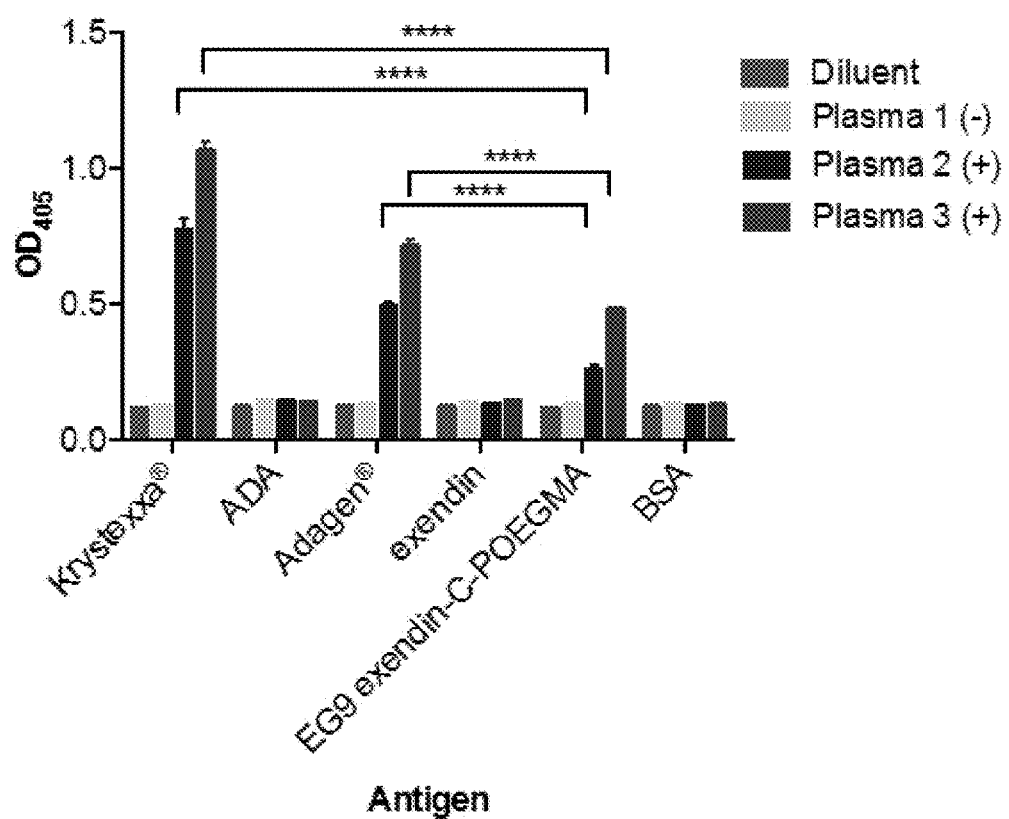
FIGS. 5A-5D are an assessment of reactivity of exendin-C-POEGMA conjugates toward anti-PEG antibodies in patient plasma samples.
Figure 5B:
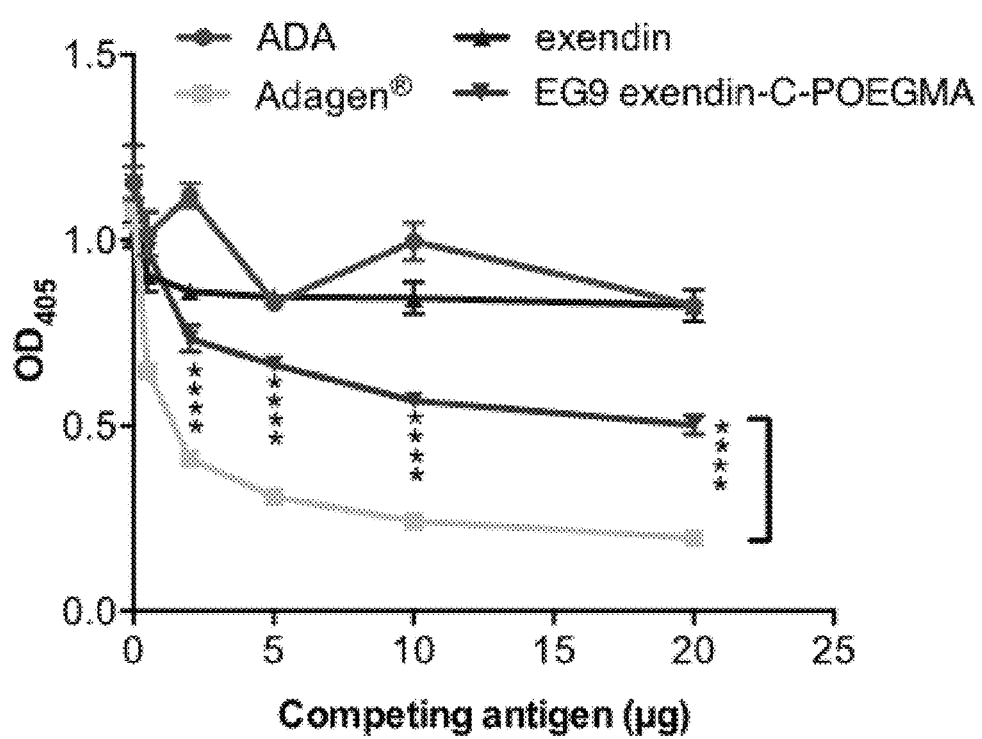
Figure 5C:
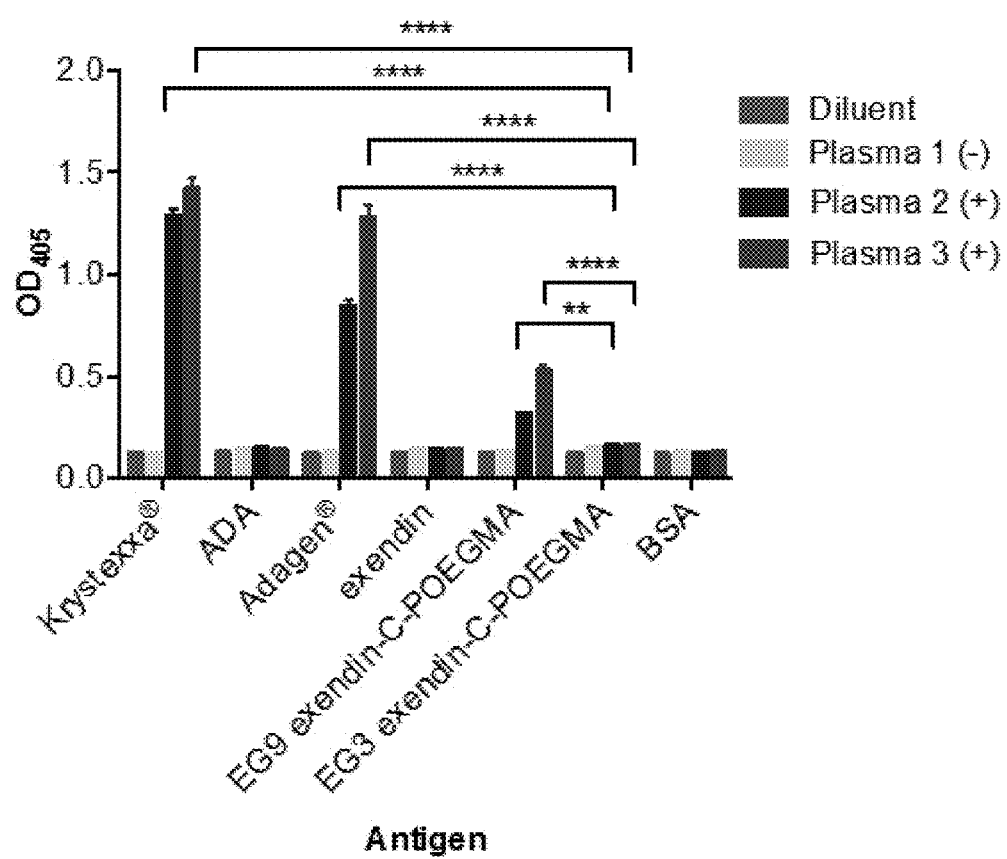
Figure 5D:
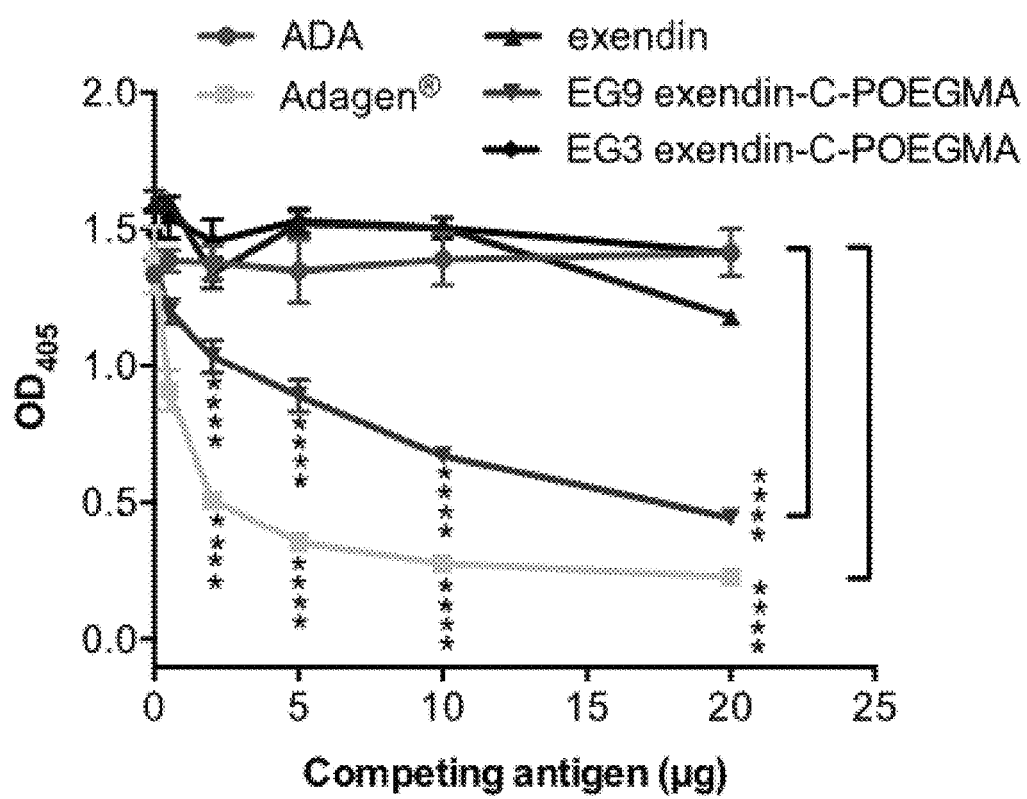

Assays in FIG. 5A and FIG. 5B were performed with n=3, while those in FIG. 5C and FIG. 5D were performed with n=5.

Statistical analysis. Data are presented as means±standard errors (SEs). Blood glucose levels in fed glucose measurement studies (n=6) were normalized by the average glucose levels measured 24 h and immediately before injection. Treatment effects on fed glucose levels were analyzed using repeated measures two-way ANOVA, followed by post hoc Dunnett's multiple comparison test to evaluate individual differences between a treatment and PBS control at each time point. AUCs of fed glucose profiles were compared using one-way ANOVA followed by post hoc Tukey's multiple comparison test (n=6). For evaluating AUC of IPGTT (n=5), treatment and PBS were compared using an unpaired parametric two-tailed t test. Both direct and competitive anti-PEG ELISAs (n=3) were analyzed using two-way ANOVA, followed by post hoc Dunnett's multiple comparison test to evaluate individual differences between exendin-C-POEGMA and the other groups for each plasma sample (direct) or antigen concentration (competitive). A test was considered significant if the P value was less than 0.05. Statistical analyses were performed using Prism 6 (GraphPad software Inc.).

EXAMPLE 2

Sortase-catalyzed C-Terminal Initiator Attachment to Exendin

Figure 7A:
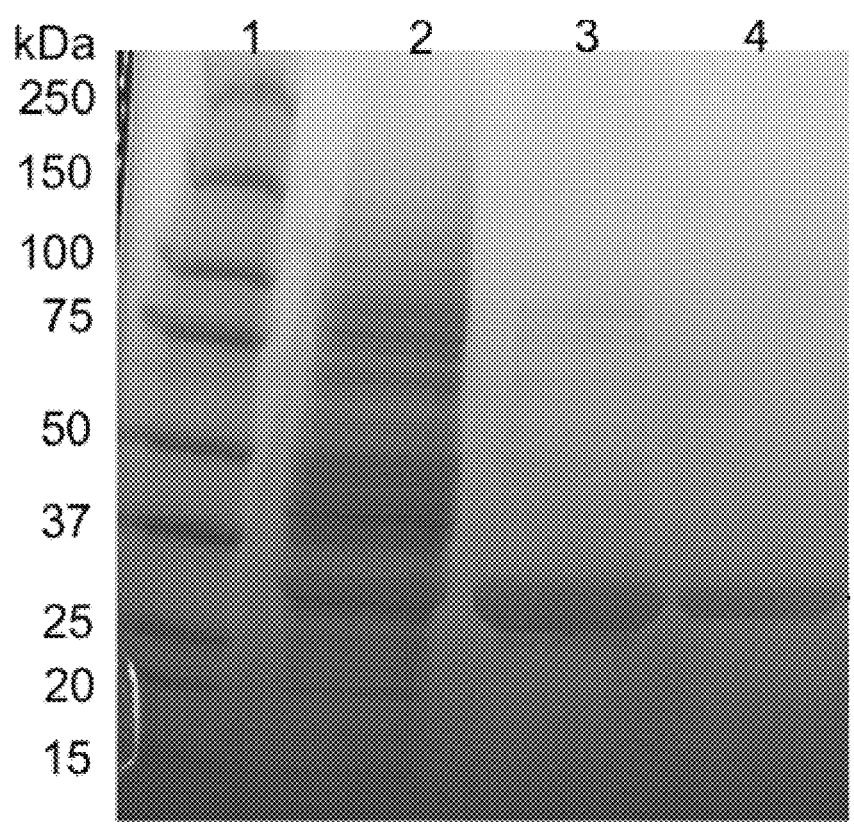
FIGS. 7A and 7B are a $CuCl_2$-stained SDS-PAGE analysis of FIG. 7A, exendin-srt-$His_6$-ELP purification by inverse transition cycling (ITC). Lane 1: marker, lane 2: E. coli lysate, lanes 3 and 4: soluble protein after one and two ITC cycles (yield: ~60 mg/L of culture). ELP: elastin-like polypeptide.
Figure 7B:
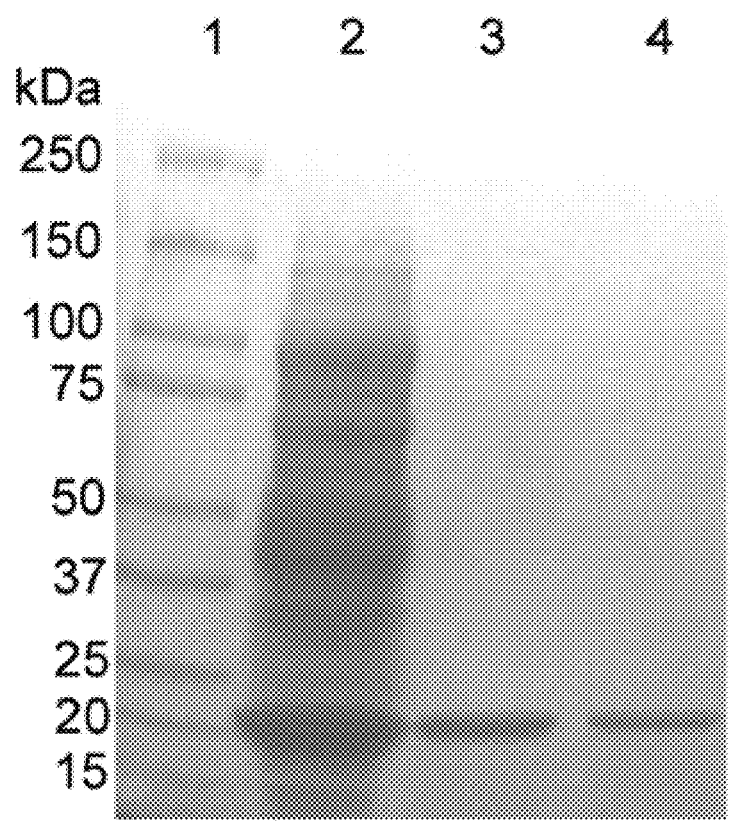

We exploited the C-terminal native peptide ligation mechanism of sortase A to site-specifically attach the ATRP initiator N-(2-(2-(2-(2-aminoacetamido)acet-amido)acet-amido) ethyl)-2-bromo-2-methylpropanamide (AEBMP) to the C-terminus of exendin (FIG. 1A-1C). A quaternary fusion protein, abbreviated as "exendin-srt-His$_6$-ELP", was recombinantly expressed to serve as the sortase A substrate (FIG. 1A). As explained in an earlier study, "srt" stands for the native sortase A recognition sequence "LPETG" and ELP refers to a stimulus-responsive elastin-like polypeptide that was incorporated to enable easy purification of the fusion protein by inverse transition cycling (ITC, FIG. 7A), a nonchromatographic protein purification method that we previously developed (Meyer, D. E. & Chilkoti, A. *Nat. Biotechnol.* 1999, 14, 1112-1115). The recognition sequence was deliberately located between the protein and the ELP, so that transpeptidation by sortase A not only attaches the initiator to exendin, but also conveniently liberates the purification tag. Sortase A with an N-terminal hexahistidine tag (His$_6$-tag) was recombinantly expressed from a plasmid constructed in the earlier study and was purified by immobilized metal affinity chromatography (IMAC, FIG. 7B). The ATRP initiator AEBMP (FIGS. 1A-1C) was chemically synthesized with an N-terminal (Gly)$_3$ motif serving as the nucleophile, as maximum reaction rates for sortase-catalyzed C-terminal ligation have been reported with two or more glycines (Mao, H., et al. *J. Am. Chem. Soc.* 2004, 126).

Figure 2A:
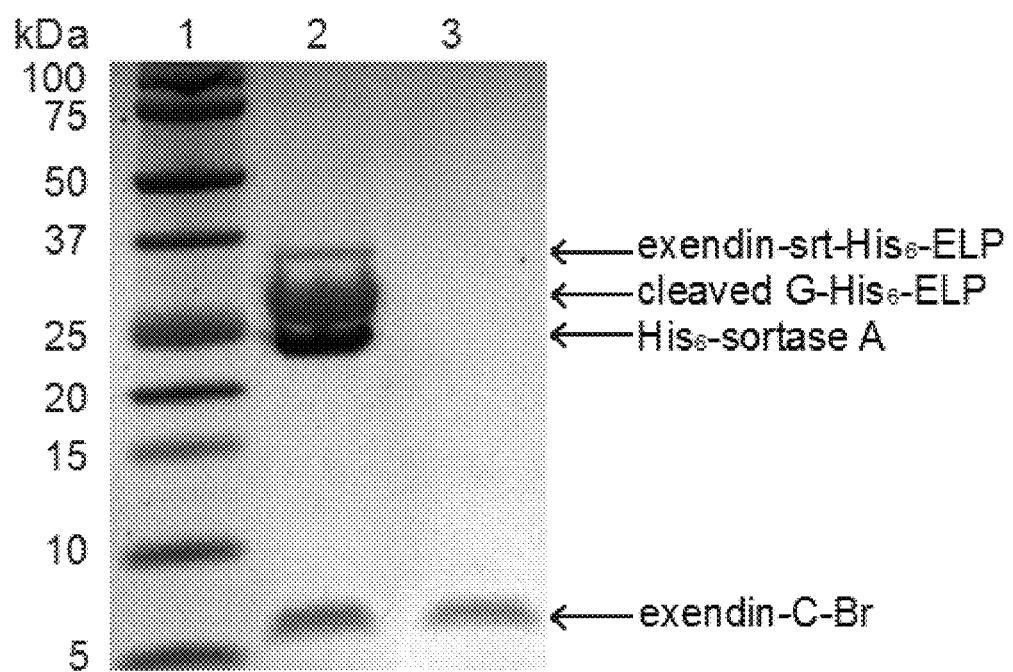
FIGS. 2A-2C are a characterization of exendin-C—Br macroinitiator and EG9 exendin-C-POEGMA conjugates.

Successful sortase-catalyzed initiator attachment (FIG. 1B) resulted in cleavage of exendin-LPETG-His$_6$-ELP into exendin-LPET and G-His$_6$-ELP, followed by attachment of AEBMP to exendin-LPET to generate the macroinitiator product (exendin-C—Br). Sodium dodecyl sulfate-polyacrylamide gel electrophoresis (SDS-PAGE) analysis of the reaction mixture (FIG. 2A) showed >90% conversion to exendin-C—Br, as assessed by gel densitometry. Similar to the previous study, a His$_6$-tag was intentionally inserted between "srt" and ELP on the exendin-srt-His$_6$-ELP fusion, such that upon transpeptidation by His$_6$-sortase A, all the residual reactants, enzyme and side-products except the desired product—exendin-C—Br—carried a His$_6$-tag. Consequently, elution through an IMAC column yielded pure exendin-C—Br (FIG. 2A) in the eluent while leaving all other unwanted species bound to the resin.

EXAMPLE 3

Synthesis and Characterization of Exendin-C-POEGMA Conjugates

Next, in situ Activator Regenerated by Electron Transfer (ARGET) ATRP (Jakubowski, W. & Matyjaszewski, K.

Figure 2B:
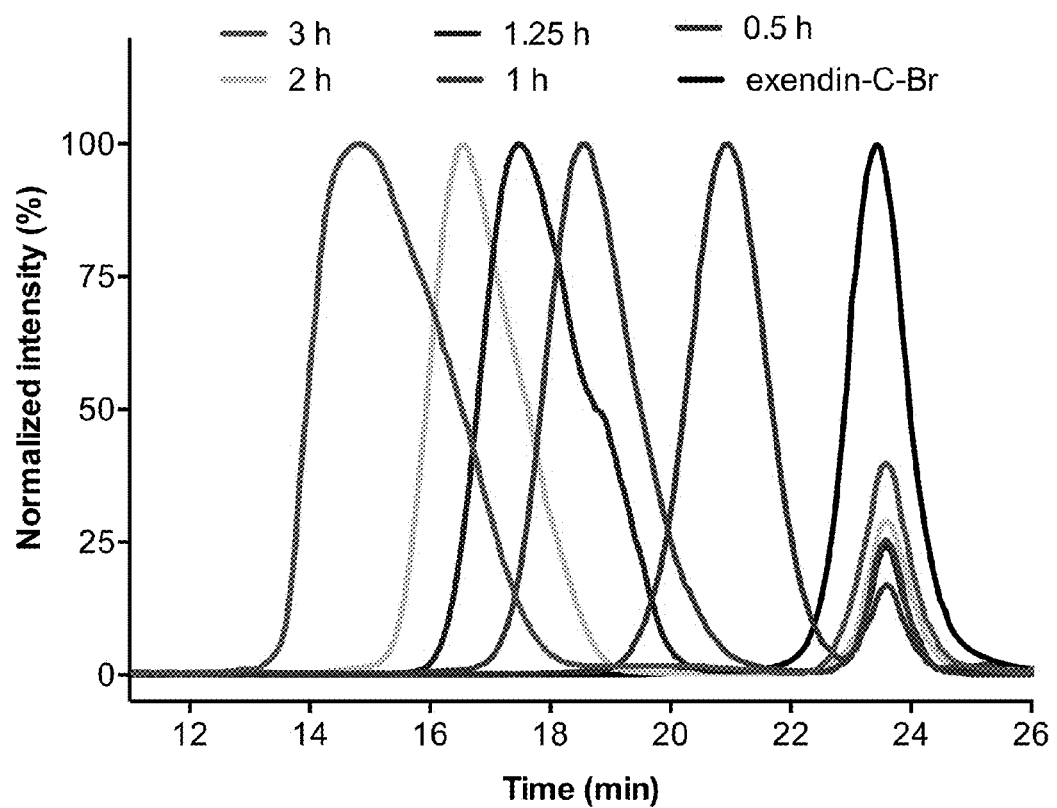
Figure 8A:
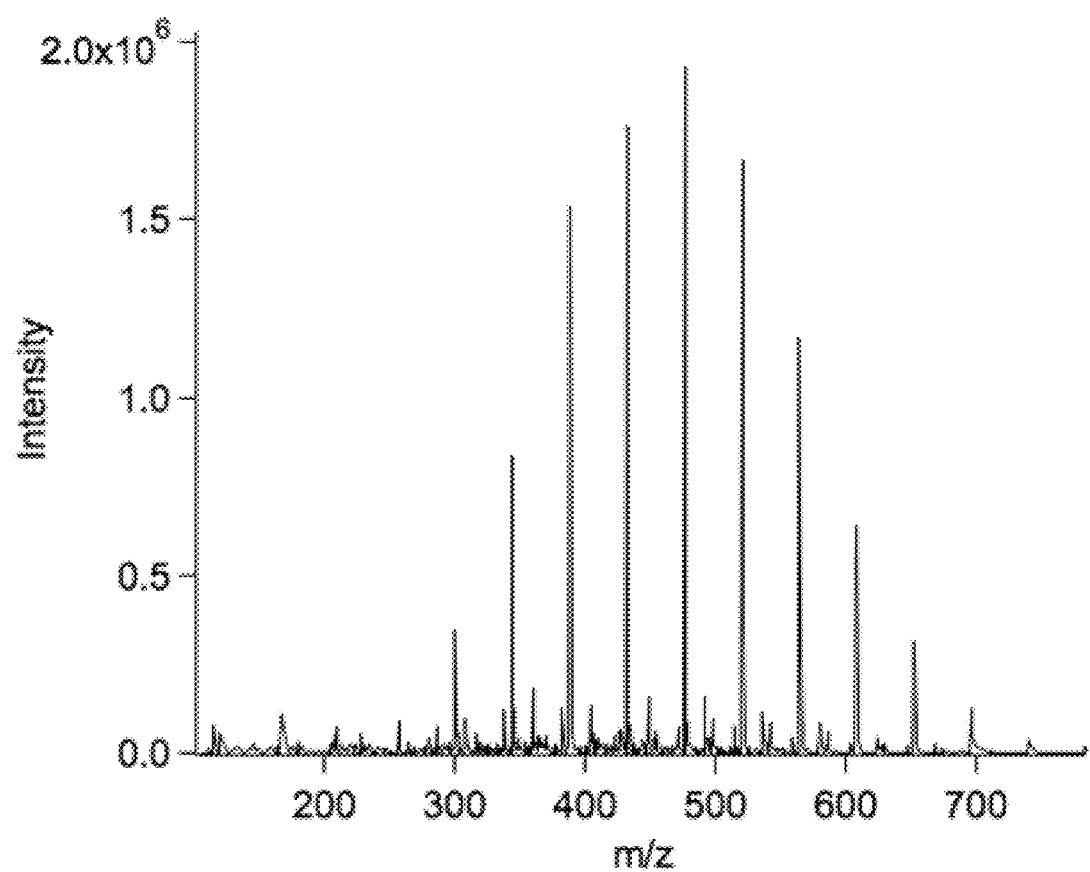
FIGS. 8A and 8B are a liquid chromatography electrospray ionization mass spectrometry (LC/ESI-MS) characterization of OEGMA monomer with FIG. 8A, an average mass of ~500 Da or ~9 side-chain ethylene glycol repeats (EG9), and FIG. 8B, a mass of 232 Da or 3 side-chain EG repeats (EG3). Peaks were detected as $[M+Na]^+$.
Figure 9A:
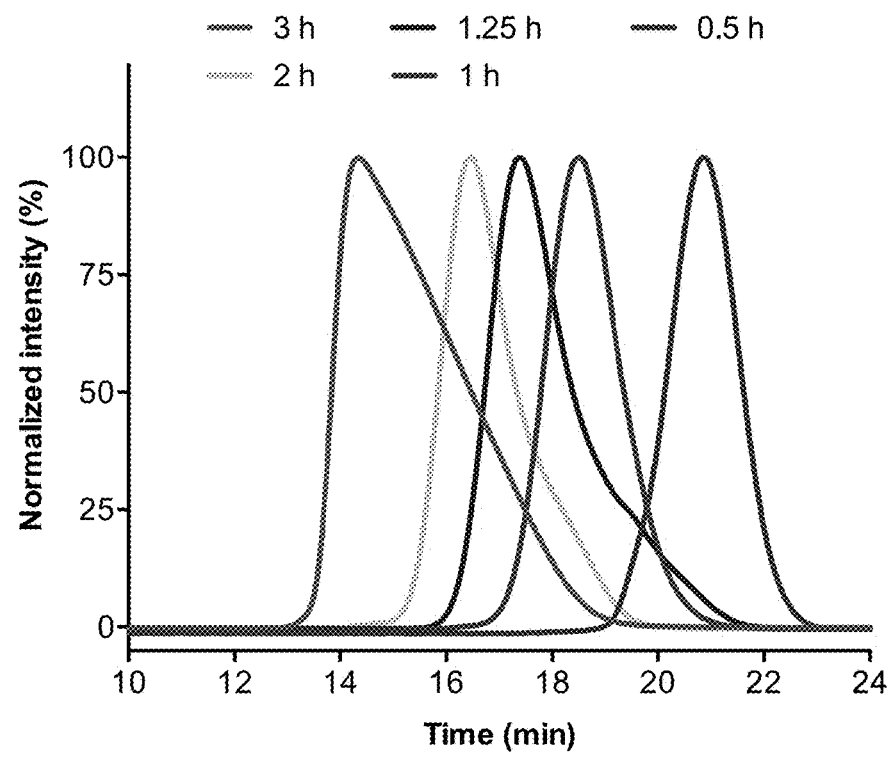
FIGS. 9A and 9B are a physical characterization of EG9 exendin-C-POEGMA conjugates.
Figure 9B:
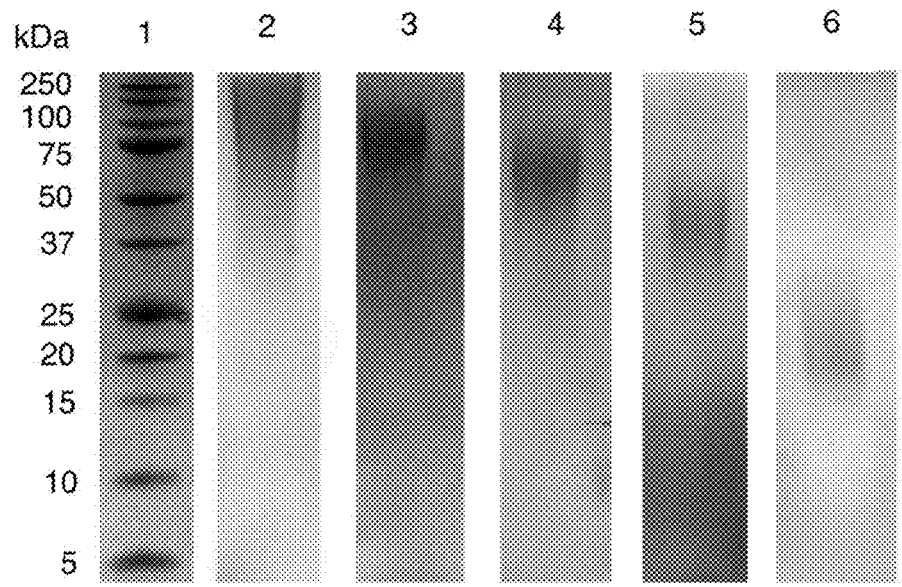
Figure 10A:
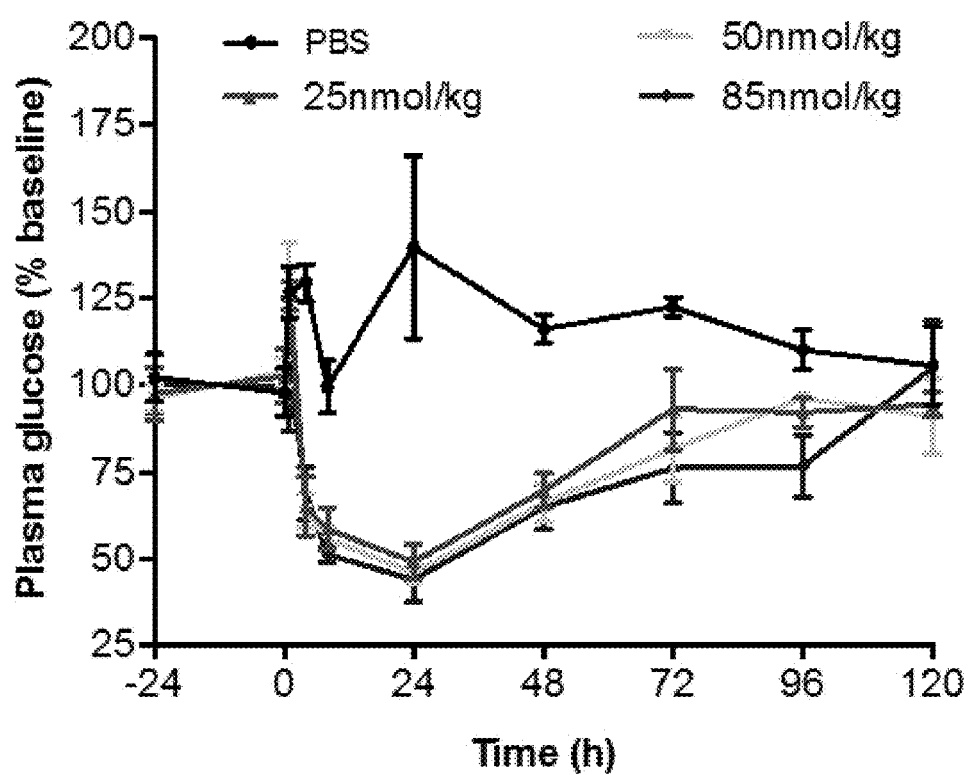
FIGS. 10A-10C are an assessment of in vivo dose-dependent efficacy of EG9 exendin-C-POEGMA. Overlaid FIG. 10A, normalized and FIG. 10B, un-normalized blood glucose levels of 6-wk-old male C57BL/6J mice (n=3) maintained on a 60 kCal % diet measured before and after a single s.c. injection of a 66.2 kDa EG9 exendin-C-POEGMA conjugate at 25, 50, 80 nmol/kg or phosphate buffered saline (PBS) control of equivalent volume administered at t=0 h. Blood glucose levels in panel a were normalized to the average glucose levels measured 24 h prior to and immediately before injection.
Figure 10B:
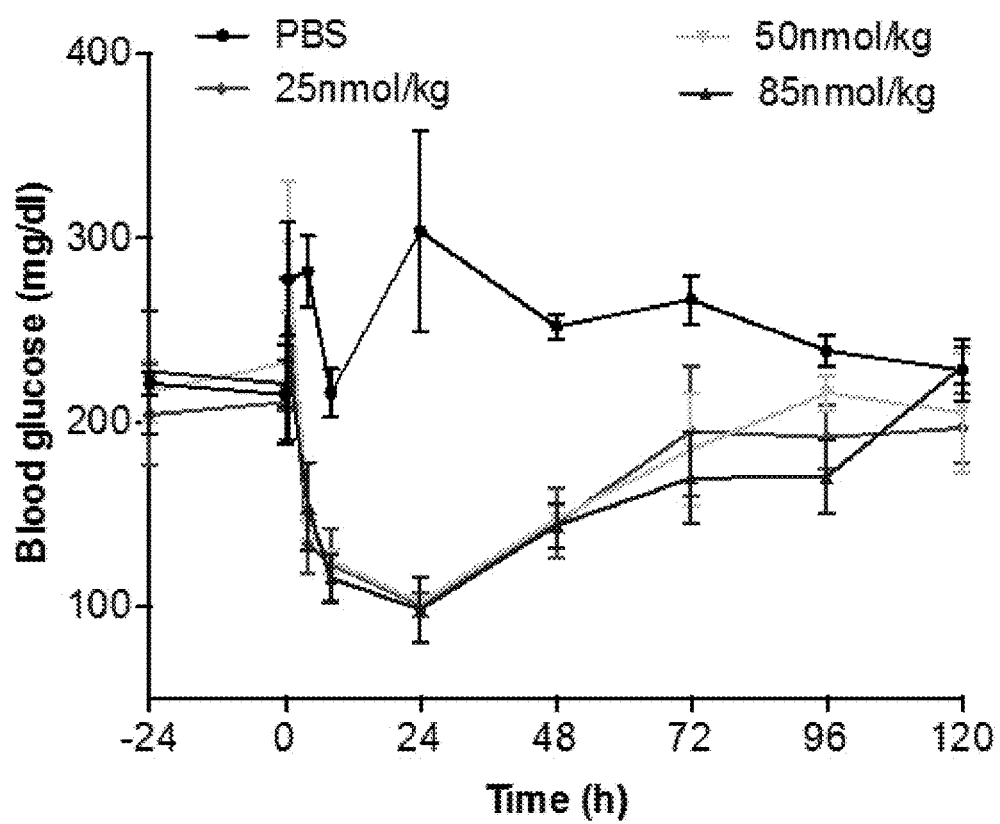
Figure 10C:
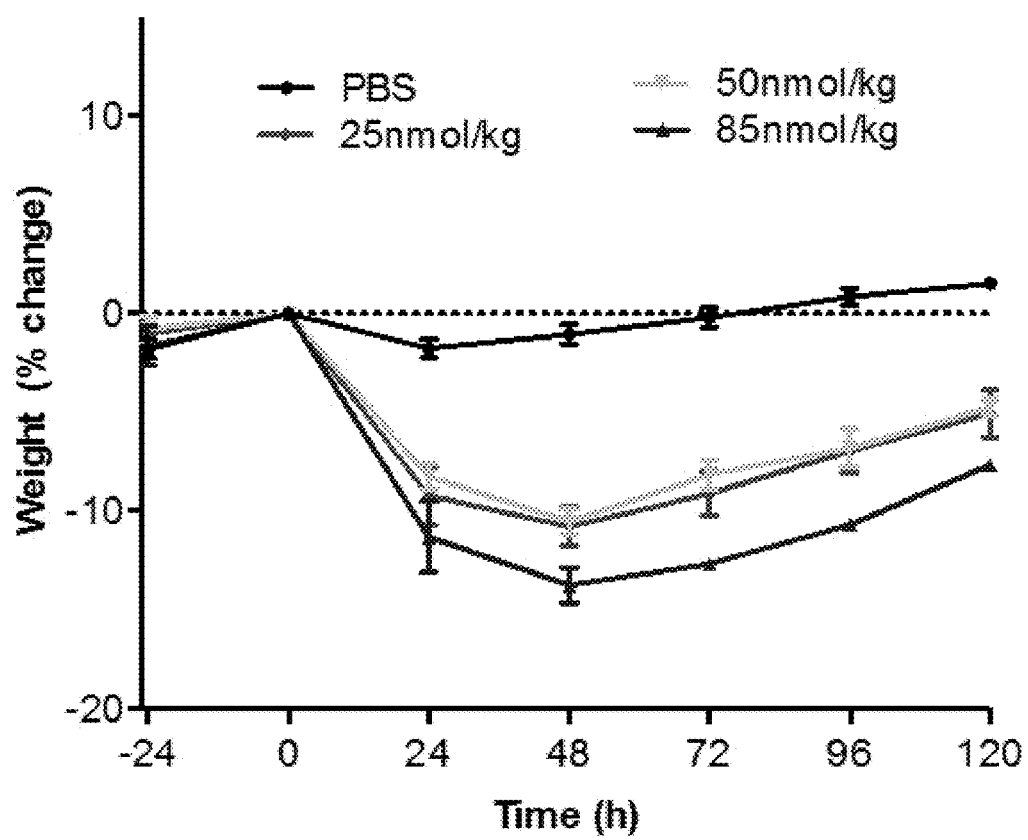
Figure 11A:
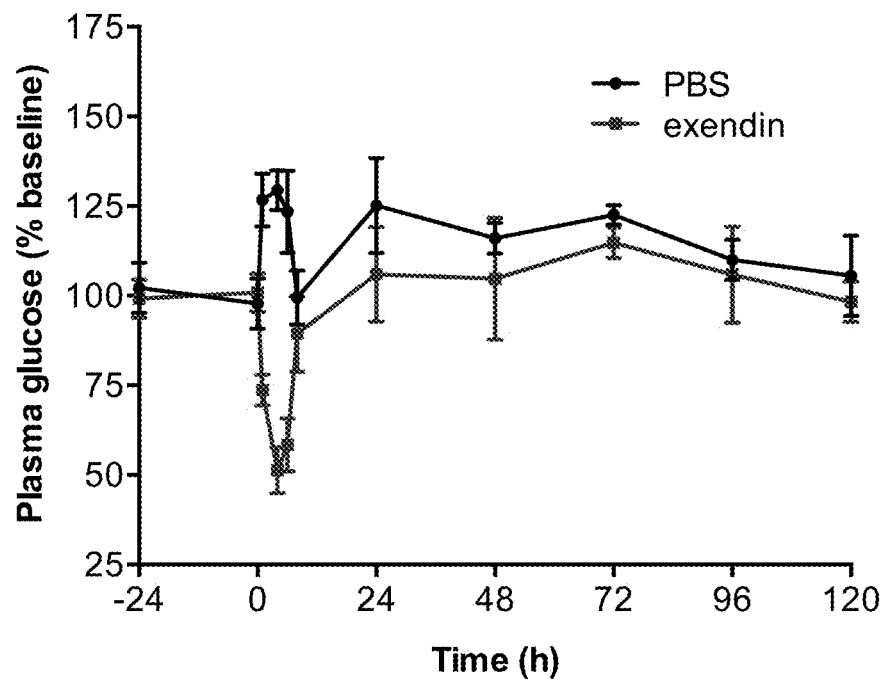
FIGS. 11A and 11B are an assessment of in vivo efficacy of unmodified exendin.
Figure 11B:
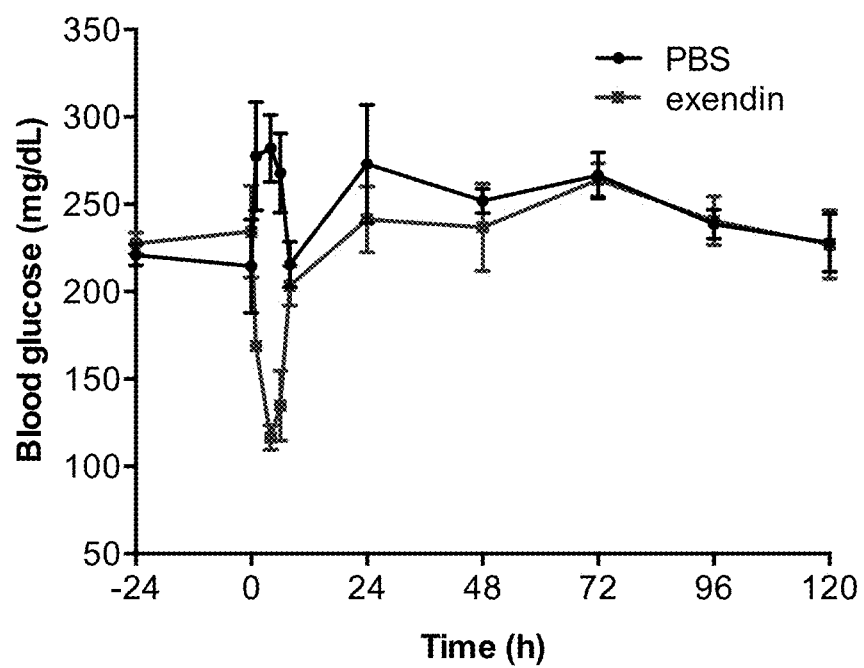
Figure 12A:
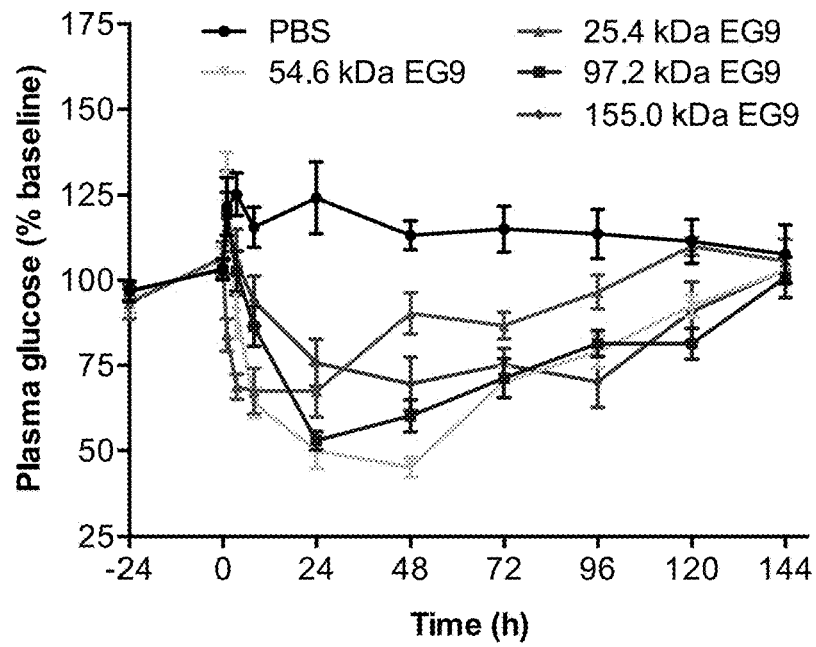
FIGS. 12A-12C are an assessment of in vivo MW-dependent efficacy of EG9 exendin-C-POEGMA conjugates. Overlaid FIG. 12A, normalized and FIG. 12B, un-normalized fed blood glucose levels in mice (n=6) measured before and after receiving a single s.c. injection of 25.4 kDa, 54.6 kDa, 97.2 kDa, 155.0 kDa EG9 exendin-POEGMA conjugates at 25 nmol/kg compared to PBS control at equivalent volume injected at t=0 h. Blood glucose levels in panel a were normalized to the average glucose levels measured 24 h prior to and immediately before injection.
Figure 12B:
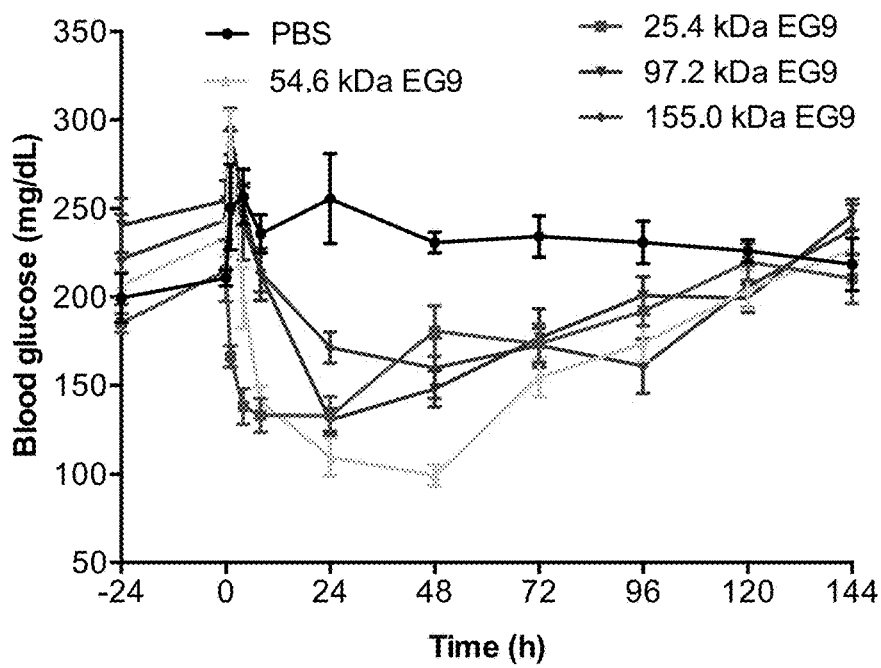
Figure 12C:
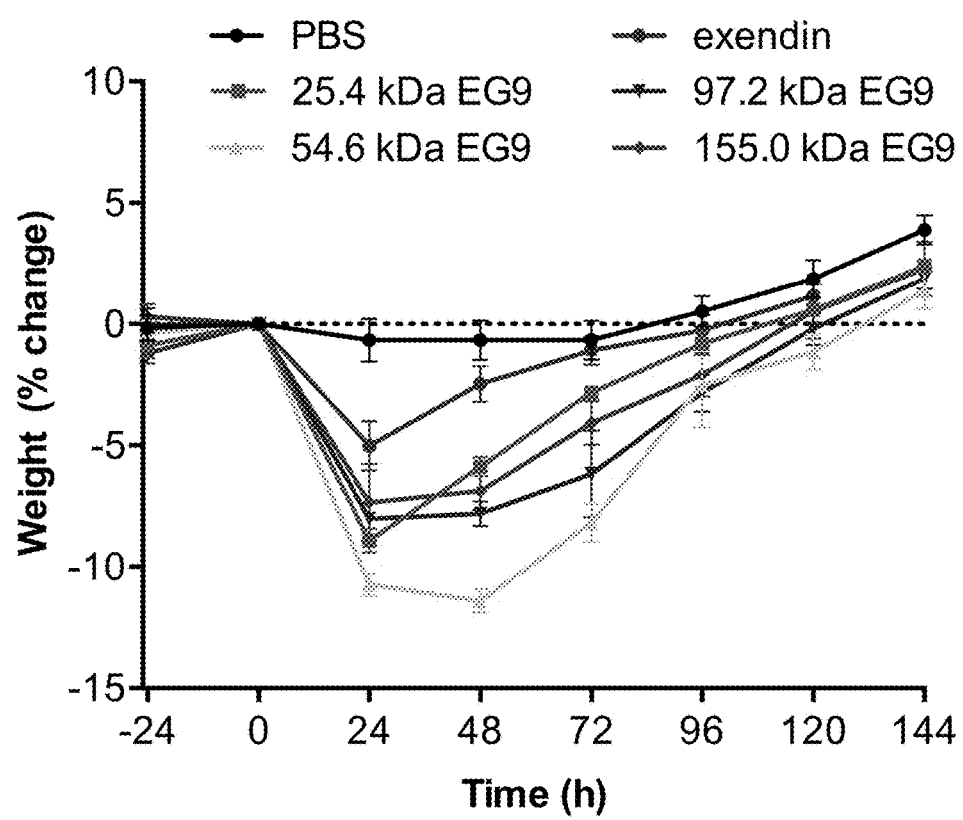

Angew. Chem. Int. Ed. 2006, 45, 4482-4486) was carried out to graft POEGMA from exendin-C—Br (FIG. 1C). An OEGMA monomer with an average mass of ~500 Da or ~9 side-chain EG repeats (EG9) was used, as shown by liquid chromatography electrospray ionization mass spectrometry (LC/ESI-MS) analysis (FIG. 8A). The reaction time was varied to produce EG9 exendin-C-POEGMA conjugates with a range of MWs. Size exclusion chromatography (SEC) analysis of exendin-C—Br before polymerization detected by UV-vis absorbance at 280 nm (FIG. 2B) showed a single peak eluting at 23.7 min. After polymerization, the intensity of the macroinitiator peak greatly diminished, and was accompanied by the appearance of peaks at 21.3, 19.5, 17.8, 16.5, and 15.0 min, corresponding to EG9 exendin-C-POEGMA conjugates with increasing MWs as the reaction time was increased. The results from UV-vis detection were in agreement with those from refractive index (RI) detection (FIG. 9A). Integration of peak areas in the UV-vis chromatograms showed that the average conjugation yield was ~80%. As shown in TABLE 1, the synthesized conjugates had $M_n$s that ranged from 25.4 to 155.0 kDa and all conjugates had very narrow dispersities ($Đ ≤ 1.15$). The conjugates could be easily and completely purified by a single round of preparative SEC (FIG. 9B).

TABLE 1

Figure 13:
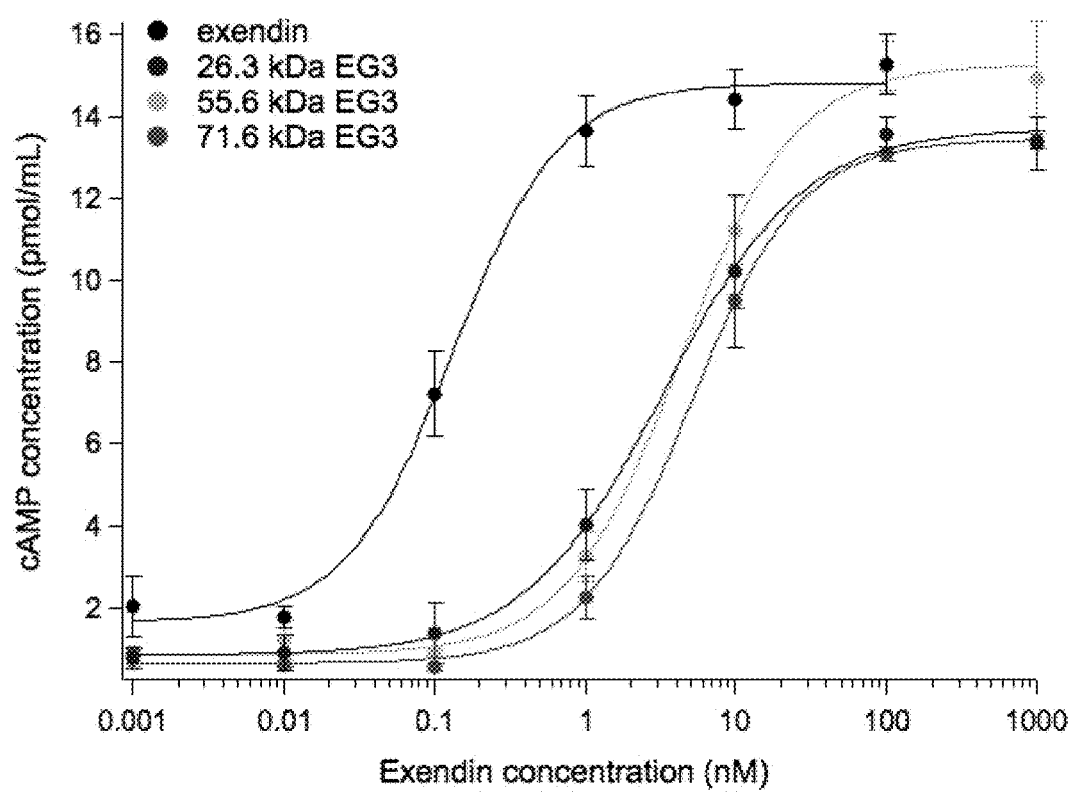
FIG. 13. Cyclic adenosine monophosphate (cAMP) response of native exendin and EG3 exendin-C-POEGMA conjugates with $M_n$s of 26.3 kDa, 55.6 kDa and 71.6 kDa in baby hamster kidney (BHK) cells expressing the glucagon-like peptide-1 receptor (GLP-1R). Results are plotted as mean±SEM. Half-maximal effective concentration ($EC_{50}$) values are summarized in TABLE 1.
Figure 14A:
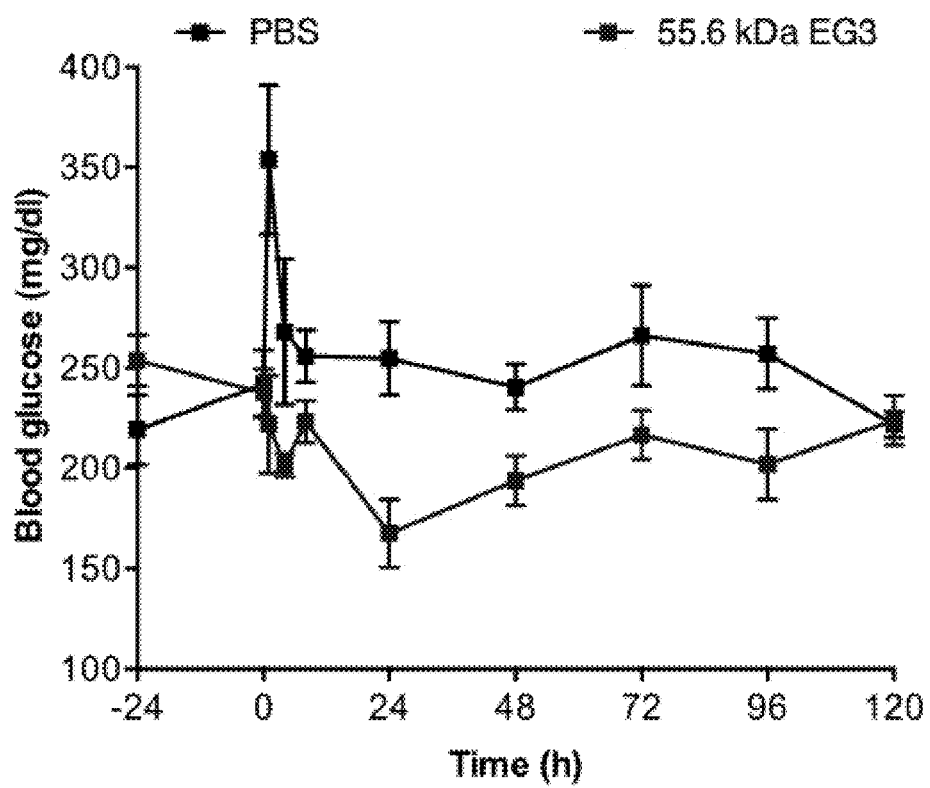
FIGS. 14A-14D are an assessment of in vivo efficacy of an EG3 exendin-C-POEGMA conjugate. Un-normalized blood glucose levels in fed mice (n=3) measured before and after receiving a single s.c. injection of FIG. 14A, 55.6 kDa and FIG. 14B, 71.6 kDa EG3 exendin-POEGMA conjugate at 25 nmol/kg compared to PBS control at equivalent volume administered at t=0 h. Weight profiles for FIG. 14C, 55.6 kDa and FIG. 14D, 71.6 kDa EG3 exendin-C-POEGMA and PBS control groups. Weights are reported as % change from 0 h time point. Results in all panels are plotted as mean±SEM.
Figure 14B:
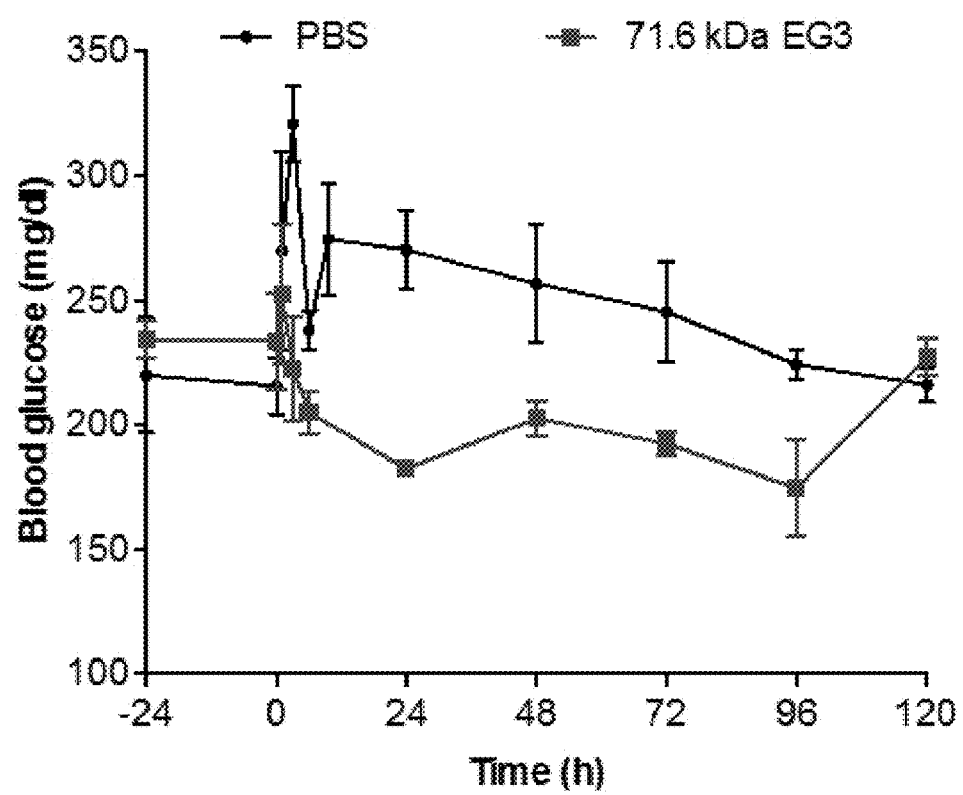
Figure 14C:
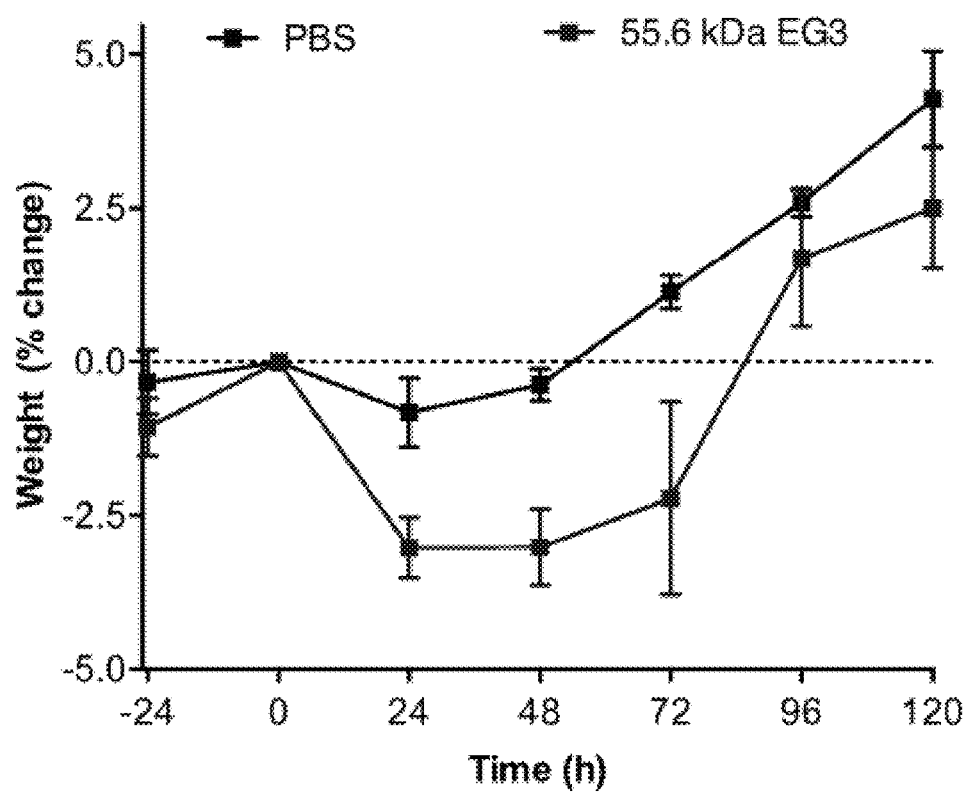
Figure 14D:
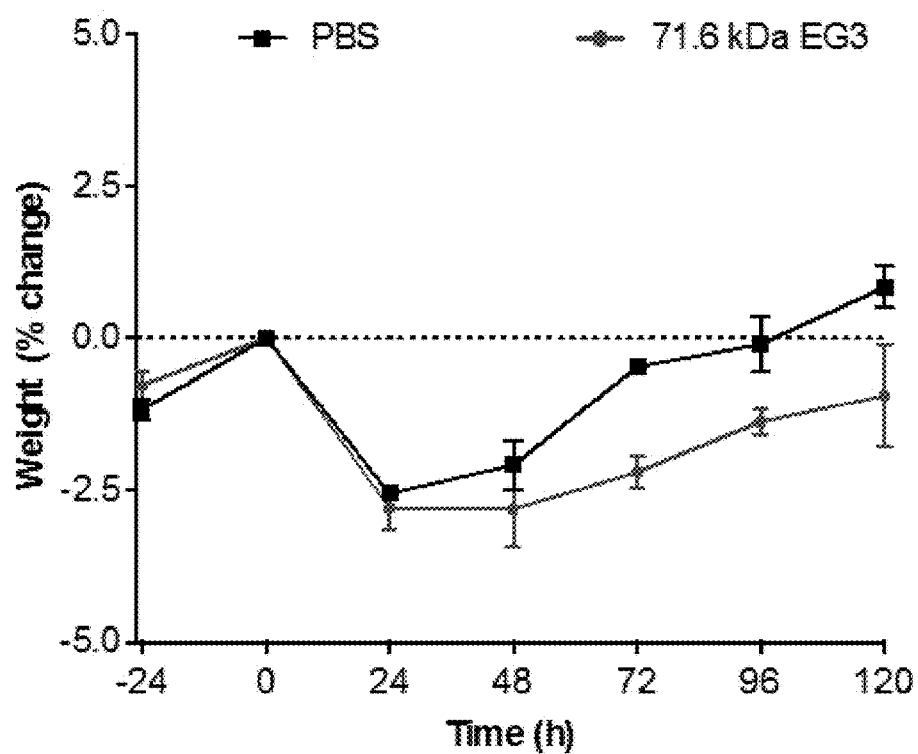

Physical properties and biological activity of exendin and exendin-C-POEGMA conjugates. MWs and Đs were determined by size exclusion chromatography multi-angle light scattering (SEC-MALS). $R_h$s were measured by dynamic light scattering (DLS). $EC_{50}$ values of EG9 and EG3 conjugates were derived from cAMP response curves in FIG. 2C and FIG. 13, respectively. $R_h$ and $EC_{50}$ values are reported as mean ± SEM, n = 10 for $R_h$ and n = 3 for $EC_{50}$. $M_w$: weight-average MW, $M_n$: number-average MW, Đ: dispersity, $R_h$: hydrodynamic radius, $EC_{50}$: half-maximal effective concentration. [a]Calculated from amino acid sequence. [b]Default value due to unimolecular nature of the peptide.

| Species | Reaction time (h) | $M_w$ (Da) | $M_n$ (Da) | Đ ($M_w/M_n$) | $R_h$ (nm) | $EC_{50}$ (nM) |
|---|---|---|---|---|---|---|
| exendin | — | — | 4,186.6[a] | 1.00[b] | 2.2 ± 0.1 | 0.08 ± 0.01 |
| EG9 | 0.5 | 26,400 | 25,400 | 1.04 | 4.5 ± 0.4 | 0.84 ± 0.09 |
| EG9 | 1 | 56,800 | 54,600 | 1.04 | 5.6 ± 0.5 | 1.91 ± 0.35 |
| EG9 | 1.25 | 72,200 | 66,200 | 1.09 | 5.9 ± 0.5 | 2.10 ± 0.08 |
| EG9 | 2 | 100,000 | 97,200 | 1.03 | 6.8 ± 0.7 | 6.67 ± 0.21 |
| EG9 | 3 | 178,000 | 155,000 | 1.15 | 7.6 ± 0.5 | 7.69 ± 0.04 |
| EG3 | 3 | 27,400 | 26,300 | 1.04 | 3.8 ± 0.4 | 3.29 ± 0.27 |
| EG3 | 5.5 | 60,600 | 55,600 | 1.09 | 4.8 ± 0.5 | 4.17 ± 0.13 |
| EG3 | 8 | 82,700 | 71,600 | 1.16 | 5.4 ± 0.6 | 5.11 ± 0.23 |

Figure 2C:
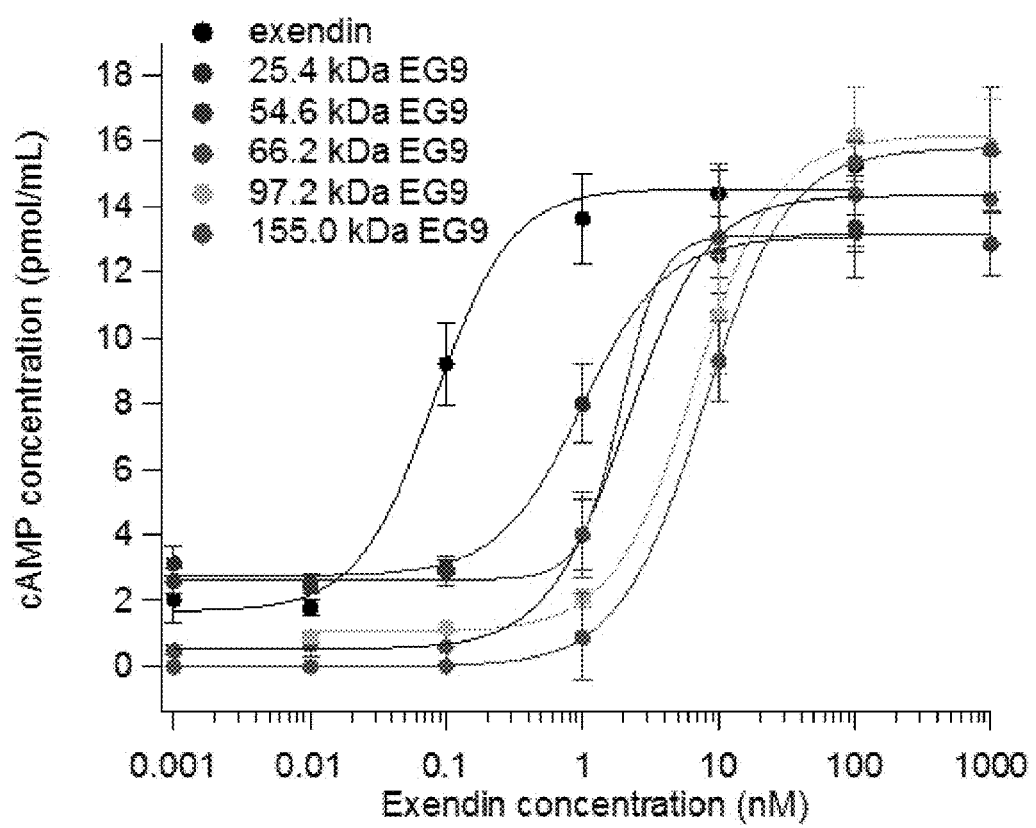

Exendin acts by binding and activating the G protein-coupled GLP-1 receptor (GLP-1R), which results in the release of cyclic adenosine monophosphate (cAMP) as a second messenger in a downstream signaling cascade, ultimately leading to secretion of insulin to regulate blood glucose. The potency of native exendin and the EG9 exendin-C-POEGMA conjugates were next assessed by quantifying intracellular cAMP release as a result of GLP-1R activation in baby hamster kidney (BHK) cells that were stably transfected with rat GLP-1R. As shown in FIG. 2C and TABLE 1, grafting EG9 POEGMA from exendin increases the $EC_{50}$ of the peptide in an overall MW-dependent manner, which indicates decreased receptor binding with increasing polymer MW as a result of the steric hindrance imposed by the appended POEGMA chain.

EXAMPLE 4

In Vivo Therapeutic Efficacy of EG9 Exendin-C-POEGMA

The in vivo efficacy of EG9 exendin-C-POEGMA conjugates was assessed in male C57BL/6J mice that were maintained on a 60 kCal % fat diet, so as to develop a diabetic phenotype (Wnzell, M. S. & Ahren, B. *Diabetes* 2004, 53, S215-S219; Surwit, R. S., et al. *Diabetes* 1988, 37, 1163-1167). A dose-dependent study was first performed to determine an adequate dose. A 66.2 kDa EG9 exendin-C-POEGMA conjugate was administered into mice via a single s.c. injection at 25, 50 and 85 nmol/kg mouse body weight of the conjugate. Fed blood glucose levels measured at various time points post-injection revealed an overall slight increase in the duration of glucose reduction with increasing dose of the conjugate compared to phosphate buffered saline (PBS) control (FIG. 10A and FIG. 10B, TABLE 3). A similar trend was observed in the mouse body weights, where the mice treated with the highest dose showed considerably more weight loss than the two lower doses (FIG. 10C). While the weight-lowering benefit of exendin has been well established, overdosing can cause nausea, which can lead to acute weight loss in rodents. The excessive weight loss seen in mice that received the highest dose suggests the possibility of nausea, and all subsequent studies were hence carried out with a dose of 25 nmol/kg.

TABLE 3

Summary of statistical significance levels of dose-dependent fed blood glucose measurements of EG9 exendin-C-POEGMA shown in FIG. 10A compared to PBS control.

| | Dosage (nmol/kg) | | |
|---|---|---|---|
| Time (h) | 25 | 50 | 85 |
| 1 | | | |
| 4 | **** | **** | **** |
| 8 | ** | ** | *** |
| 24 | **** | **** | **** |
| 48 | *** | *** | *** |
| 72 | | ** | **** |
| 96 | | | * |

Data were analyzed by repeated measures two-way analysis of variance (ANOVA), followed by post hoc Dunnett's test to evaluate individual differences between a treatment and PBS control at each time point (n = 3, * P < 0.05,  P < 0.01, * P < 0.001 and **** P < 0.0001).

To investigate the effect of MW on the glucose regulatory effect of EG9 exendin-C-POEGMA conjugates, native exendin and conjugates of four different MWs ($M_n$=25.4, 54.6, 97.2 and 155.0 kDa) were tested at a single s.c. injection at 25 nmol/kg mouse body weight. While unmodified exendin was only able to lower blood glucose for 6 h relative to PBS control (FIG. 3B, full glucose profiles in FIGS. 11A and 11B), modification with EG9 POEGMA significantly extended the glucose-lowering effect of exendin for up to 120 h, with a MW-dependence on the onset, magnitude and duration of the effect (FIGS. 3B-3E, TABLE 4). As is evident from the overlaid glucose profiles in FIG. 12A (overlaid un-normalized glucose profiles in FIG. 12B), an increase in MW delays the onset but prolongs the duration of glucose reduction, and the two higher MW conjugates showed an overall smaller magnitude of glucose reduction. This trend is mirrored by the weight profiles of treated animals as well (FIG. 12C). The two higher MW conjugates also showed much more flat and steady glucose profiles. The glucose profile of the 155.0 kDa conjugate in particular resembled that of a sustained release depot, with no peak-to-valley effect that can cause undesirable side effects.

TABLE 4

Summary of statistical significance levels of MW-dependent fed blood glucose measurements of EG9 exendin-C-POEGMA conjugates shown in FIGS. 3A-3F compared to PBS control.

| | | EG9 exendin-POEGMA | | | |
|---|---|---|---|---|---|
| Time (h) | exendin | 25.4 kDa | 54.6 kDa | 97.2 kDa | 155.0 kDa |
| 1 | *** | **** | | | |
| 4 | **** | **** | *** | * | |
| 6 | **** | — | — | — | — |
| 8 | | **** | **** | ** | * |
| 24 | | **** | **** | **** | **** |
| 48 | | * | **** | **** | **** |
| 72 | | ** | **** | **** | **** |
| 96 | | | *** | *** | **** |
| 120 | | | | ** | |

Data were analyzed by repeated measures two-way ANOVA, followed by post hoc Dunnett's multiple comparison test to evaluate individual differences between a treatment and PBS control at each time point (n = 6, * $P < 0.05$,  $P < 0.01$, * $P < 0.001$ and **** $P < 0.0001$). — Groups treated with conjugates were not measured at t = 6 h.

Figure 3A:
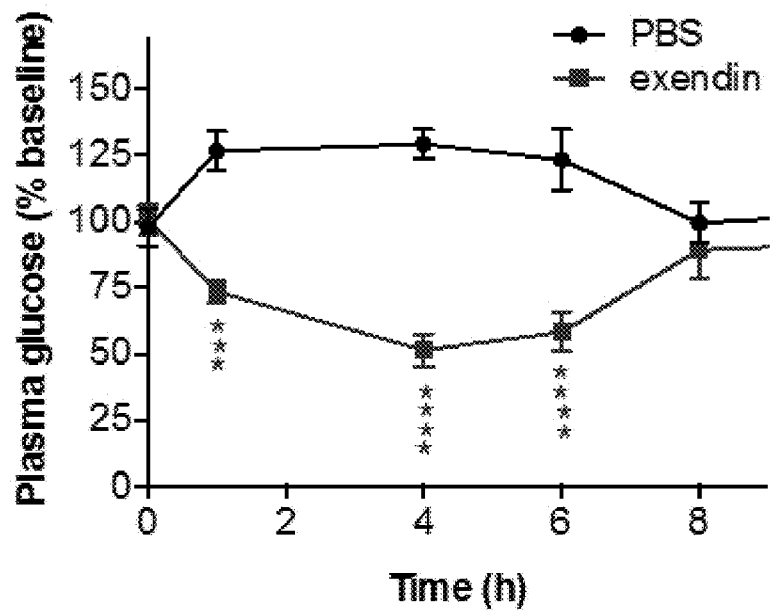
FIGS. 3A-3F are an assessment of MW-dependent in vivo efficacy of EG9 exendin-C-POEGMA conjugates. Blood glucose levels in fed mice were measured before and after a single s.c. injection of FIG. 3A, unmodified exendin, or FIGS. 3B-3E, 25.4 kDa, 54.6 kDa, 97.2 kDa, and 155.0 kDa EG9 exendin-C-POEGMA conjugates, compared to PBS control. The peptide and conjugates were administered at 25 nmol/kg and PBS was injected at equivalent volume at t=0 h. Blood glucose levels were normalized to the average glucose levels measured 24 h and immediately before injection. Data were analyzed by repeated measures two-way analysis of variance (ANOVA), followed by post hoc Dunnett's multiple comparison test.
Figure 3B:
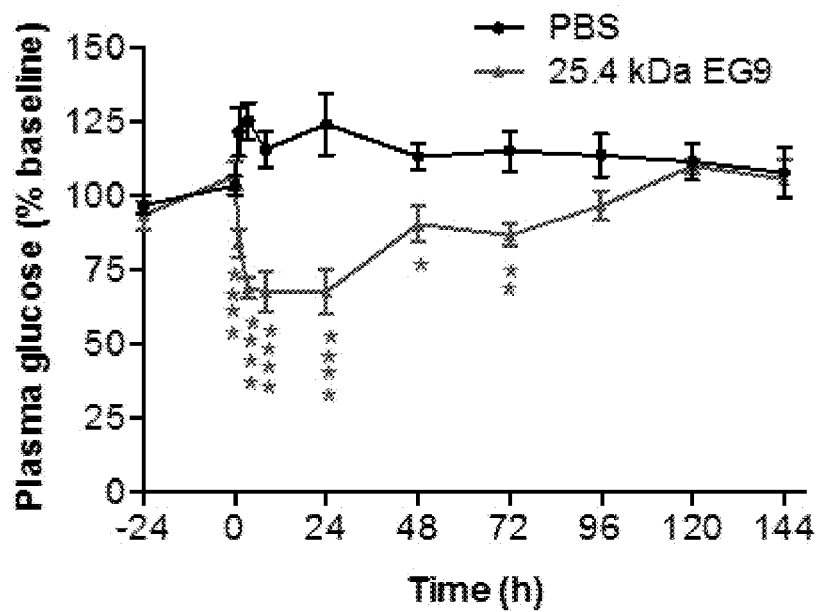
Figure 3C:
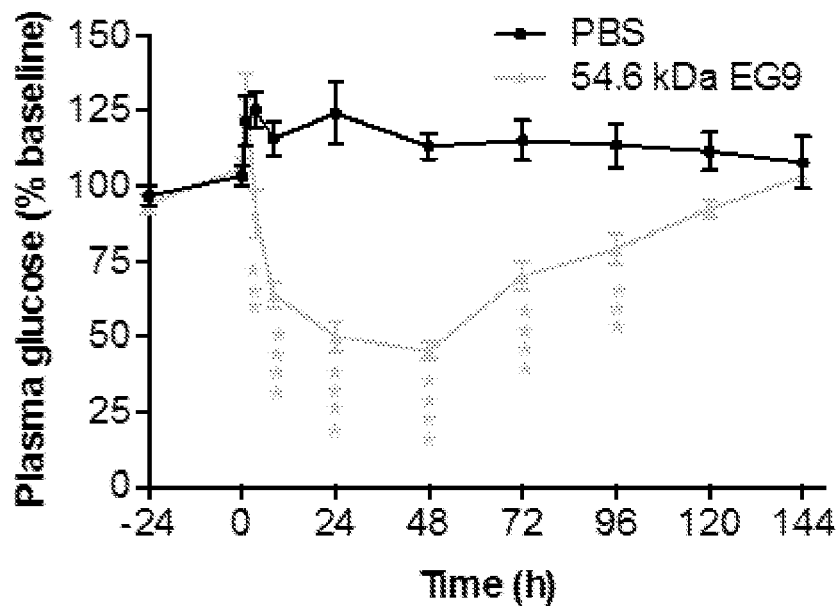
Figure 3D:
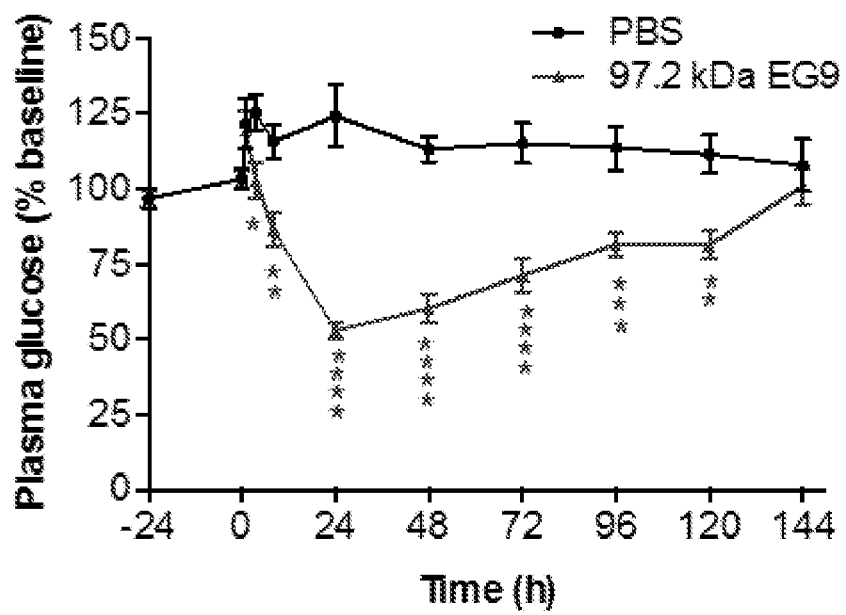
Figure 3E:
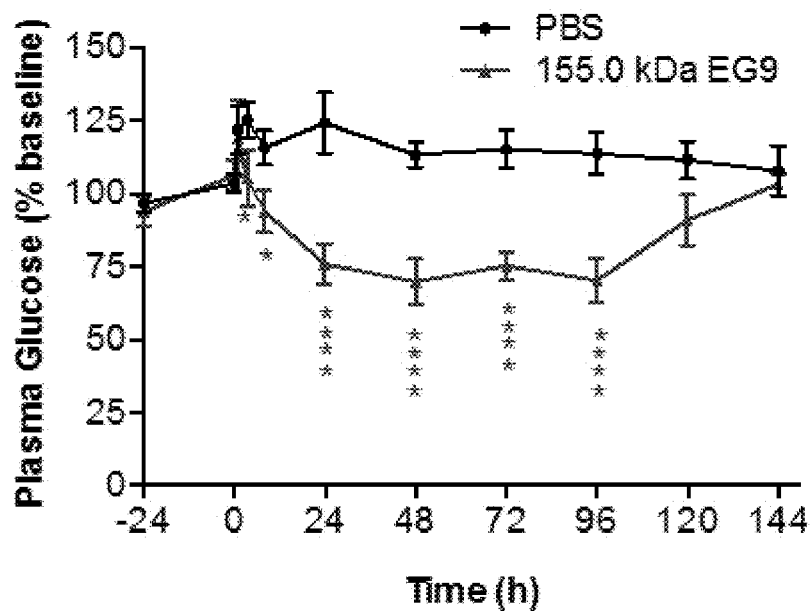
Figure 3F:
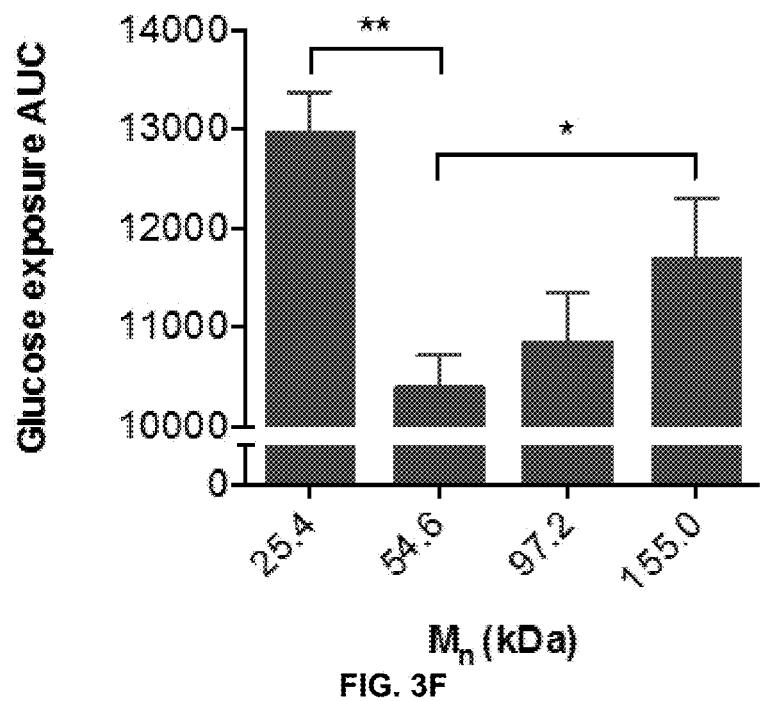

The in vitro cAMP results and the in vivo MW-dependent fed glucose measurements collectively show that an increase in MW of the conjugated polymer decreases the potency but increases the circulation duration of the EG9 exendin-POEGMA conjugate. Therefore, we hypothesize that there exists an optimal MW of the conjugate that best balances these two opposing effects. The area under the curve (AUC) of the fed glucose profiles with respect to 0% baseline signifies total glucose exposure, which accounts for both the magnitude and duration of glucose reduction, and is therefore a manifestation of the combined effect of the two opposing factors. Plotting the AUC of fed glucose levels as a function of conjugate $M_n$ indeed yielded a roughly inverted bell-shaped distribution with a minimum at 54.6 kDa (FIG. 3F). This suggests that the 54.6 kDa conjugate is the optimal among the tested EG9 conjugates in terms of balancing receptor activation potency and sustained duration of action. We thus investigated the 54.6 kDa EG9 conjugate further in subsequent experiments.

Figure 4C:
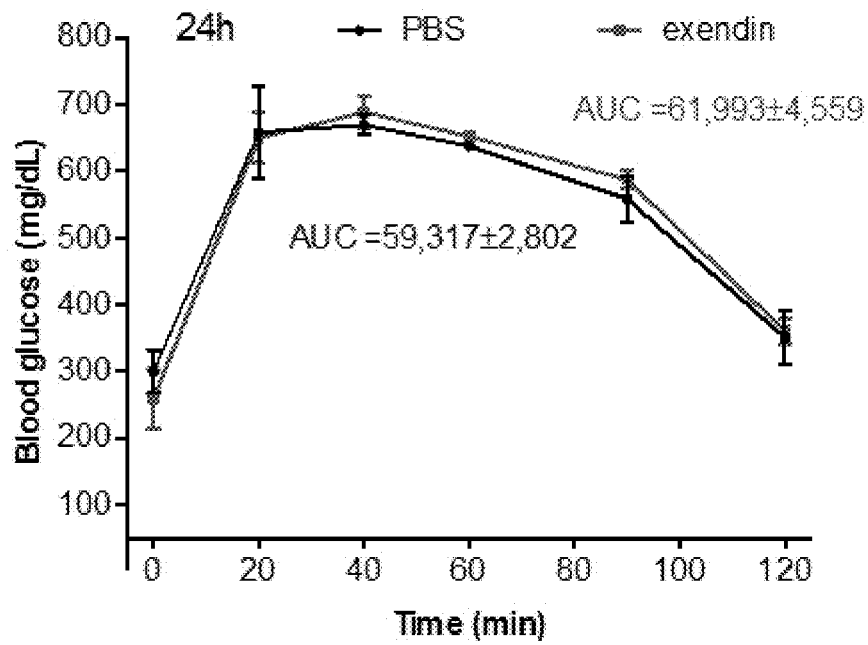
Figure 4D:
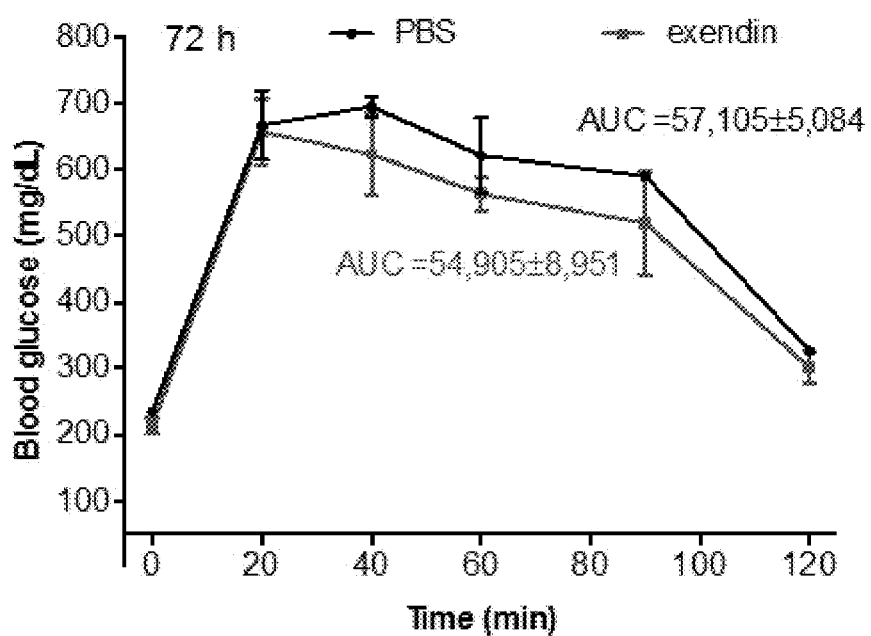

To validate the results from the fed glucose measurements and to obtain further evidence of the efficacy of EG9 exendin-C-POEGMA conjugates, an intraperitoneal glucose tolerance test (IPGTT) was performed 24 h and 72 h after a single s.c. injection of the 54.6 kDa EG9 conjugate or unmodified exendin at 25 nmol/kg. IPGTT confirmed the prolonged presence of the conjugate in circulation and its significant effect on glycemic control: at 24 h post-injection, the AUC of blood glucose level over 2 h after glucose challenge is reduced by 68% (P<0.0001, FIG. 4A), and at 72 h post-injection, the AUC is reduced by 48% for conjugate-treated mice compared with PBS controls (P<0.01, FIG. 4B). This is in stark contrast to the unmodified exendin group, which was insignificant at both time points (FIG. 4C and FIG. 4D).

EXAMPLE 5

Antigenicity of EG9 Exendin-C-POEGMA Conjugates

We tested the reactivity of the 54.6 kDa EG9 exendin-C-POEGMA conjugate to anti-PEG antibodies in plasma samples of patients previously treated with PEGylated proteins using enzyme-linked immunosorbant assay (ELISA). In a direct ELISA, the 54.6 kDa EG9 exendin-C-POEGMA conjugate and various controls, including two FDA-approved drugs, Adagen®—a PEGylated adenosine deaminase for treating severe combined immunodeficiency disease (SCID) and Krystexxa®—a PEGylated uricase for treating chronic refractory gout, were directly coated on a plate and probed with diluent, an anti-PEG negative patient plasma sample or one of two anti-PEG positive patient plasma samples. As shown in FIG. 5A, while the EG9 exendin-C-POGEMA conjugate did show a small amount of binding to anti-PEG antibodies in the positive plasma samples, the extent of binding is significantly less than those of the two PEGylated positive controls. This result was confirmed by a competitive ELISA, where Krystexxa® was coated on wells, and different amounts of 54.6 kDa EG9 exendin-C-POEGMA and controls were added in solution to compete for binding to anti-PEG antibodies in an anti-PEG positive plasma sample. As can be seen in FIG. 5B, at all tested competing antigen amounts, 54.6 kDa EG9 exendin-C-POEGMA showed significantly reduced antibody binding compared to the positive control, Adagen®.

EXAMPLE 6

Exendin-C-POEGMA with Shorter Side-Chain Length

Figure 8B:
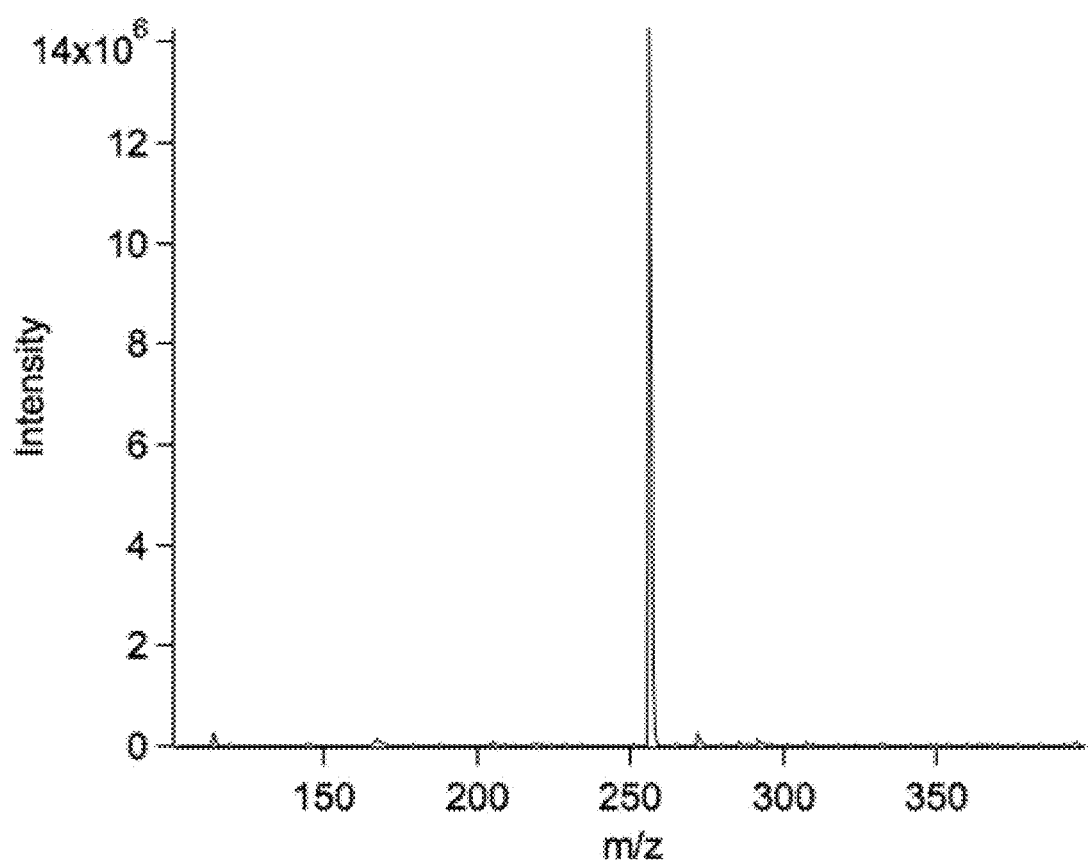

These results led us to hypothesize that the reduced PEG antigenicity of the EG9 exendin-C-POEGMA conjugate is due to both the branched architecture and the short side-chain length of the conjugated POEGMA. As a minimum length of PEG is presumably needed for antibody recognition and binding, we hypothesized that optimizing the side-chain OEG length may further reduce or possibly eliminate the antigenicity of POEGMA conjugates to anti-PEG antibodies. To test this hypothesis, we next synthesized exendin-C-POEGMA conjugates using OEGMA monomer with precisely 3 EG side-chain repeats as seen by LC/ESI-MS (FIG. 8B), as evidence in the literature suggests that the antigenic determinant of PEG may be ~6-7 EG repeats. Three different EG3 exendin-C-POEGMA conjugates with $M_n$s of 26.3, 55.6, and 71.6 kDa (TABLE 1) were synthesized. Assessment of conjugate potency by intracellular cAMP ELISA (FIG. 13) showed that similar to the EG9 conjugates, conjugation of EG3 POEGMA to the C-terminus of exendin caused an increase in the $EC_{50}$ (TABLE 1), indicating a decrease in the receptor activation of the conjugates, though with a less pronounced MW-dependence.

EXAMPLE 7

Antigenicity and Efficacy of EG3 Exendin-C-POEGMA Conjugates

We next tested the reactivity of a 55.6 kDa EG3 exendin-C-POEGMA conjugate to anti-PEG antibodies in patient plasma samples. The 54.6 kDa EG9 conjugate was included as a control to confirm the repeatability of the assays. Remarkably, both direct and competitive anti-PEG ELISAs (FIG. 5C and FIG. 5D) showed that reducing the side-chain length of the conjugated POEGMA down to 3 EG repeats completely eliminated the reactivity of the conjugate toward anti-PEG antibodies present in the patient plasma samples.

As the OEG side-chains on POEGMA are largely responsible for the "stealth" behavior of the polymer and its conjugates, alteration on the side-chain length can thus have an impact on the in vivo behavior of POEGMA conjugates.

Figure 6A:
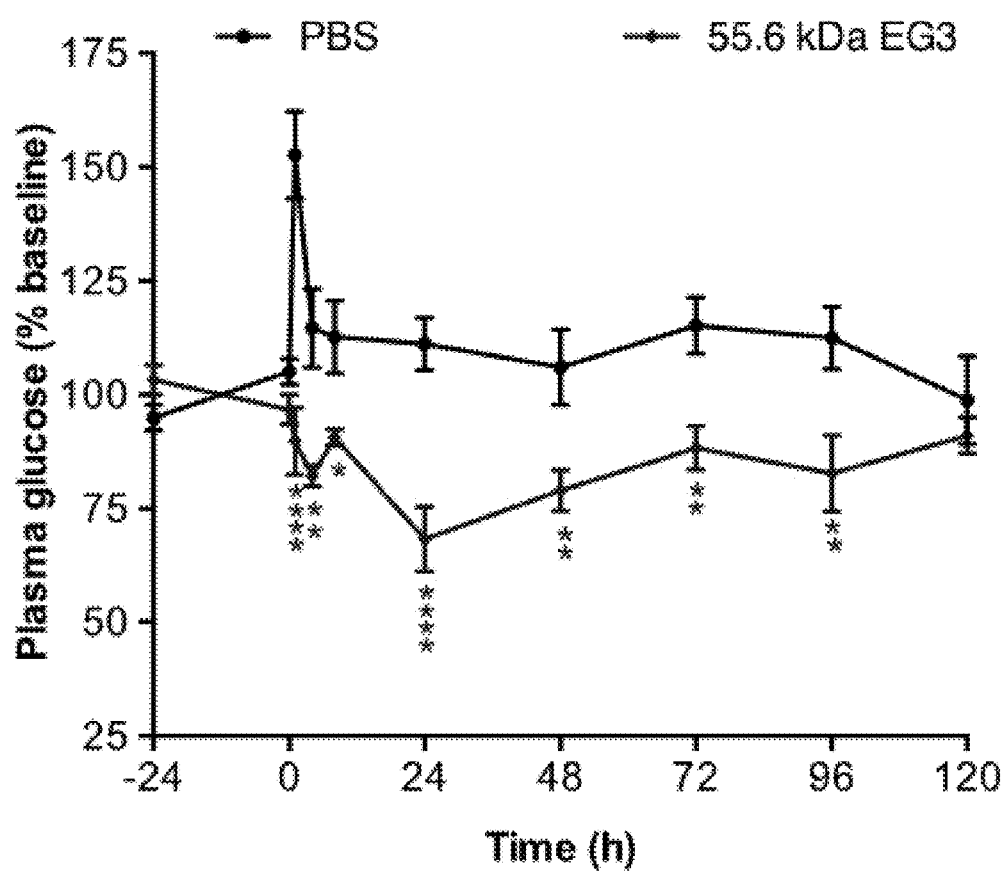
FIGS. 6A-6D are an assessment of in vivo efficacy and pharmacokinetics of exendin-C-POEGMA conjugates. Blood glucose levels in fed mice measured before and after a single s.c. injection of FIG. 6A, 55.6 kDa and FIG. 6B, 71.6 kDa EG3 exendin-C-POEGMA conjugates at 25 nmol/ kg or PBS at equivalent volume administered at t=0 h. Blood glucose levels were normalized to the average glucose levels measured 24 h and immediately before injection. Data were analyzed by repeated measures two-way ANOVA, followed by post hoc Dunnett's multiple comparison test (n=5, *P<0.05, P<0.01, and **P <0.0001).
Figure 6B:
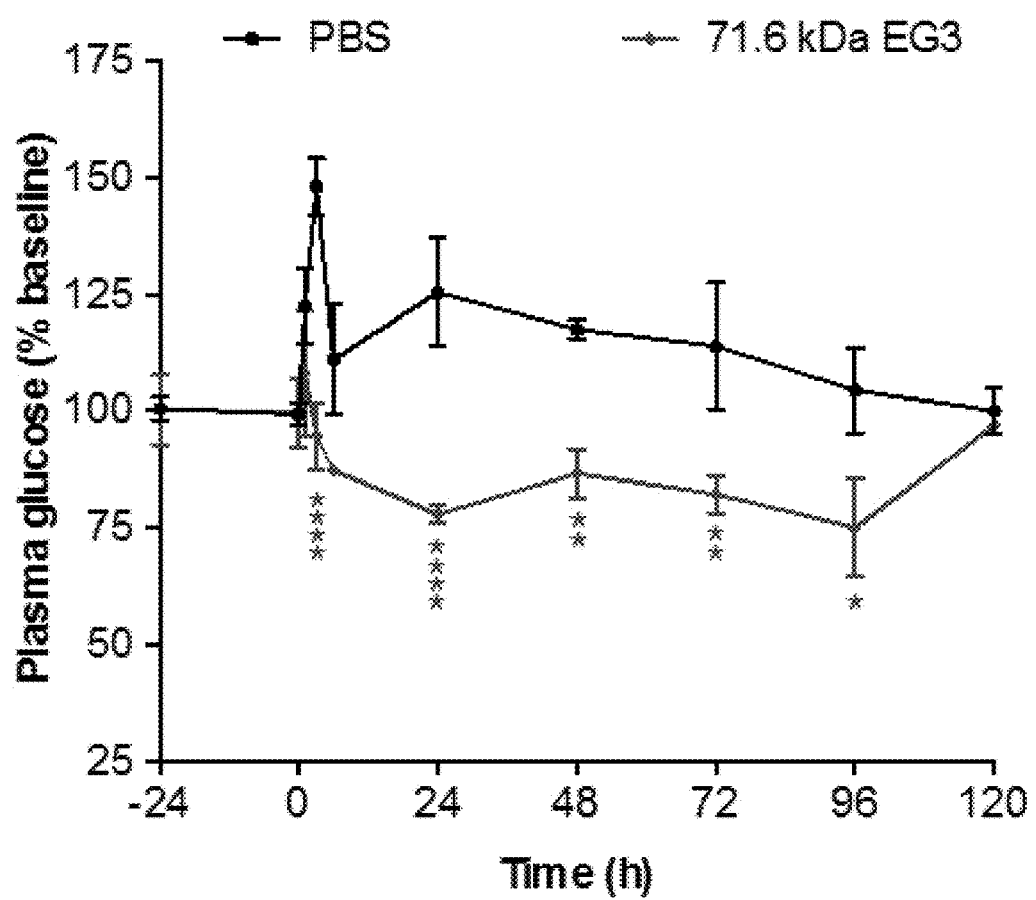

Therefore, we next investigated the in vivo efficacy of EG3 exendin-C-POEGMA. The 55.6 kDa and 71.6 kDa EG3 exendin-C-POEGMA conjugates were administered into fed mice via a single s.c. injection at 25 nmol/kg mouse body weight. As can be seen from the post-injection glucose profiles in FIG. 6A and FIG. 6B (unnormalized glucose profiles and weight profiles in FIGS. 14A-14D), both conjugates significantly reduced mouse blood glucose for up to 96 h compared to PBS control. The EG3 conjugates appear to have slightly lower magnitudes of glucose reduction and more flat glucose profiles compared to their EG9 counterparts.

EXAMPLE 8

Pharmacokinetics of Exendin-C-POEGMA Conjugates

To further confirm the prolonged circulation of exendin-C-POEGMA conjugates and to seek some answers to the difference between the glucose profiles of EG9 and EG3 conjugates, a pharmacokinetics study was performed with fluorescently labeled exendin, the 54.6 kDa EG9, 55.6 kDa EG3 and 71.6 kDa EG3 conjugates. Two MWs of the EG3 conjugate were tested, as the EG3 and EG9 conjugates have different $R_h$s at the same MW. The MWs were chosen such that the 54.6 kDa EG9 conjugate ($R_h$=5.4±0.6 nm) has similar MW as the 55.6 kDa EG3 conjugate and similar $R_h$ as the 71.6 kDa EG3 conjugate ($R_h$=5.6±0.5 nm). The plasma concentration-time courses (FIG. 6C and FIG. 6D) were analyzed using a non-compartmental fit characterizing the absorption and elimination phases of the pharmacokinetic profiles, to approximate the parameters shown in TABLE 2.

TABLE 2

Figure 6C:
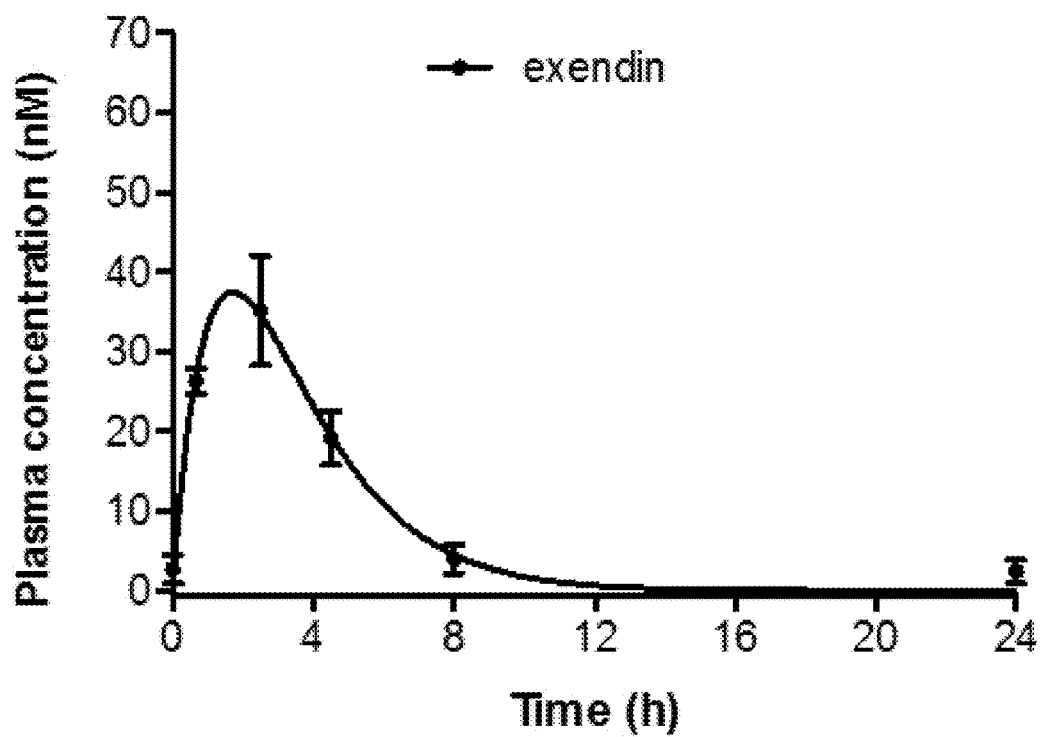
Figure 6D:
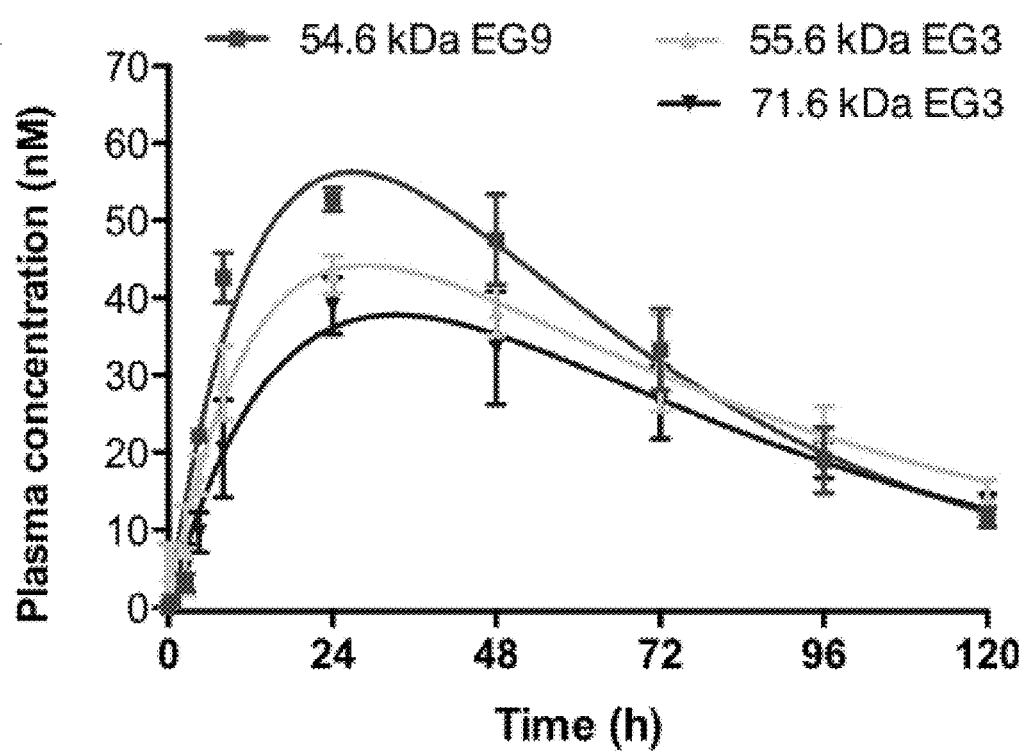

Pharmacokinetic parameters of exendin and exendin-C-POEGMA conjugates injected s.c. derived from data analyzed with a non-compartmental fit in FIG. 6C and FIG. 6D.

|  | $t_{1/2\ a}$ (h) | $t_{1/2\ el}$ (h) | $C_{max}$ (nM)[a] | $t_{max}$ (nM)[a] | AUC (h*nM)[b] |
| --- | --- | --- | --- | --- | --- |
| exendin | 0.7 ± 0.1 | 1.7 ± 0.2 | 37.1 ± 3.8 | 1.78 ± 0.1 | 217.5 ± 36.5 |
| 54.6 kDa EG9 | 6.2 ± 0.5 | 42.4 ± 2.9 | 56.4 ± 3.9 | 20.1 ± 0.4 | 4,795.5 ± 440.7 |
| 55.6 kDa EG3 | 7.6 ± 0.7 | 61.2 ± 5.0 | 44.0 ± 2.7 | 28.5 ± 2.3 | 4,775.0 ± 482.9 |
| 71.6 kDa EG3 | 9.0 ± 1.7 | 61.5 ± 3.2 | 37.7 ± 5.0 | 32.4 ± 3.9 | 4,411.2 ± 499.6 |

Values are reported as mean ± SEM. $t_{1/2\ a}$: absorption half-life, $t_{1/2\ el}$: elimination half-life, $C_{max}$: maximum plasma concentration, $t_{max}$: time to attain $C_{max}$.
[a]Derived from curve fitting.
[b]Calculated from t = 0 to ∞ from curve fitting.

After s.c. injection, unmodified exendin had a very short residence time in circulation, with a rapid absorption phase ($t_{1/2a}$=0.7±0.1 h) and a short terminal elimination phase ($t_{1/2el}$=1.7±0.2 h). In contrast, the exendin-C-POEGMA conjugates tested increased the absorption time by ~9 to 13-fold, with the two EG3 conjugates taking longer than the EG9 conjugate to absorb into circulation. Similarly, the 54.6 kDa EG9 conjugate prolonged the elimination phase of exendin by ~25-fold, while the two EG3 conjugates afforded a bigger increase of ~36-fold. These differences in the pharmacokinetics resulted in ~20-fold increase in AUC for the conjugates compared to unmodified exendin, indicating that conjugation of POEGMA to the C-terminus of exendin significantly enhanced the cumulative exposure of the peptide in circulation. While the $C_{max}$ of the two EG3 conjugates were considerably lower than that of the EG9 conjugate, consistent with the lower magnitude of glucose reduction seen for the EG3 conjugates in the fed blood glucose studies (FIG. 6A and FIG. 6B), the AUC of the three tested conjugates were comparable given the longer absorption and elimination half-lives of the EG3 conjugates.

EXAMPLE 9

Macroinitiator Characterization

Figure 15:
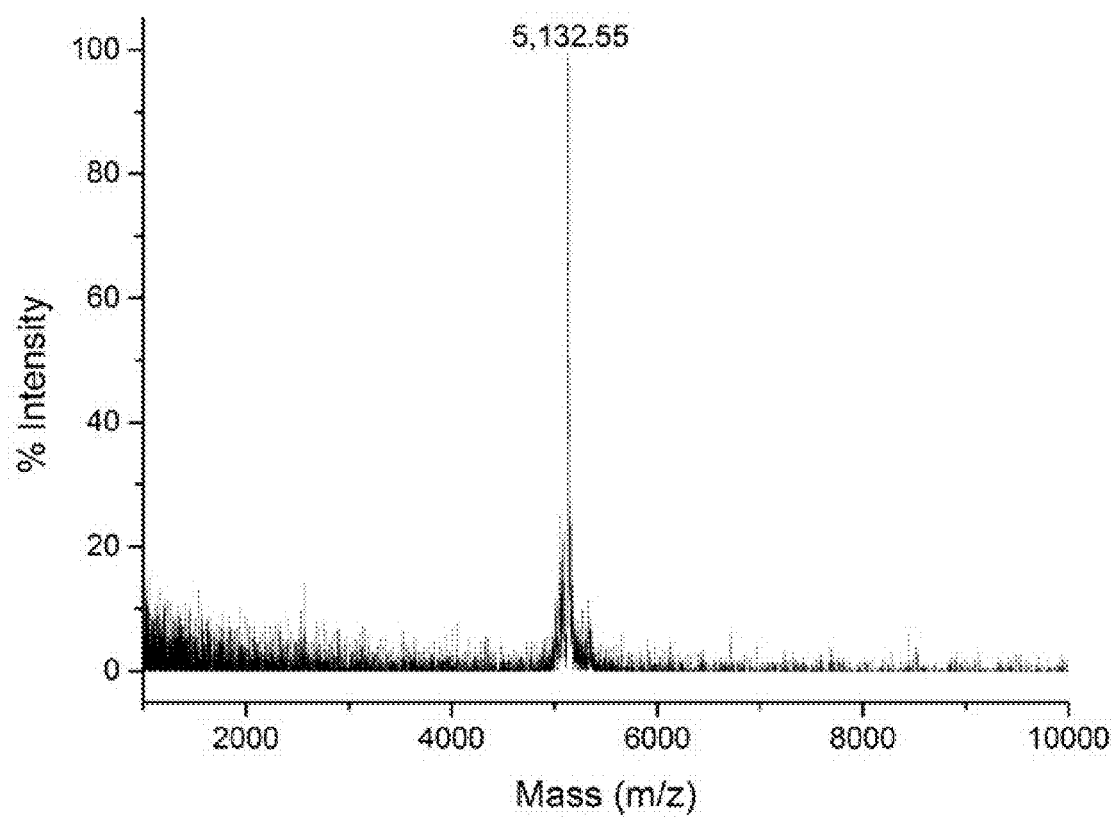
FIG. 15. MALDI-MS spectrum of exendin-C—Br macroinitiator. Major peak at 5,132.55 Da agrees well with theoretical mass of 5,131.44 Da corresponding to a single AEBMP initiator attached to exendin.
Figure 16A:
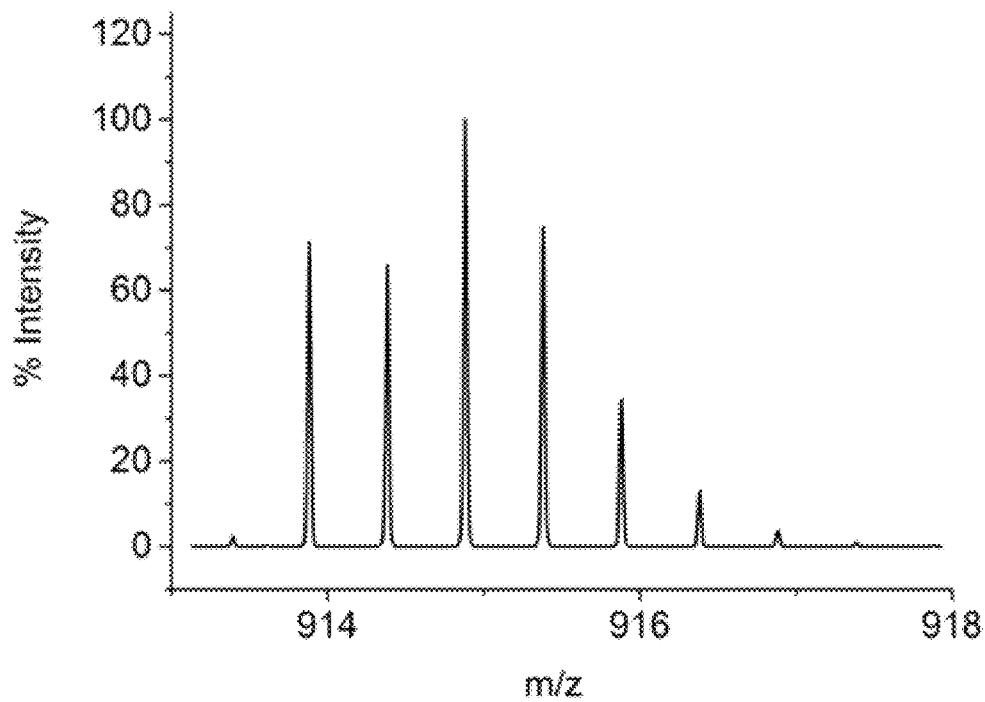
FIGS. 16A and 16B are an LC/MS-MS analysis of exendin-C—Br.
Figure 16B:
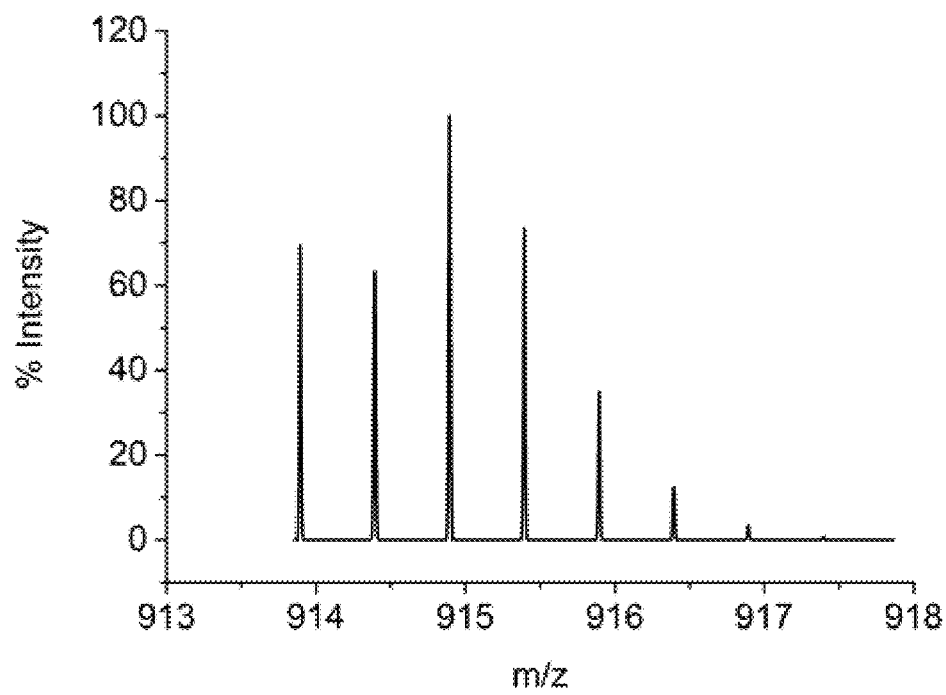

The purified exendin-C—Br macroinitiator was characterized by matrix assisted laser desorption ionization-mass spectrometry (MALDI-MS) to confirm initiator attachment (FIG. 15). A major peak was detected at 5,132.55 Da, which closely agrees with the theoretical mass of 5,131.44 Da corresponding to a single N-(2-(2-(2-(2-aminoacetamido) acet-amido)acetamido) ethyl)-2-bromo-2-methylpropanamide (AEBMP) initiator molecule attached to exendin. To verify the site-specificity of initiator attachment, exendin-C—Br was subjected to trypsin digestion and the peptide fragments were analyzed by liquid chromatography/tandem mass spectrometry (LC-MS/MS). Only the C-terminal peptide fragment was detected as a singly brominated cation and its experimental isotope distribution (FIG. 16A) showed nearly perfect overlap with its theoretical distribution (FIG. 16B), proving that a single initiator molecule was attached exclusively to the C-terminus of exendin.

Example 10

Characterization of EG3 Exendin-C-POEGMA Conjugates

Figure 17A:
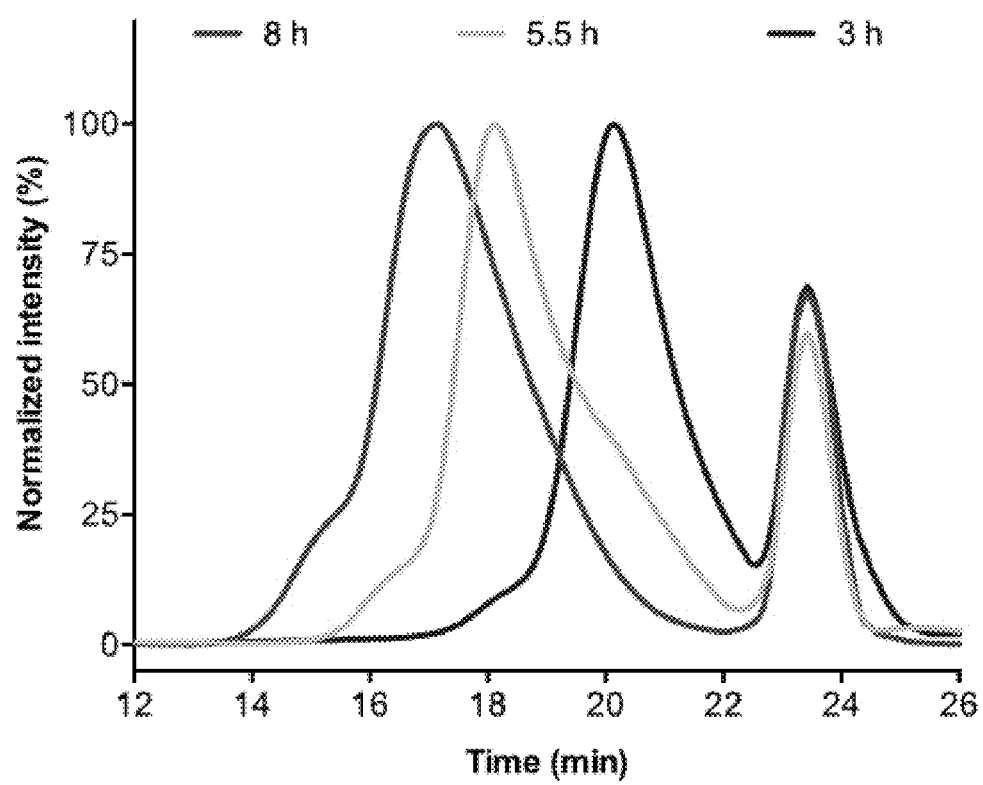
FIGS. 17A-17C physical characterization of EG3 exendin-C-POEGMA conjugates. SEC traces of EG3 exendin-C-POEGMA conjugates synthesized by in situ ATRP carried out for 2.5 h, 5.5 h, and 8 h, detected by FIG. 17A, UV-vis absorbance at 280 nm and FIG. 17B, RI. The signal from the residual exendin-C—Br was too low to be observed by RI detection due to its small size and low concentration.
Figure 17B:
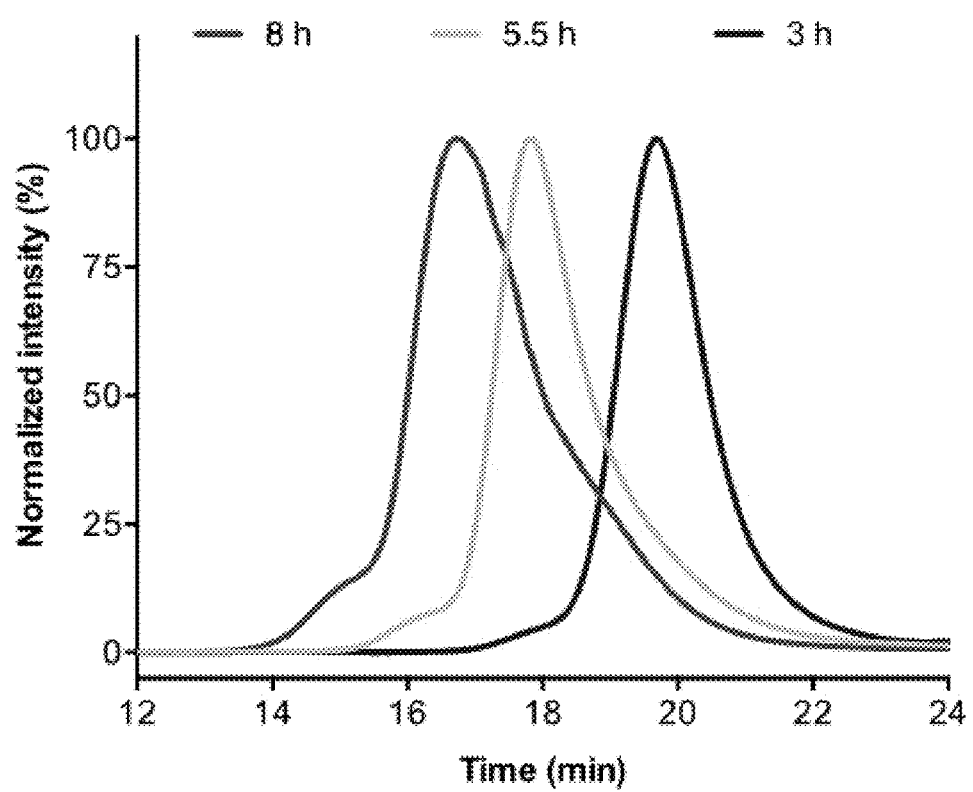
Figure 17C:
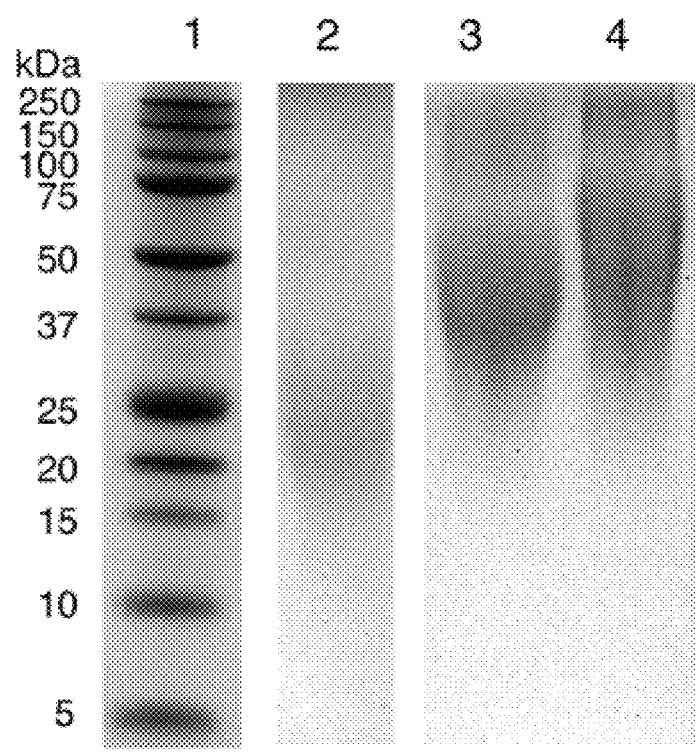

Three EG3 exendin-C-POEGMA conjugates of different molecular weights (MWs) were synthesized by varying Atom Transfer Radical Polymerization (ATRP) reaction times. The different MWs of the conjugates are evident from the Size Exclusion Chromatography (SEC) peaks eluting at 17.2, 18.2 and 20.3 min, detected by UV-vis absorbance at 280 nm (FIG. 17A) and refractive index (RI, FIG. 17B). Integration of peak areas in the UV-vis chromatograms showed that the conjugates constituted ~65% of the polymerization products on average. The relatively lower conjugation efficiency of the EG3 conjugates compared to their EG9 counterparts is speculated to be due to the considerably lower water solubility of the EG3 OEGMA monomer, though such a yield is still well above the yield that is typically achieved with conventional PEGylation. The conjugates were purified by a single round of preparative SEC (FIG. 17C).

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of reducing the antigenicity of a molecule, the method comprising conjugating at least one branched polymer to a molecule to form a molecule-polymer conjugate, wherein the molecule comprises a polypeptide, a polynucleotide, a small molecule, or a combination thereof, wherein the branched polymer comprises a backbone and a plurality of side chains, each side chain is covalently attached to the backbone, wherein the backbone comprises at least one of an acrylate, methacrylate, acrylamide, methacrylamide, carbonate, phosphoester, oxazoline, or a combination thereof, and wherein the molecule-polymer conjugate has reduced or eliminated antigenicity compared to a control.

Clause 2. The method of clause 1, wherein the molecule is conjugated to the backbone of the branched polymer.

Clause 3. The method of clause 1, wherein the molecule is conjugated to the backbone of the branched polymer via a linker.

Clause 4. The method of clause 1, wherein each side chain has a first terminal end and a second terminal end, wherein the first terminal end is covalently attached to the backbone, and wherein the second terminal end independently comprises an alkyl, ester, amine, amide, or carboxyl group.

Clause 5. The method of clause 1, wherein each side chain has a first terminal end and a second terminal end, wherein the first terminal end is covalently attached to the backbone, and wherein the second terminal end does not include a hydroxyl group.

Clause 6. The method of clause 1, wherein each side chain is a linear polymer.

Clause 7. The method of any one of the previous clauses, wherein at least one side chain comprises 1 monomer.

Clause 8. The method of any one of clauses 1-6, wherein each side chain comprises at least 2 monomers repeated in tandem.

Clause 9. The method of any one of clauses 1-6, wherein each side chain comprises less than 25 monomers repeated in tandem.

Clause 10. The method of any one of clauses 1-6, wherein each side chain comprises 3 to 9 monomers repeated in tandem.

Clause 11. The method of any one of clauses 1-6, wherein each side chain comprises 3 monomers repeated in tandem.

Clause 12. The method of any one of the previous clauses, wherein the monomer of each side chain is independently selected from betaine, phosphorylcholine, phosphorylethanolamine, sarcosine, ethylene glycol, or a combination thereof.

Clause 13. The method of clause 12, wherein the betaine comprises carboxybetaine, sulfobetaine, or a combination thereof.

Clause 14. The method of any one of the previous clauses, wherein the monomer of at least one side chain comprises ethylene glycol.

Clause 15. The method of any one of the previous clauses, wherein the monomer of each side chain comprises ethylene glycol.

Clause 16. The method of any one of the above clauses, wherein more than one branched polymer is conjugated to the molecule, each branched polymer conjugated to a different site of the molecule.

Clause 17. The method of any of one the above clauses, wherein the molecule comprises a polypeptide, and wherein one branched polymer is conjugated to the polypeptide at a site selected from the C-terminus, the N-terminus, and an internal amino acid of the polypeptide.

Clause 18. The method of any of one the above clauses, wherein the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

Clause 19. The method of any one of clauses 1-18, wherein the molecule comprises a polypeptide comprising a sortase A recognition site, and wherein the branched polymer and the polypeptide are incubated with sortase A under conditions to conjugate the branched polymer to the sortase recognition site of the polypeptide.

Clause 20. The method of any one of clauses 1-18, wherein the molecule comprises a polypeptide comprising a sortase A recognition site, and wherein the conjugating comprises: a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate.

Clause 21. The method of clause 19 or 20, wherein the sortase A recognition site comprises LPXTG (SEQ ID NO: 1), wherein X is any amino acid.

Clause 22. The method of clause 20 or 21, wherein the macroinitiator and monomer are incubated with a catalyst in step (b).

Clause 23. The method of any one of clauses 20 to 22, wherein the monomer in step (b) comprises at least one of an acrylate, methacrylate, acrylamide, and methacrylamide.

Clause 24. The method of any one of clauses 19 to 23, further comprising separating the molecule-polymer conjugate formed in step (b) from the unreacted macroinitiator.

Clause 25. The method of any one of clauses 1-18, wherein the branched polymer is synthesized and subsequently grafted to the molecule to form the molecule-polymer conjugate.

Clause 26. The method of any one of clauses 1-18, wherein the conjugating comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate.

Clause 27. The method of clause 25 or 26, wherein the branched polymer is synthesized using free-radical polymerization.

Clause 28. The method of clause 25 or 26, wherein the branched polymer is synthesized using at least one method selected from ionic ring-opening polymerization (ionic ROP), ring opening metathesis polymerization, ionic polymerization, condensation polymerization, and coordination polymerization.

Clause 29. A method of making a molecule-polymer conjugate having reduced or eliminated antigenicity compared to a control, from a molecule comprising a polypeptide having a sortase A recognition site, the method comprising: a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate, wherein the branched polymer comprises a backbone and a plurality of side chains, each side chain covalently attached to the backbone.

Clause 30. The method of clause 29, wherein the sortase A recognition site comprises LPXTG (SEQ ID NO: 1), wherein X is any amino acid.

Clause 31. The method of clause 29 or 30, wherein the macroinitiator and monomer are incubated with a catalyst in step (b).

Clause 32. The method of any one of clauses 29 to 31, wherein the monomer in step (b) comprises at least one of an acrylate, methacrylate, acrylamide, and methacrylamide.

Clause 33. The method of any one of clauses 29 to 32, further comprising separating the molecule-polymer conjugate formed in step (b) from the unreacted macroinitiator, wherein the yield of molecule-polymer conjugate is at least about 50% of the total conjugates and macroinitiators which are separated.

Clause 34. The method of clause 33 or 24, wherein the molecule-polymer conjugate is separated by chromatography.

Clause 35. The method of clause 34, wherein the chromatography comprises size-exclusion chromatography, ion exchange chromatography, affinity chromatography, or hydrophobic interaction chromatography, or a combination thereof.

Clause 36. The method of clause 35, wherein the chromatography comprises size-exclusion chromatography.

Clause 37. The method of any one of clauses 20-24, 27, and 29-36, wherein the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

Clause 38. The method of any one of clauses 29 to 37, wherein the molecule comprises a polypeptide, a polynucleotide, a small molecule, or a combination thereof.

Clause 39. A molecule-polymer conjugate having reduced or eliminated antigenicity compared to a control, the molecule-polymer conjugate comprising: a branched polymer comprising a backbone and a plurality of side chains, each side chain covalently attached to the backbone; and a molecule conjugated to the backbone of the branched polymer, wherein the molecule comprises a polypeptide, a polynucleotide, a small molecule, or a combination thereof, wherein each side chain is a linear polymer, wherein the backbone comprises at least one of an acrylate, methacrylate, acrylamide, methacrylamide, carbonate, phosphoester, oxazoline, or a combination thereof.

Clause 40. The conjugate of clause 39, wherein the molecule is conjugated to the backbone of the branched polymer via a linker.

Clause 41. The conjugate of any one of clauses 39-40, wherein each side chain has a first terminal end and a second terminal end, wherein the first terminal end is covalently attached to the backbone, and wherein the second terminal end independently comprises an alkyl, ester, amine, amide, or carboxyl group.

Clause 42. The conjugate of any one of clauses 39-41, wherein each side chain has a first terminal end and a second terminal end, wherein the first terminal end is covalently attached to the backbone, and wherein the second terminal end does not include a hydroxyl group.

Clause 43. The conjugate of any one of clauses 39-42, wherein at least one side chain comprises 1 monomer.

Clause 44. The conjugate of any one of clauses 39-42, wherein each side chain comprises at least 2 monomers repeated in tandem.

Clause 45. The conjugate of any one of clauses 39-42, wherein each side chain comprises less than 25 monomers repeated in tandem.

Clause 46. The conjugate of any one of clauses 39-42, wherein each side chain comprises 3 to 9 monomers repeated in tandem.

Clause 47. The conjugate of any one of clauses 39-42, wherein each side chain comprises 3 monomers repeated in tandem.

Clause 48. The conjugate of any one of clauses 39-47, wherein the monomer of each side chain is independently selected from betaine, phosphorylcholine, phosphorylethanolamine, sarcosine, ethylene glycol, or a combination thereof.

Clause 49. The conjugate of clause 48, wherein the betaine comprises carboxybetaine, sulfobetaine, or a combination thereof.

Clause 50. The conjugate of any one of clauses 39-49, wherein the monomer of at least one side chain comprises ethylene glycol.

Clause 51. The conjugate of any one of clauses 39-49, wherein the monomer of each side chain comprises ethylene glycol.

Clause 52. The conjugate of any one of clauses 39-51, wherein more than one branched polymer is conjugated to the molecule, each branched polymer conjugated to a different site of the molecule.

Clause 53. The conjugate of any one of clauses 39-51, wherein the molecule comprises a polypeptide, and wherein one branched polymer is conjugated to the polypeptide at a site selected from the C-terminus, the N-terminus, and an internal amino acid of the polypeptide.

Clause 54. The conjugate of any one of clauses 39-51, wherein the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

Clause 55. The method or conjugate of any one of clauses 1-54, wherein the branched polymer comprises poly[oligo (ethylene glycol) methyl ether methacrylate] (POEGMA), and wherein the POEGMA comprises: a backbone comprising poly(methyl methacrylate); and a plurality of side chains covalently attached to the backbone, each side chain comprising at least 1 monomer of ethylene glycol (EG) repeated in tandem.

Clause 56. The method or conjugate of clause 55, wherein at least one side chain comprises 1 monomer of ethylene glycol (EG).

Clause 57. The method or conjugate of clause 55, wherein each side chain comprises at least 2 monomers of ethylene glycol (EG) repeated in tandem.

Clause 58. The method or conjugate of clause 55, wherein each side chain comprises at least 10 monomers of ethylene glycol (EG) repeated in tandem.

Clause 59. The method or conjugate of clause 55, wherein each side chain comprises less than 25 monomers of ethylene glycol (EG) repeated in tandem.

Clause 60. The method or conjugate of clause 55, wherein each side chain comprises 3 monomers of ethylene glycol (EG) repeated in tandem.

Clause 61. The method or conjugate of clause 55, wherein each side chain comprises 3 to 9 monomers of ethylene glycol (EG) repeated in tandem.

Clause 62. The method or conjugate of any one of clauses 55-61, wherein the molecule-POEGMA conjugate is not reactive with pre-existing anti-PEG antibodies in a subject.

Clause 63. The method or conjugate of any one of the preceding clauses, wherein the molecule comprises one or more peptides or protein therapeutic agents selected from a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone, GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GH RH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1 R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor VIIa, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof.

Clause 64. The method or conjugate of any of one the above clauses, wherein the molecule comprises a polypeptide, and wherein the polypeptide comprises a His-tag, a stimulus-responsive polypeptide, or a combination thereof.

Clause 65. The method or conjugate of clause 64, wherein the stimulus-responsive polypeptide is selected from an elastin-like polypeptide, a polypeptide comprising a repeated motif, and a resilin-like polypeptide.

Clause 66. The method or conjugate of any one of the preceding clauses, wherein the molecule-polymer conjugate has: an in vivo half-life that is at least 25% greater compared with the in vivo half-life of the molecule itself; or an in vivo biodistribution to a tissue, organ, or disease site that is at least 25% greater than the in vivo biodistribution of the molecule itself; or a reduced binding to anti-PEG antibodies compared to a control; or a reduced immune response compared to a control; or a combination thereof.

Clause 67. The method or conjugate of clause 66, wherein the molecule-polymer conjugates have an in vivo half-life that is at least 80% greater than the in vivo half-life of the molecule itself.

Clause 68. The method or conjugate of any one of clauses 1-67, wherein the control comprises the molecule conjugated to a polymer that is not branched.

Clause 69. The method or conjugate of any one of clauses 1-67, wherein the control comprises the molecule by itself.

Clause 70. The method or conjugate of any one of clauses 1-67, wherein the control comprises the molecule conjugated to a linear polymer.

Clause 71. The method or conjugate of any one of clauses 1-67, wherein the control comprises the molecule conjugated to unbranched PEG.

Clause 72. The method or conjugate of any one of the preceding clauses, wherein the molecule comprises a polypeptide, and wherein at least about 20% of the polypeptides have a conjugated branched polymer solely at the C-terminus.

Clause 73. The method or conjugate of clause 72, wherein at least about 75% of the polypeptides have a conjugated branched polymer solely at the C-terminus.

Clause 74. The method or conjugate of clause 72, wherein at least about 90% of the polypeptides have a conjugated branched polymer solely at the C-terminus.

Clause 75. The method or conjugate of any one of the preceding clauses, wherein the yield of molecule-polymer conjugate is at least about 75%.

Clause 76. The method or conjugate of any one of the preceding clauses, wherein the yield of molecule-polymer conjugate is at least about 85%.

---

SEQUENCES

SEQ ID NO: 1
Sortase A recognition site, polypeptide
LPXTG (where X is any amino acid)

SEQ ID NO: 2
Sortase A recognition site, polypeptide
LPETG

| SEQUENCES |
|---|
| SEQ ID NO: 3<br>Sortase A recognition site, polypeptide<br>LPXZG wherein X and Z are independently any amino acid<br><br>SEQ ID NO: 4<br>Linker, polypeptide<br>(GGC)<br><br>SEQ ID NO: 5<br>Linker, polypeptide<br>(GGC)$_8$ |

| SEQUENCES |
|---|
| SEQ ID NO: 6<br>Linker, polypeptide<br>(G4S)$_3$<br><br>SEQ ID NO: 7<br>Linker, polypeptide<br>(VPGXG)$_{16}$ wherein X is valine or cysteine present in a ratio of 1:1.<br><br>SEQ ID NO: 8<br>"AEBMP", polypeptide<br>NGGPSSGAPPPSLPET |

The invention claimed is:

1. A method of reducing the antigenicity of a molecule, the method comprising conjugating at least one branched polymer to a molecule to form a molecule-polymer conjugate,
wherein the molecule comprises a polypeptide, a polynucleotide, a small molecule, or a combination thereof,
wherein the branched polymer comprises poly[oligo(ethylene glycol) methyl ether methacrylate] (POEGMA), wherein the POEGMA comprises:
 a backbone comprising poly(methyl methacrylate); and
 a plurality of side chains covalently attached to the backbone, where each side chain comprises 2 to 9 monomers of ethylene glycol (EG) repeated in tandem;
 wherein the molecule-polymer conjugate is not reactive with pre-existing anti-PEG antibodies in a subject, and
 wherein the molecule-polymer conjugate has reduced or eliminated antigenicity compared to a control.

2. The method of claim 1, wherein the molecule is conjugated to the backbone of the branched polymer.

3. The method of claim 1, wherein each side chain has a first terminal end and a second terminal end, wherein the first terminal end is covalently attached to the backbone, and wherein the second terminal end independently comprises an alkyl, ester, amine, amide, or carboxyl group.

4. The method of claim 1, wherein each side chain has a first terminal end and a second terminal end, wherein the first terminal end is covalently attached to the backbone, and wherein the second terminal end does not include a hydroxyl group.

5. The method of claim 1, wherein each side chain comprises at least one monomer.

6. The method of claim 1, wherein the monomer of each side chain is independently selected from betaine, phosphorylcholine, phosphorylethanolamine, sarcosine, ethylene glycol, or a combination thereof.

7. The method of claim 1, wherein the molecule comprises a polypeptide, and wherein one branched polymer is conjugated to the polypeptide at a site selected from the C-terminus, the N-terminus, and an internal amino acid of the polypeptide.

8. The method of claim 1, wherein the molecule comprises a polypeptide comprising a sortase A recognition site, and wherein the branched polymer and the polypeptide are incubated with sortase A under conditions to conjugate the branched polymer to the sortase recognition site of the polypeptide.

9. The method of claim 1, wherein the branched polymer is synthesized and subsequently grafted to the molecule to form the molecule-polymer conjugate.

10. The method of claim 1, wherein the conjugating comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate.

11. A method of making a molecule-polymer conjugate having reduced or eliminated antigenicity compared to a control, from a molecule comprising a polypeptide having a sortase A recognition site, the method comprising:
 a) contacting the molecule with a sortase A and an initiator agent under conditions that permit attachment of the initiator agent to the sortase A recognition site to form a macroinitiator; and
 b) incubating the macroinitiator with a monomer under conditions that permit free-radical polymerization and formation of a branched polymer to occur from the initiator agent to form the molecule-polymer conjugate,
 wherein the branched polymer comprises poly[oligo(ethylene glycol) methyl ether methacrylate] (POEGMA),
wherein the POEGMA comprises:
 a backbone comprising poly(methyl methacrylate); and
 a plurality of side chains covalently attached to the backbone, where each side chain comprises 2 to 9 monomers of ethylene glycol (EG) repeated in tandem;
 wherein the molecule-polymer conjugate is not reactive with pre-existing anti-PEG antibodies in a subject.

12. The method of claim 11, wherein the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

13. A molecule-polymer conjugate having reduced or eliminated antigenicity compared to a control, the molecule-polymer conjugate comprising:
 a branched polymer comprising poly[oligo(ethylene glycol) methyl ether methacrylate] (POEGMA); and
 a molecule conjugated to the backbone of the branched polymer, wherein the molecule comprises a polypeptide, a polynucleotide, a small molecule, or a combination thereof,
 wherein the POEGMA comprises:
 a backbone comprising poly(methyl methacrylate); and
 a plurality of side chains covalently attached to the backbone, where each side chain comprises 2 to 9 monomers of ethylene glycol (EG) repeated in tandem;
 and wherein the molecule-polymer conjugate is not reactive with pre-existing anti-PEG antibodies in a subject.

14. The conjugate of claim 13, wherein each side chain has a first terminal end and a second terminal end, wherein the first terminal end is covalently attached to the backbone, and wherein the second terminal end independently comprises an alkyl, ester, amine, amide, or carboxyl group.

15. The conjugate of claim 13, wherein each side chain has a first terminal end and a second terminal end, wherein the first terminal end is covalently attached to the backbone, and wherein the second terminal end does not include a hydroxyl group.

16. The conjugate of claim 13, wherein each side chain comprises at least 3 monomers of ethylene glycol (EG) repeated in tandem.

17. The conjugate of claim 13, wherein the molecule comprises one or more peptides or protein therapeutic agents selected from a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone , GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GHRH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor VIIa, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof.

18. The conjugate of claim 13, wherein the molecule-polymer conjugate has:
 an in vivo half-life that is at least 25% greater compared with the in vivo half-life of the molecule itself; or
 an in vivo biodistribution to a tissue, organ, or disease site that is at least 25% greater than the in vivo biodistribution of the molecule itself; or
 a reduced binding to anti-PEG antibodies compared to a control; or
 a reduced immune response compared to a control; or
 a combination thereof.

19. The conjugate of claim 17, wherein the molecule comprises exendin.

20. The conjugate of claim 13, wherein the molecule comprises exendin and each side chain of POEGMA comprises 3 monomers ethylene glycol (EG) repeated in tandem.

21. The conjugate of claim 13, wherein the molecule comprises exendin and each side chain of POEGMA comprises 9 monomers ethylene glycol (EG) repeated in tandem.

\* \* \* \* \*